US007842470B2

(12) United States Patent
Conn

(10) Patent No.: US 7,842,470 B2
(45) Date of Patent: Nov. 30, 2010

(54) METHOD FOR PHARMACOPERONES CORRECTION OF GNRHR MUTANT PROTEIN MISFOLDING

(75) Inventor: P. Michael Conn, Portland, OR (US)

(73) Assignee: Oregon Health & Science University, Portland, OR (US)

(*) Notice: Subject to any disclaimer, the term of this patent is extended or adjusted under 35 U.S.C. 154(b) by 1210 days.

(21) Appl. No.: 11/050,662

(22) Filed: Feb. 2, 2005

(65) Prior Publication Data

US 2005/0203019 A1 Sep. 15, 2005

Related U.S. Application Data

(63) Continuation-in-part of application No. PCT/US2004/002290, filed on Jan. 27, 2004, and a continuation-in-part of application No. 10/492,295, filed as application No. PCT/US02/32399 on Oct. 8, 2002, now Pat. No. 7,695,917.

(60) Provisional application No. 60/443,691, filed on Jan. 29, 2003, provisional application No. 60/376,685, filed on Apr. 29, 2002, provisional application No. 60/328,319, filed on Oct. 9, 2001.

(51) Int. Cl.
G01N 33/53 (2006.01)
(52) U.S. Cl. ....................................................... 435/7.2
(58) Field of Classification Search ....................... None
See application file for complete search history.

(56) References Cited

U.S. PATENT DOCUMENTS

| 5,900,360 | A | 5/1999 | Welch et al. |
| 6,270,954 | B1 | 8/2001 | Welch et al. |
| 6,274,597 | B1 | 8/2001 | Fan et al. |
| 6,541,195 | B2 | 4/2003 | Welch et al. |
| 6,583,158 | B1 | 6/2003 | Fan et al. |
| 6,589,964 | B2 | 7/2003 | Fan et al. |
| 6,599,919 | B2 | 7/2003 | Fan et al. |
| 6,774,135 | B2 | 8/2004 | Fan et al. |
| 2002/0035072 | A1 | 3/2002 | Fan et al. |
| 2002/0198225 | A1 | 12/2002 | Fan et al. |
| 2005/0130972 | A1 | 6/2005 | Fan et al. |
| 2005/0137223 | A1 | 6/2005 | Fan et al. |

FOREIGN PATENT DOCUMENTS

WO  WO 03/038036 A2  5/2003

OTHER PUBLICATIONS

Brothers et al., "Human Loss-of-Function Gonadotropin-Releasing Hormone Receptor Mutants Retain Wild-Type Receptors in the Endoplasmic Reticulum: Molecular Basis of the Dominant-Negative Effect," *Mol. Endocrinol.* 18:1787-1797 (2004).
Castro-Fernandez et al., "Beyond the Signal Sequence: Protein Routing in Health and Disease," *Endocr. Rev.* 26:479-503 (2005).
Conn et al., "Protein Origami: Therapeutic Rescue of Misfolded Gene Products," *Mol. Interventions* 2:308-316 (2002).
Janovick et al., "Rescue of Hypogonadotropic Hypogonadism-Causing and Manufactured GnRH Receptor Mutants by Specific Protein-Folding Template: Misrouted Proteins as a Novel Disease Etiology and Therapeutic Target," *J. Clin. Endocrinol. Metab.* 87:3255-3262 (2002).
Janovick et al., "Structure-Activity Relations of Successful Pharmacologic Chaperones for Rescue of Naturally Occurring and Manufactured Mutants of the Gonadotropin-Releasing Hormone Receptor," *J. Pharmacol. Exp. Ther.* 305:608-614 (2003).
Leanos-Miranda et al., "In Vitro Coexpression and Pharmacological Rescue of Mutant Gonadotropin-Releasing Hormone Receptors Causing Hypogonadotropic Hypogonadism in Humans Expressing Compound Heterozygous Alleles," *J. Clin. Endocrinol. Metab.* 90:3001-3008 (2005).
Leanos-Miranda et al., "Dominant-Negative Action of Disease-Causing Gonadotropin-Releasing Hormone Receptor (GnRHR) Mutants: A Trait that Potentially Coevolved with Decreased Plasma Membrane Expression of GnRHR in Humans," *J. Clin. Endocrinol. Met.* 88:3360-3367 (2003).
Morello et al., "Pharmacological Chaperones Rescue Cell-Surface Expression and Function of Misfolded V2 Vasopressin Receptor Mutants," *J. Clin. Invest.* 105:887-895 (2000).
Ulloa-Aguirre et al., "Pharmacologic Rescue of Conformationally-Defective Proteins: Implications for the Treatment of Human Disease," *Traffic* 5:821-837 (2004).
Welch et al., "Influence of Molecular and Chemical Chaperones on Protein Folding," *Cell Stress Chaperones* 1:109-115 (1996).
Leaños-Miranda et al., "Receptor-Misrouting: an Unexpectedly Prevalent and Rescuable Etiology in GnRHR-Mediated Hypogonadotropic Hypogonadism," *J. Clin. Endocrinol. Metab.* 87:4825-4828, 2002.

Primary Examiner—Michael Pak
(74) Attorney, Agent, or Firm—Klarquist Sparkman, LLP

(57) ABSTRACT

This application relates to methods of identifying pharmacoperone agents that can restore function to a misfolded protein, such as a misfolded protein that causes disease. Also disclosed are methods of using such pharmacoperone agents to treat a disease or disorder that results from the misfolded protein.

25 Claims, 24 Drawing Sheets

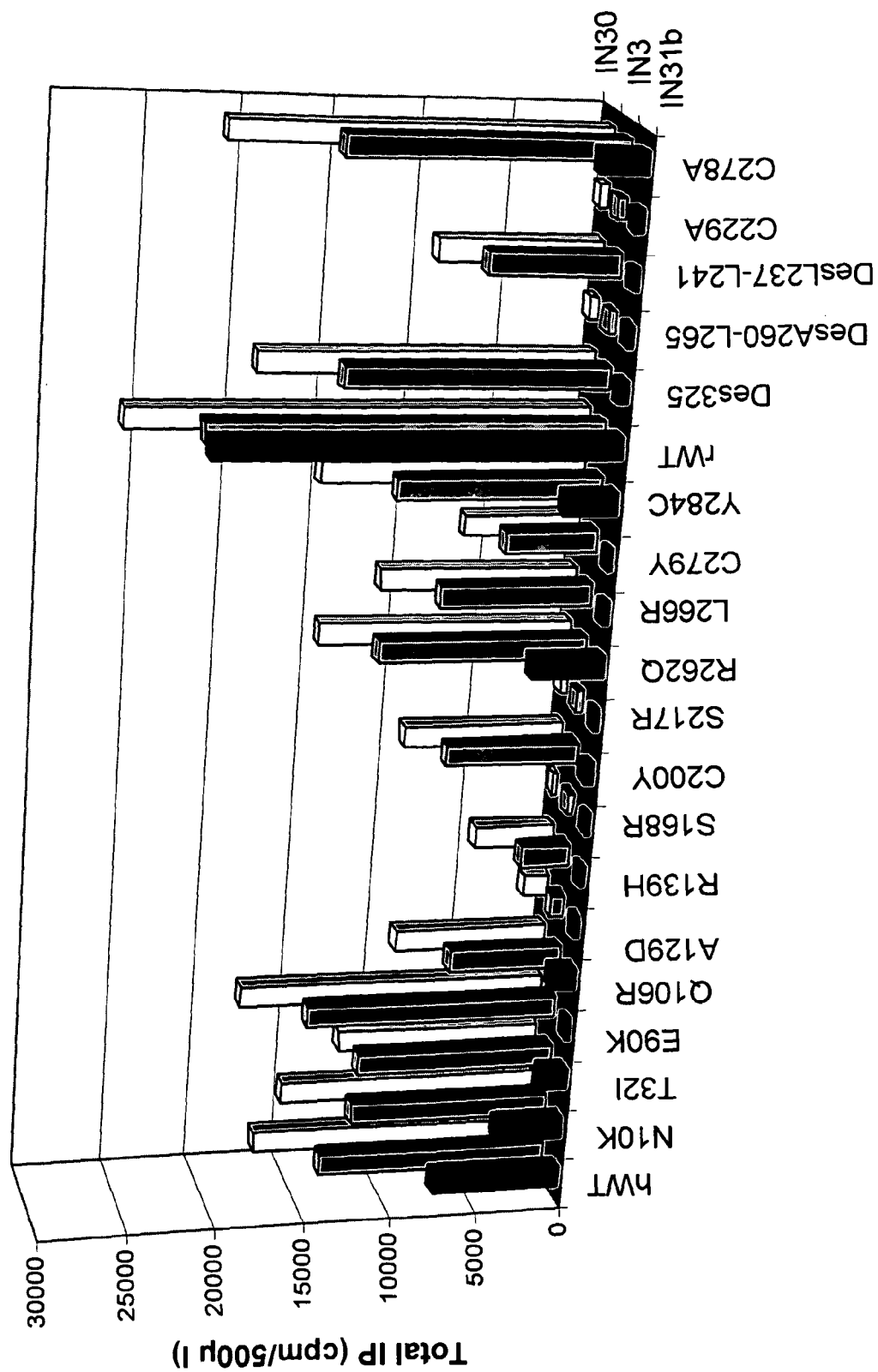

SEQUENCE LISTING

<160> NUMBER OF SEQ ID NOS: 2

<210> SEQ ID NO 1
<211> LENGTH: 328
<212> TYPE: PRT
<213> ORGANISM: Homo sapiens
<220> FEATURE:
<221> NAME/KEY: misc_feature
<222> LOCATION: (10)..(10)

```
<223> OTHER INFORMATION: Xaa can be Asn or Lys
<220> FEATURE:
<221> NAME/KEY: misc_feature
<222> LOCATION: (11)..(11)
<223> OTHER INFORMATION: Xaa can be Gln or Lys
<220> FEATURE:
<221> NAME/KEY: misc_feature
<222> LOCATION: (32)..(32)
<223> OTHER INFORMATION: Xaa can be Thr or Ile
<220> FEATURE:
<221> NAME/KEY: misc_feature
<222> LOCATION: (90)..(90)
<223> OTHER INFORMATION: Xaa can be Glu or Lys
<220> FEATURE:
<221> NAME/KEY: misc_feature
<222> LOCATION: (106)..(106)
<223> OTHER INFORMATION: Xaa can be Gln or Arg
<220> FEATURE:
<221> NAME/KEY: misc_feature
<222> LOCATION: (129)..(129)
<223> OTHER INFORMATION: Xaa can be Ala or Asp
<220> FEATURE:
<221> NAME/KEY: misc_feature
<222> LOCATION: (139)..(139)
<223> OTHER INFORMATION: Xaa can be Arg or His
<220> FEATURE:
<221> NAME/KEY: misc_feature
<222> LOCATION: (168)..(168)
<223> OTHER INFORMATION: Xaa can be Ser or Arg
<220> FEATURE:
<221> NAME/KEY: misc_feature
<222> LOCATION: (171)..(171)
<223> OTHER INFORMATION: Xaa can be Ala or Thr
<220> FEATURE:
<221> NAME/KEY: misc_feature
<222> LOCATION: (200)..(200)
<223> OTHER INFORMATION: Xaa can be Cys or Tyr
<220> FEATURE:
<221> NAME/KEY: misc_feature
<222> LOCATION: (217)..(217)
<223> OTHER INFORMATION: Xaa can be Ser or Arg
<220> FEATURE:
<221> NAME/KEY: misc_feature
<222> LOCATION: (262)..(262)
<223> OTHER INFORMATION: Xaa can be Arg or Gln
<220> FEATURE:
<221> NAME/KEY: misc_feature
<222> LOCATION: (266)..(266)
<223> OTHER INFORMATION: Xaa can be Leu or Arg
<220> FEATURE:
<221> NAME/KEY: misc_feature
<222> LOCATION: (279)..(279)
<223> OTHER INFORMATION: Xaa can be Cys or Arg
<220> FEATURE:
<221> NAME/KEY: misc_feature
<222> LOCATION: (284)..(284)
<223> OTHER INFORMATION: Xaa can be Tyr or Cys
<220> FEATURE:
<221> NAME/KEY: misc_feature
<222> LOCATION: (314)..(314)
<223> OTHER INFORMATION: Xaa can be Leu or a truncation mutation

<400> SEQUENCE: 1

Met Ala Asn Ser Ala Ser Pro Glu Gln Xaa Xaa Asn His Cys Ser Ala
1               5                  10                  15

Ile Asn Asn Ser Ile Pro Leu Met Gln Gly Asn Leu Pro Thr Leu Xaa
            20                  25                  30

Leu Ser Gly Lys Ile Arg Val Thr Val Thr Phe Phe Leu Phe Leu Leu
        35                  40                  45

Ser Ala Thr Phe Asn Ala Ser Phe Leu Leu Lys Leu Gln Lys Trp Thr
    50                  55                  60

Gln Lys Lys Glu Lys Gly Lys Lys Leu Ser Arg Met Lys Leu Leu Leu
65                  70                  75                  80
```

```
Lys His Leu Thr Leu Ala Asn Leu Leu Xaa Thr Leu Ile Val Met Pro
                85                  90                  95

Leu Asp Gly Met Trp Asn Ile Thr Val Xaa Trp Tyr Ala Gly Glu Leu
            100                 105                 110

Leu Cys Lys Val Leu Ser Tyr Leu Lys Leu Phe Ser Met Tyr Ala Pro
        115                 120                 125

Xaa Phe Met Met Val Val Ile Ser Leu Asp Xaa Ser Leu Ala Ile Thr
130                 135                 140

Arg Pro Leu Ala Leu Lys Ser Asn Ser Lys Val Gly Gln Ser Met Val
145                 150                 155                 160

Gly Leu Ala Trp Ile Leu Ser Xaa Val Phe Xaa Gly Pro Gln Leu Tyr
                165                 170                 175

Ile Phe Arg Met Ile His Leu Ala Asp Ser Ser Gly Gln Thr Lys Val
            180                 185                 190

Phe Ser Gln Cys Val Thr His Xaa Ser Phe Ser Gln Trp Trp His Gln
        195                 200                 205

Ala Phe Tyr Asn Phe Phe Thr Phe Xaa Cys Leu Phe Ile Ile Pro Leu
210                 215                 220

Phe Ile Met Leu Ile Cys Asn Ala Lys Ile Ile Phe Thr Leu Thr Arg
225                 230                 235                 240

Val Leu His Gln Asp Pro His Glu Leu Gln Leu Asn Gln Ser Lys Asn
                245                 250                 255

Asn Ile Pro Arg Ala Xaa Leu Lys Thr Xaa Lys Met Thr Val Ala Phe
            260                 265                 270

Ala Thr Ser Phe Thr Val Xaa Trp Thr Pro Tyr Xaa Val Leu Gly Ile
        275                 280                 285

Trp Tyr Trp Phe Asp Pro Glu Met Leu Asn Arg Leu Ser Asp Pro Val
290                 295                 300

Asn His Phe Phe Phe Leu Phe Ala Phe Xaa Asn Pro Cys Phe Asp Pro
305                 310                 315                 320

Leu Ile Tyr Gly Tyr Phe Ser Leu
                325

<210> SEQ ID NO 2
<211> LENGTH: 327
<212> TYPE: PRT
<213> ORGANISM: Rattus norvegicus
<220> FEATURE:
<221> NAME/KEY: misc_feature
<222> LOCATION: (11)..(11)
<223> OTHER INFORMATION: Xaa can be Gln or Pro
<220> FEATURE:
<221> NAME/KEY: misc_feature
<222> LOCATION: (24)..(24)
<223> OTHER INFORMATION: Xaa can be Met, Ile or Thr
<220> FEATURE:
<221> NAME/KEY: misc_feature
<222> LOCATION: (33)..(33)
<223> OTHER INFORMATION: Xaa can be Leu or Val
<220> FEATURE:
<221> NAME/KEY: misc_feature
<222> LOCATION: (58)..(58)
<223> OTHER INFORMATION: Xaa can be Leu or Val
<220> FEATURE:
<221> NAME/KEY: misc_feature
<222> LOCATION: (62)..(62)
<223> OTHER INFORMATION: Xaa can be Arg or Lys
<220> FEATURE:
<221> NAME/KEY: misc_feature
<222> LOCATION: (143)..(143)
<223> OTHER INFORMATION: Xaa can be Val or Ile
<220> FEATURE:
<221> NAME/KEY: misc_feature
```

```
<222> LOCATION: (152)..(152)
<223> OTHER INFORMATION: Xaa can be Lys or Asn
<220> FEATURE:
<221> NAME/KEY: misc_feature
<222> LOCATION: (157)..(157)
<223> OTHER INFORMATION: Xaa can be Arg or Gln
<220> FEATURE:
<221> NAME/KEY: misc_feature
<222> LOCATION: (160)..(160)
<223> OTHER INFORMATION: Xaa can be Val, Ile or Thr
<220> FEATURE:
<221> NAME/KEY: misc_feature
<222> LOCATION: (190)..(190)
<223> OTHER INFORMATION: Xaa can be Ala, Thr or Lys
<220> FEATURE:
<221> NAME/KEY: misc_feature
<222> LOCATION: (207)..(207)
<223> OTHER INFORMATION: Xaa can be Glu or Gln
<220> FEATURE:
<221> NAME/KEY: misc_feature
<222> LOCATION: (216)..(216)
<223> OTHER INFORMATION: Xaa can be Ser or Gly
<220> FEATURE:
<221> NAME/KEY: misc_feature
<222> LOCATION: (277)..(277)
<223> OTHER INFORMATION: Xaa can be Ile or Val

<400> SEQUENCE: 2

Met Ala Asn Asn Ala Ser Leu Glu Gln Asp Xaa Asn His Cys Ser Ala
1               5                   10                  15

Ile Asn Asn Ser Ile Pro Leu Xaa Gln Gly Lys Leu Pro Thr Leu Thr
                20                  25                  30

Xaa Ser Gly Lys Ile Arg Val Thr Val Thr Phe Phe Leu Phe Leu Leu
        35                  40                  45

Ser Thr Ala Phe Asn Ala Ser Phe Leu Xaa Lys Leu Gln Xaa Trp Thr
    50                  55                  60

Gln Lys Arg Lys Lys Gly Lys Lys Leu Ser Arg Met Lys Val Leu Leu
65              70                  75                  80

Lys His Leu Thr Leu Ala Asn Leu Leu Glu Thr Leu Ile Val Met Pro
                85                  90                  95

Leu Asp Gly Met Trp Asn Ile Thr Val Gln Trp Tyr Ala Gly Glu Phe
            100                 105                 110

Leu Cys Lys Val Leu Ser Tyr Leu Lys Leu Phe Ser Met Tyr Ala Pro
        115                 120                 125

Ala Phe Met Met Val Val Ile Ser Leu Asp Arg Ser Leu Ala Xaa Thr
    130                 135                 140

Gln Pro Leu Ala Val Gln Ser Xaa Ser Lys Leu Glu Xaa Ser Met Xaa
145                 150                 155                 160

Ser Leu Ala Trp Ile Leu Ser Ile Val Phe Ala Gly Pro Gln Leu Tyr
                165                 170                 175

Ile Phe Arg Met Ile Tyr Leu Ala Asp Gly Ser Gly Pro Xaa Val Phe
            180                 185                 190

Ser Gln Cys Val Thr His Cys Ser Phe Pro Gln Trp Trp His Xaa Ala
        195                 200                 205

Phe Tyr Asn Phe Phe Thr Phe Xaa Cys Leu Phe Ile Ile Pro Leu Leu
    210                 215                 220

Ile Met Leu Ile Cys Asn Ala Lys Ile Ile Phe Ala Leu Thr Arg Val
225                 230                 235                 240

Leu His Gln Asp Pro Arg Lys Leu Gln Leu Asn Gln Ser Lys Asn Asn
                245                 250                 255

Ile Pro Arg Ala Arg Leu Arg Thr Leu Lys Met Thr Val Ala Phe Ala
            260                 265                 270
```

```
Thr Ser Phe Val Xaa Cys Trp Thr Pro Tyr Tyr Val Leu Gly Ile Trp
        275             280                 285

Tyr Trp Phe Asp Pro Glu Met Leu Asn Arg Val Ser Glu Pro Val Asn
    290             295                 300

His Phe Phe Phe Leu Phe Ala Phe Leu Asn Pro Cys Phe Asp Pro Leu
305                 310                 315                 320

Ile Tyr Gly Tyr Phe Ser Leu
                325
```

METHOD FOR PHARMACOPERONES CORRECTION OF GNRHR MUTANT PROTEIN MISFOLDING

CROSS REFERENCE TO RELATED APPLICATIONS

This is a continuation in part (CIP) of PCT/US04/02290 filed Jan. 27, 2004, which claims the benefit of U.S. Provisional Application No. 60/443,691 filed Jan. 29, 2003, and is also a CIP of U.S. application Ser. No. 10/492,295 filed Apr. 8, 2004 now U.S. Pat. No. 7,695,917, which is a §371 U.S. National Stage of PCT/US02/32399 filed Oct. 8, 2002, which claims the benefit of U.S. Provisional Application No. 60/376,685 filed Apr. 29, 2002 and the benefit of U.S. Provisional Application No. 60/328,319 filed Oct. 9, 2001, all herein incorporated by reference.

ACKNOWLEDGMENT OF GOVERNMENT SUPPORT

Some of the work described in this patent application was funded by NIH grants HD-19899, RR-00163, HD-18185 and TW/HD-00668. The government of the United States may have certain rights in this invention.

FIELD

This disclosure relates to methods of screening agents for their ability to restore functionality to a mutant protein that is mis-folded, such as a receptor, and methods of using identified agents to treat a subject having a disorder related to the mis-folded mutant protein.

BACKGROUND

Receptors, hormones, enzymes, ion channels and structural components of the cell are created by protein synthesis. Synthesis alone is insufficient for proper function. For a cell to operate effectively, its components must be correctly compartmentalized. Proteins containing mutations that lead to mis-folding of the protein and resulting aggregation of the protein or mis-routing of the protein can result in disease due to loss of protein function, creation of toxic functions or interference with normal functions of other molecules. For example, mutations in amyloid precursor protein result in aggregation of the amyloid protein, which can result in Alzheimer's disease, while mutations in the gonadotropin-releasing hormone receptor (GnRHR) can result in an inability of the GnRHR to properly traffic to the cell surface, resulting in hypogonadotropic hypogonadism (HH).

Several approaches have been applied to salvage defective proteins. Among these are genetic approaches, such as increased receptor expression to produce larger numbers of receptors (Cheng et al., *Am. J. Physiol.* 268:L615-24, 1995; Schülein et al., *J. Biol. Chem.* 276:8384-92, 2001; Maya-Nùñez et al., *J. Clin. Endocrinol. Metab.* 87:2144-9, 2002). However, increasing the number of properly folded or properly trafficked proteins in a cell by genetic approaches is not presently practical for in vivo use.

Other methods of correcting defective receptors include the use of non-specific protein stabilizing agents to stabilize extant molecules rendered incompetent by genetic defects, such as polyols and sugars (Back et al. *Biochemistry* 18:5291-6, 1979; Brown et al., *J. Clin. Invest.* 99:1432-44, 1997; Brown et al., *Cell Stress Chaperones* 1:117-24, 1996; Sato et al., *J. Biol. Chem.* 271:635-8, 1996; U.S. Pat. Nos. 6,541,195 and 6,270,954 to Welch et al.), or physical methods (Denning et al., *Nature* 358:761-4, 1992; Brown et al., *J. Clin. Invest.*; 99:1432-1444, 1997; Matsuda et al., *J. Biol. Chem.*; 274: 34515-8, 1999; Zhou et al., *J. Biol. Chem.* 274:31123-6, 1999). However, previously disclosed protein stabilizing agents are non-specific, leading to many side effects, and the amount of agent needed to treat the defect would be toxic in vivo, which generally precludes their use in a clinical setting (Welch, *Semin. Cell Dev. Biol.* 15:31-8, 2004).

Therefore, there is a need for a method to restore function to mutant proteins that are mis-folded, such as mutant receptors, that is specific for the protein of interest and which can be used therapeutically in vivo. In addition, there is a need for methods that allow one to screen for therapeutically effective agents that can be used to treat subjects having diseases associated with mis-folded mutated proteins that result in protein aggregation or protein mis-routing in a cell.

SUMMARY

It has been determined that compounds from several different chemical families can restore function to many gonadotropin-releasing hormone receptor (GnRHR) mutants that are mis-folded and do not properly localize to the cell surface membrane. A model is described whereby chemically distinct agents serve as molecular scaffolding (herein referred to as "pharmacoperones"), allowing mutant proteins to fold correctly and thereby avoid detection by the cellular quality control apparatuses. The correctly folded protein can then be properly routed in the cell (or if the mis-folding results in aggregation, the properly folded protein will have decreased aggregation). In particular examples, pharmacoperones rescue mutant receptors, thereby allowing the mutant receptor to traffic to the cell membrane and be available for ligand binding. The pharmacoperones act as pharmaceutical agents that in disclosed examples can act selectively at the misfolded protein, as opposed to generally stabilizing all proteins throughout the body.

Based on these observations, assays are disclosed for detecting one or more pharmacoperone agents that restore function to a mis-folded protein having reduced biological activity, such as a mutant cell surface membrane receptor, mutant ion channel, or mutant enzyme. Mis-folded proteins can result in aggregation of the mutant protein, mis-trafficking of the protein within the cell (for example an inability to efficiently route to the cell surface membrane), or both. In particular examples, pharmacoperone agents that can restore function to one particular mutation can also rescue at least one other mutation found in that mutant protein that results in disease. For example, a pharmacoperone that can rescue an $E^{90}K$ human GnRHR mutation can also rescue another mutation in the human GnRHR amino acid sequence that results in disease, such as an $N^{10}K$ mutation, a $T^{32}I$ mutation, a $Q^{106}R$ mutation, an $A^{129}D$ mutation, an $R^{139}H$ mutation, a $A^{171}T$ mutation, a $C^{200}Y$ mutation, an $R^{262}Q$ mutation, a $L^{266}R$ mutation, a $C^{279}Y$ mutation, a $Y^{284}C$ mutation, or combinations thereof (for example, see Table 1).

In some embodiments, the assay includes selecting at least one test agent that can penetrate a cell membrane and substantially specifically bind to the protein of interest, for example without significantly interfering with the biological activity of the wild-type protein. A determination is then made as to whether the test agent restored function to the mis-folded protein, wherein an increase in biological function of the mis-folded protein indicates that the test agent is a pharmacoperone for the mutant protein. In particular examples, the mutant protein is expressed in a cell, and the cell is contacted with the test agent under conditions sufficient for the test agent to contact the mutant protein in the cell. For example, the mutant protein can be expressed naturally in the cell, or recombinantly expressed in the cell using standard molecular biology methods.

The protein of interest, for example, includes at least one mutation (such as one, two, three, at least two, or at least three mutations) that affects folding of the protein, routing of the protein to the cell membrane surface, aggregation of the protein, or combinations thereof. The assay includes determining whether the test agent restores function to the protein, wherein restoration of function indicates that the test agent is a pharmacoperone agent. Restoration of function does not require complete restoration of function to the mis-folded protein, and can include increases in biological function of for example at least 20%, at least 50%, at least 70%, or even at least 90%, as compared to an amount of biological function of a mutant protein not previously exposed to the test agent.

If the test agent alone cannot penetrate a cell surface membrane, it can be provided in a vehicle to permit transport of the test agent into the cell so that the test agent has access to the mis-folded protein. In particular examples, the test agent specifically binds to the protein of interest, but does not bind significantly to other proteins in the cell. In particular examples, a pharmacoperone that has specificity for the mis-folded protein of interest will at therapeutic amounts recognize and bind to the protein of interest, but will not bind to other cellular proteins. In some examples, the test agent has a binding affinity of 1 μM to 1 fM, for the protein of interest.

In particular examples, selecting a test agent includes selecting a test agent that has the desired activity at a concentration that does not significantly interfere with binding of a ligand to its receptor protein. In some examples, a test agent does not significantly interfere with a ligand binding to its receptor, if at the concentration needed for rescue of the misfolded receptor, the amount of ligand binding to its receptor does not decrease by more than 20%, such as no more than 10%, such as no more than 5%.

Ideally, a pharmacoperone agent identified using the disclosed methods has one or more of the following characteristics: high specificity for the mis-folded protein to be rescued (such as the ability to recognize and bind to the mis-folded protein and an inability to significantly bind to other proteins in the cell at therapeutic amounts), an ability to arrive at the correct cellular locus (for example, the ability to penetrate the cell membrane, traffic to the endoplasmic reticulum, and remain stable long enough to bind the mutant protein), and the ability to dissociate from the mutant protein (for example, to not compete with the physiological ligand) after it arrives at the appropriate target locus (such as the cell surface).

In some examples, the test agent is a peptidomimetic of a molecule that binds to the protein (such as a receptor). In specific examples, the agent is a non-peptide agent, such as an indole, macrolide (such as an erythromyocin macrolide), quinolone, or derivative or mimetic thereof. In particular examples, the agent is an agonist of the mis-folded protein (such as a ligand of a receptor). However, in examples where the mis-folded protein is a receptor, the test agent need not bind to the ligand binding site, and can instead bind with high specificity to another region of the receptor. In disclosed examples, the agent is not a generalized protein stabilization agent (such as trehalose, glycols, or dimethylsulfoxide) but instead exerts specific correcting of protein folding of the target protein.

In particular examples where the target protein of interest is a receptor, in some examples the test agent binds to the ligand binding site of the receptor. Such agents may stabilize the ligand binding site of a mutant receptor. For example, the test agent can be a non-antagonist of the receptor, such as an agonist of the receptor. In other examples, the test agent is an antagonist of the receptor and therefore may compete with the natural ligand of the receptor. In some examples where the test agent is an antagonist of the receptor, the test agent can have an inhibitory concentration ($IC_{50}$) of less than 1000 nM (for example less than 700 nM, less than 100 nM, less than 20 nM, less than 5 nM, less than 3 nM, less than 2.5 nM, or less than 2 nM). In still other examples, the test agent does not compete for the natural ligand binding site, and instead binds to a region of the receptor outside of the ligand binding site. Therapeutic agents that bind outside the natural ligand binding site of a receptor are not likely to interfere with subsequent activation of the receptor with an agonist.

In disclosed examples, the mutant protein is a mutant receptor that is mis-routed in the cell. In particular examples the receptor is a G-protein coupled receptor (GPCR) that includes one or more mutations that results in disease in a subject. For example, mutations in the cystic fibrosis transmembrane conductance regulator (CFTR) (such as ΔF508 CFTR) can cause cystic fibrosis. Mutations in the gonadotropin-releasing hormone receptor (GnRHR) (such as $N^{10}K$ mutation, a $T^{32}I$ mutation, an E90K mutation, a $Q^{106}R$ mutation, an $A^{129}D$ mutation, an $R^{139}H$ mutation, a $A^{171}T$ mutation, a $C^{200}Y$ mutation, an $R^{262}Q$ mutation, a $L^{266}R$ mutation, a $C^{279}Y$ mutation, a $Y^{284}C$ mutation, or combinations thereof) can cause hypogonadotropic hypogonadism (HH). Mutations in rhodopsin can result in retinitis pigmentosa. Mutations in alpha-1 antitrypsin can result in emphysema or alpha 1 antitrypsin deficiency liver disease.

However, one skilled in the art will appreciate that the mutant protein does not have to be a GPCR. The disclosed methods can be used to identify pharmacoperone agents specific for other proteins, such as other receptors, enzymes, or ion channels. For example, mutations in low-density lipoprotein (LDL) can cause familial hypercholesterolemia. Mutations in the aquaporin-2 or the arginine-vassopresin $V_2$ (AVP $V_2$) receptor can cause nephrogenic diabetes insipidus. Mutations in lens crystallins can cause cataracts. Mutations in the mitochondrial branched-chain alpha-ketoacid dehydrogenase (BCKD complex) can result in maple syrup urine disease. Mutations in Menkes protein can result in Menkes disease. Mutations in ataxin-3 can result in Machado-Joseph disease. Mutations in p53, pp60, ubiquitin-activating enzyme E1, or the glucocorticoid receptor can result in cancer. Mutations in amyloid precursor protein, presenilin 1, or presenilin 2 can result in Alzheimer's disease. Mutations in transthyretin can result in transthyretin amyloid disease. Mutations in prion protein can result in spongiform encephalopathies. Mutations in beta-glucosidase protein can result in Gaucher disease. Mutations in beta-galactosidase protein can result in beta-galactosidosis. Mutations in amyloid can result in Creutzfeldt-Jakob disease. Mutations in alpha-synclein, Parkin, or ubiquitin C can result in Parkinson's disease. Mutations in hemoglobin can result in sickle cell anemia. Mutations in amyloid fibrils can cause systemic amyloidosis. Mutations in the insulin receptor can cause diabetes.

In a particular example, the protein is a human GnRHR protein that includes one or more of the following mutations in a human GnRHR amino acid sequence: an $N^{10}K$ mutation, a $T^{32}I$ mutation, an $E^{90}K$ mutation, a $Q^{106}R$ mutation, an $A^{129}D$ mutation, an $R^{139}H$ mutation, a $A^{177}T$ mutation, a $C^{200}Y$ mutation, an $R^{262}Q$ mutation, a $L^{266}R$ mutation, a $C^{279}Y$ mutation, or a $Y^{284}C$ mutation. In a specific example, the protein is a human GnRHR protein that includes a $Q^{106}R$/$L^{266}R$ mutation, $A^{171}$ $T/Q^{106}R$ mutation, a $L^{314}X_{(stop)}/Q^{106}R$ mutation, a $T^{32}I/C^{200}Y$ mutation, a $R^{262}Q/A^{129}D$ mutation, a $R^{262}Q/Q^{106}R$ mutation, a $N^{10}Q/Q^{106}R$ mutation, or a $R^{262}Q/Y^{214}C$ mutation. In some examples, the protein is a human GnRHR protein that includes an $E^{90}K$ mutation.

The method used to determine whether the test agent has the ability to restore function to the mutant protein may depend on the mutant protein of interest. For example, the method used can depend on the function of the protein, on the location of the protein in the cell, and other parameters. Particular methods that can be used include, but are not limited to: determining an amount of production of an intracellular marker of protein function (such as production of inositol phosphate (IP) by a GPCR), determining an amount of binding of a molecule (such as an antibody, ligand, agonist, or antagonist) specific for the protein of interest, determining an amount of surface-bound antibody-, ligand-, agonist-, or antagonist-mutant protein complex internalized, or combinations thereof.

The assay can further include identifying a specific mutation in the mis-folded protein that adversely affects protein function, wherein selecting the test agent includes selecting an agent that has an effect against the specific mutation.

Also provided by the present disclosure are methods of treating a subject having a disease resulting from a mutant protein that is mis-folded, mis-routed in the cell, aggregated, or combinations thereof. The method includes identifying, detecting, or determining the mutations present in the protein, wherein the presence of a particular mutation indicates that the subject can be treated with a pharmacoperone specific for the mis-folded or mis-routed mutant protein. It has been determined that particular mutations are more susceptible to treatment with a pharmacoperone, while other mutations are not. Subjects having the particular mutation(s) susceptible to treatment with a pharmacoperone are administered a therapeutically effective amount of the pharmacoperone. In other examples, a pharmacoperone is chosen that is particularly beneficial for subjects having that specific mutation. In some examples following administration of the pharmacoperone, the subject is administered an agonist of the receptor to activate the rescued receptor.

It has also been determined that some mutant mis-folded proteins have a dominant negative effect on the biological function of the corresponding wild-type protein. Based on this information, methods are provided for predicting or determining the severity of the disease resulting from the mutant protein. The method includes identifying, detecting, or determining the mutations present in the protein, wherein the presence of a particular mutation indicates the severity of the disease. Based on this information, one can determine the appropriate treatment protocol for the subject.

In some examples, the pharmacoperone administered is selected using the assay described above. In some examples, the pharmacoperone does not bind to a ligand binding site of the receptor protein of interest. In yet other examples, the pharmacoperone is an agonist of the receptor. In certain examples where the pharmacoperone administered to the subject is an antagonist of the receptor protein, the receptor is not a V2 vasopressin receptor or a histamine-H2 receptor.

In particular examples, the pharmacoperone is administered to the subject, followed by a period when the pharmacoperone is not administered to the subject, and then a period during which the pharmacoperone is again administered to the subject. In some examples, the period when the pharmacoperone is not administered to the subject is at least 2 hours.

Examples of subjects that can be treated with a pharmacoperone include, but are not limited to, subjects having cystic fibrosis, nephrogenic diabetes insipidus, familial hypercholesterolemia, cataracts, Alzheimer's, retinitis pigmentosa, hypogonadism, or hypogonadotropic hypogonadism (HH). In a particular example, the subject has HH and at least one of the following mutations in their GnRHR amino acid sequence: a $N^{10}K$ mutation, a $T^{32}I$ mutation, an $E^{90}K$ mutation, a $Q^{106}R$ mutation, an $A^{129}D$ mutation, an $R^{139}H$ mutation, a $A^{171}T$ mutation, a $C^{200}Y$ mutation, an $R^{262}Q$ mutation, a $L^{266}R$ mutation, a $C^{279}Y$ mutation, a $Y^{284}C$ mutation, or combinations thereof.

Pharmacoperone agents identified using the disclosed methods can also be used to increase expression of wild-type protein (such as a receptor).

BRIEF DESCRIPTION OF THE DRAWINGS

FIG. 4 is a bar graph showing the effect of 1 μg/ml of three indoles in restoring function to each GnRHR mutant. IP production in the presence of $10^{-7}$ M buserelin is shown. For clarity in the SEM bars were omitted. The standard deviation was typically less than 10% of the corresponding mean.

DETAILED DESCRIPTION OF SEVERAL EMBODIMENTS

Abbreviations and Terms

Figure 1A:
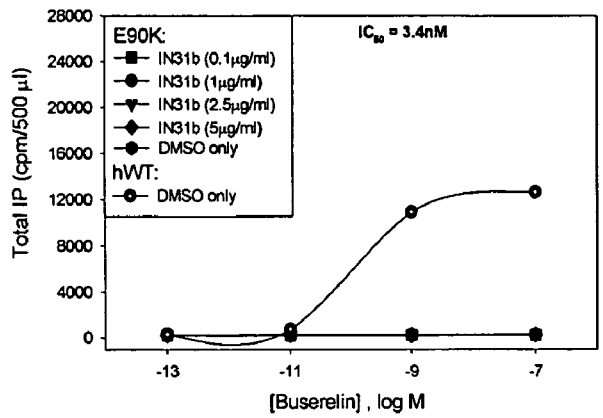
FIGS. 1A-C are graphs showing the efficacy (assessed by IP production) of indoles, (A) IN31b, (B) IN3, and (C) IN30 on restoration of function to the GnRHR mutant $E^{90}K$.

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "a mutant protein" includes a plurality of such proteins and reference to "the receptor" includes reference to one or more receptors and equivalents thereof known to those skilled in the art, and so forth. Similarly, the word "or" is intended to include "and" unless the context clearly indicates otherwise. Hence "comprising A or B" means including A, or B, or A and B.

Unless explained otherwise, all technical and scientific terms used herein have the same meaning as commonly understood to one of ordinary skill in the art to which this disclosure belongs. In case of any conflict between these explanations and those provided in an incorporated document, these explanations control.

Agonist: Any agent that is capable of combining with a receptor an initiating a reaction or activity. In a particular example, an agonist is a receptor agonist that can bind to its receptor and initiate the physiological and pharmacological responses characteristic of the receptor. Examples of agonists include native ligands as well as other agents that can mimic the action of the ligand on the receptor.

Analog: An agent (such as an organic chemical compound) that is structurally similar to another, but differs slightly in composition, for example the replacement of one atom by an atom of a different element or functional group. For example, an analog of In3, ((2S)-2-[5-[2-(2azabicyclo[2.2.2]oct-2-yl)-1,1-dimethyl-2-oxoethyl]-2-(3,5-dimethylphenyl)-1H-indol-3-yl]-N-(2pyridin-4-ylethyl)propan-1-amine, is structurally similar to In3, and has a similar effect on restoring function to a GnRHR mutant such as $E^{90}K$.

Antagonist: An agent that binds to the ligand-binding site of a receptor and interferes with binding of a ligand or agonist to the receptor ligand binding site, thereby resulting in decreased receptor-associated responses normally induced by the ligand or agonist.

The inhibitory activity of an antagonist for a receptor is represented as an inhibitory concentration ($IC_{50}$), wherein better inhibitors have lower $IC_{50}$ values. Antagonism can be competitive and reversible (it binds reversibly to a region of the receptor in common with the agonist.) or competitive and irreversible (antagonist binds covalently to the agonist binding site, and no amount of agonist can overcome the inhibition).

Binding: A specific interaction between two molecules, such that the two molecules interact. For example, binding can occur between a pharmacoperone and a particular misfolded mutant proteins, and between a receptor and a particular ligand. Binding can be specific and selective, so that one molecule is bound preferentially when compared to another molecule. In one example, specific binding is identified by a disassociation constant ($K_d$) of an agent for a particular protein or class of proteins, compared to the $K_d$ for one or more other cellular proteins. In another example, specific binding of an antagonist for a receptor is identified by an inhibitory concentration ($IC_{50}$).

G protein-coupled receptor (GPCR): A superfamily of proteins characterized by seven transmembrane alpha-helices that signal through interaction with a family of heterotrimeric GTP-binding proteins, referred to as G proteins. Examples include, but are not limited to, beta-adrenergic receptor (betaAR), cystic fibrosis transmembrane conductance regulator (CFTR), gonadotropin-releasing hormone receptor (GnRHR), and rhodopsin.

There are at least seven GPCR families (A, B, large N-terminal family B-7 transmembrane helix, C, Frizzled/Smoothened, taste 2, and vomeronasal 1 receptors). Exemplary Family members A include, but are not limited to, GnRHR, rhodopsin, and CC chemokine receptors 1-10. Exemplary Family B members include, but are not limited to, calcitonin receptor, glucagon receptor, and parathyroid hormone receptor. Exemplary Family C members include, but are not limited to, GABA-B receptor metabotropic glutamate receptors, the calcium sensing receptor, and a number of pheromone receptors.

Gonadotropin releasing hormone receptor (GnRHR): GnRH receptors belong to the family of G protein-coupled receptor proteins and have been localized to the anterior pituitary, brain, placenta, and reproductive organs as well as tumor tissues. In humans, after GnRH ligand binding, the activated GnRHR-$G_{q/11}$ protein complex activates the membrane-associated enzyme phospholipase Cp, leading to inositol 1,4,5-trisphosphate (IP) production and the release of intracellular calcium.

Figure 11:
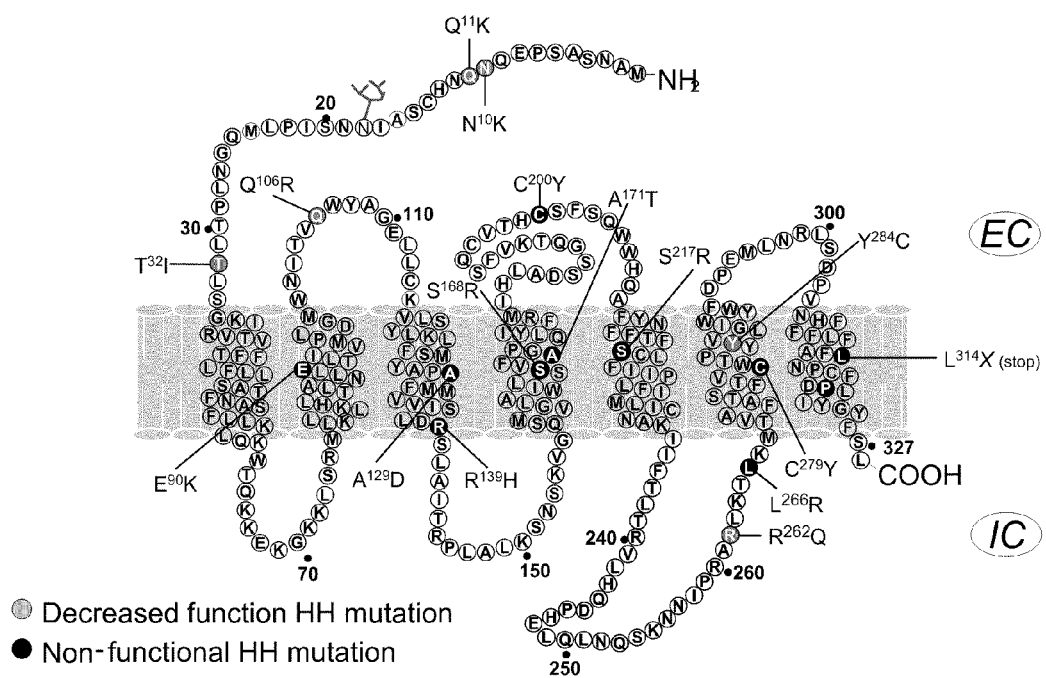
FIG. 11 is a schematic diagram showing the human GnRHR amino acid sequence (SEQ ID NO: 1) and location of the inactivating mutations identified to date (black and gray circles). EC, extracellular space; IC, intracellular space.

The term GnRHR includes any GnRHR gene, cDNA, RNA, or protein from any organism and includes a GnRHR that can normally traffic to the cell surface and bind GnRH. Examples of wild-type GnRHR nucleic acid sequences include, but are not limited to, GenBank Accession No. AF001950 (human cDNA) and GenBank Accession No. S59525 (rat mRNA). Examples of GnRHR amino acid sequences include, but are not limited to: GenBank Accession Nos: AAB71348 (human, also see FIG. 11 showing amino acid residues mutated in subjects having HH) and AAB2642 (rat). In one example, a GnRHR sequence includes a full-length wild-type (or native) sequence, as well as GnRHR allelic variants, variants, fragments, homologs or fusion sequences that retain wild-type function. All Genbank Accession Nos referred to herein are incorporated by reference.

GnRHR agonist: Agents that can bind to GnRHR and initiate the physiological and pharmacological responses characteristic of GnRHR. Examples include native GnRHR ligands, such as GnRH, as well as other agents that can mimic the action of GnRH. Particular examples include buserelin (D-tert-butyl-$Ser^6$, des-$Gly^{10}$, $Pro^9$, ethylamide-GnRH) and leuprolide (D-$Leu^6$, $Pro^9$, des-$Gly^{10}$-ethylamide-GnRH).

GnRHR antagonist: Agents that bind to the ligand-binding site of GnRHR and interfere with binding of a GnRHR ligand or GnRHR agonist to the GnRHR binding site, thereby resulting in decreased GnRHR-associated responses normally induced by the GnRHR ligand or GnRHR agonist.

GnRHR ligand: Agents that can bind to the ligand-binding site of GnRHR. In some examples, such agents bind reversibly. The native GnRHR ligand is GnRH. Includes GnRHR agonists that bind at the GnRHR ligand-binding site.

Hypogonadism: An underactivity of the gonads. In men, hypogonadism is a condition that occurs when the testicles do not produce enough testosterone. In women, hypogonadism is a condition that occurs when the ovaries do not produce enough estrogen. Primary hypogonadism occurs when there is a problem with the testicles/ovaries themselves. Secondary hypogonadism occurs when there is a problem with the pituitary gland. One example of secondary hypogonadism is hypogonadotropic hypogonadism.

Symptoms associated with hypogonadism include: erectile dysfunction in men (the inability to achieve or maintain an erection), infertility, decreased sex drive, decrease in beard and growth of body hair, decrease in size or firmness of the testicles, decrease in muscle mass and increase in body fat, enlarged male breast tissue, hot flashes, mood swings, irritability, depression, fatigue, osteoporosis (decreased bone density), delayed puberty, and combinations thereof.

There are several causes of hypogonadism, including: Klinefelter's syndrome, undescended testicles, hemochromatosis, testicular trauma, cancer treatment such as chemotherapy or radiation therapy, normal aging (older men and women generally have lower levels of testosterone and estrogen, respectively, although the decline of the hormone varies greatly among people), pituitary disorders, medications including psychiatric drugs and agents used to treat heartburn and gastroesophageal reflux disease, and genetic mutations.

Currently available treatments include male or female hormone replacement (testosterone replacement therapy (TRT) and hormone replacement therapy (HRT), respectively), which can include administration of androgens such as testosterone and estrogen. Pituitary hormones, such as GnRH, can also help increase testosterone and estrogen levels. The present disclosure provides additional methods that can be used to treat hypogonadism, such as administration of agents that restore function to mutant GnRHR, and administration of agents that increase the presence of wild-type GnRHR on the cell surface.

Particular examples of hypogonadism include hypotestosteronism (a disorder characterized by lower than normal plasma levels of testosterone) and hypoestrogeneism (a disorder characterized by lower than normal plasma levels of estrogen).

Hypogonadotropic hypogonadism (HH): A congenital disorder characterized by failure of gonadal function secondary to deficient gonadotropin secretion, resulting from either a pituitary or hypothalamic defect, and is commonly seen in association with structural lesions or functional defects affecting this region. HH is characterized by delayed sexual development and by inappropriately low or apulsatile gonadotropin and sex steroid levels in the absence of anatomical or functional abnormalities of the hypothalamic-pituitary axis. This disorder is genetically heterogeneous and can be sporadic or familial (X-linked or autosomal). At least 14 mutations of the GnRHR are associated with HH.

Indole (2,3-benzopyrrole): A heterocyclic compound having the chemical formula $C_8H_7N$, and derivatives thereof, such as In30, ((2S)-2-[5-[2-(2-azabicyclo[2.2.2]oct-2-yl)-1,1-dimethyl-2-oxoethyl]-2-(3,5-dimethylphenyl)-1H-indol-3-yl]-N-{2-[4-(methylsulfinyl)phenyl]ethyl}propan-1-amine); In31b, ((2S)-N-[2-(4-carboxyphenyl)ethyl]-2-[5-[1,1-dimethyl-2-(4-methylpiperazin-1-yl)-2-oxoethyl]-2-(3,5-dimethylphenyl)-1H-indol-3yl]propan-1-aminium trifluoroacetate); and In3, ((2S)-2-[5-[2-(2-azabicyclo[2.2.2]oct-2-yl)-1,1dimethyl-2-oxoethyl]-2-(3,5-dimethylphenyl)-1H-indol-3-yl]-N-(2-pyridin-4-ylethyl)propan-1-amine. Exemplary indole antibiotics are disclosed in U.S. Pat. Nos. 6,486,192; 5,380,723; and 4,076,831, all herein incorporated by reference. In a particular example, an indole includes indole-derivatives that have an $IC_{50}$ of about less than 3 nM for hGnRHR.

Inhibitory concentration ($IC_{50}$): An inhibitory concentration is a concentration that inhibits an effect (such as a receptor-mediated effect). The amount of inhibitory agent needed to reduce an effect by 50% is an $IC_{50}$. In one example, the $IC_{50}$ of a GnRHR antagonist is the concentration of antagonist needed to reduce an amount of ligand binding (such as GnRH) to the receptor by 50%, compared to an amount of ligand binding in the absence of the antagonist. Lower $IC_{50}$ values suggest better inhibition.

Inositol phosphate (IP): Includes all phosphorylated states of inositol, such as inositol-1-phosphate ($IP_1$), inositol-4,5-diphosphate ($IP_2$), inositol-1,4,5-triphosphate ($IP_3$), and inositol-1,3,4,5-triphosphate ($IP_4$). In one example, IPs are produced following activation of a GCPR, such as GnRHR Label: An agent capable of detection, for example by ELISA, spectrophotometry, flow cytometry, or microscopy. For example, a label can be attached to a molecule (such as an antibody), thereby permitting detection of the molecule. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Ligand: A molecule that binds to another molecule. In one example, a ligand is a molecule, such as a hormone or neurotransmitter, which specifically binds to a receptor. The region of the receptor that specifically binds to the ligand is referred to as the ligand binding site of the receptor.

Macrolide: Any of a large group of antibiotics containing a macrolide ring linked glycosidically to one or more sugars. Members of the macrolide antibiotic group include erythromycin, carbomycin, azithromycin, and clarithromycin, and derivates thereof. Examples of particular erythromycin-derived macrolides include A-7662.0, (Erythromycin A); A-64755.0 (11-deoxy-11-[carboxy-phenylethylamino]-6-O-methyl-erythromycin A 11,12-(cyclic carbamate)); A-177775.0, (3'-N-desmethyl-3'-N-cyclopentyl-11-deoxy-11-[carboxy-(3,4-dichlorophenylethylamino)]-6-O-methyl-erythromycin A 11,12-(cyclic carbamate)); and A-222509.0, 3',3'-N-desmethyl-3',3'-N-cyclopropylmethyl-11-deoxy-11-[carboxy-(3-chloro,4-fluoro-phenylethylamino)]-6-O-methyl-erythromycin A 11,12-(cyclic carbamate)). Additional macrolide antibiotics are disclosed in U.S. Pat. Nos. 5,786,338; 5,169,956; and 4,374,764, all herein incorporated by reference. In a particular example, a macrolide includes macrolide-derivatives that have an $IC_{50}$ of about less than 700 nM for hGnRHR.

Mammal: This term includes both human and non-human mammals. Similarly, the terms "patient," "subject," and "individual" includes living multicellular vertebrate organisms, such as human and veterinary subjects.

Mimetic: A molecule (such as an organic chemical compound) that mimics the activity of an agent, such as the activity of a pharmacoperone agent on trafficking of a mis-folded mutant receptor to the cell surface. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific activity. For computer modeling applications, a pharmacophore is an idealized, three-dimensional definition of the structural requirements for biological activity. Peptido- and organomimetics can be designed to fit each pharmacophore with computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and Principles of Pharmacology (ed. Munson, 1995), chapter 102 for a description of techniques used in computer assisted drug design.

Mis-folded mutant protein: A protein having at least one amino acid mutation (such as at least one substitution, deletion, insertion, or combinations thereof) compared to the corresponding wild-type protein sequence, wherein the mutation(s) results in the improper folding of the mutant protein. In some examples, improper folding results in aggregation of the mutant protein or improper localization and trafficking of the mutant protein in the cell.

Mutant GnRHR: A GnRHR sequence that includes at least one amino acid substitution or deletion compared to a wild-type sequence, which results in the development of HH in a subject. Examples of mutant GnRHR include, but are not limited to, those GnRHR sequences that include one or more of the following mutations: $N^{10}K$, $T^{32}I$, $E^{90}K$, $Q^{106}R$, $A^{129}D$, $R^{139}H$, $A^{171}T$, $C^{200}Y$, $R^{262}Q$, $L^{266}R$, $C^{279}y$, $Y^{284}C$, $L^{314}X_{stop}$, $A^{171}T$, $Q^{11}K$, $P^{320}L$, and a splice junction mutation at the intron 1-exon 2 boundary in the human GnRHR sequence, as well as rat des325-327, desL237-L241 and $C^{278}A$ mutations. In a particular example, mutant GnRHR does not include a human $S^{168}R$ or $S^{217}R$ mutation, or the rat des260-65-GnRHR or $C^{229}A$ mutation.

Mutant sequence: A protein or nucleic acid sequence containing one or more substitutions, deletions, or insertions as compared to a corresponding wild type sequence. In some examples, one or more mutations in a protein or nucleic acid sequence can result in mis-folding of the protein. Such mis-folding can cause disease in a subject. For example, a mutation in GnRHR can cause HH.

Penetrate a cell membrane: An ability to pass through the external plasma membrane of the cell, for example, the ability of an agent to pass from the outside of a cell to the inside of the cell.

Peptidomimetic: A compound containing non-peptide structural elements that is capable of mimicking the biological activity of a protein. In particular examples, a peptidomimetic contains non-peptidic structural elements and does not have classical peptide characteristics such as enzymatically scissile peptidic bonds. Such compounds can be agonists or antagonists.

Peripheral administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Pharmacoperone agent: A pharmacological agent that can correct errors in protein folding, thereby restoring biological activity to a mis-folded mutant protein. The resulting restructuring of the mutant protein can decrease aggregation of mutant proteins and can result in correct routing of the mutant protein in a cell, thereby leading to a normal pattern of cellular localization and function. Biological activity need not be completely restored; increases of at least 20%, at least 50%, at least 75%, or even at least 80% are considered restored. In some examples, pharmacoperones can arrest or reverse disease states by inducing mutant proteins to adopt a native-like conformation instead of an improperly folded conformation.

In some examples, it is believed that pharmacoperones stabilize a specific conformation of the misfolded protein, reduce aggregation, prevent nonproductive interactions with other resident proteins, or modify the activity of endogenous chaperones. Such effects increase the efficiency of ER export and promote the proper trafficking of the mutant protein to its correct destination, such as the plasma membrane.

Quinolone: A heterocyclic compound having the chemical formula $C_9H_7N$, and derivatives thereof, such as Q89, (7-chloro-2-oxo-4-{2-[(2S)-piperidin-2-yl]ethoxy}-N-pyrimidin-4-yl-3-(3,4,5trimethylphenyl)-1,2-dihydroquinoline-6-carboxamide); Q76, (N-(7-chloro-3-(3,5-dimethylphenyl)-2-oxo-4-{2-[(2S)-piperidin-2-yl]ethoxy}-1,2-dihydroquinolin-6-yl)-N'-cyclopropylurea); and Q08, ((2S)-2-(2-{[7-chloro-6-[(6,7-dimethoxy-3,4-dihydroisoquinolin-2(1H)-yl)carbonyl]-3-(3,5-dimethylphenyl)-2-oxo-1,2-dihydroquinolin-4-yl]oxy}ethyl)piperidinium trifluoroacetate). Includes synthetic antibacterial agents (quinolone antibiotics) such as nalidixic acid, cinoxacin, rosoxacin, and the fluorinated 4-q's. Additional quinolone antibiotics are disclosed in U.S. Pat. Nos. 5,990,122; 5,646,163; and 5,385,906, all herein incorporated by reference. In a particular example, a quinolone includes quinolone-derivatives that have an $IC_{50}$ of about less than 3 nM for hGnRHR.

Receptor: A protein within a cell or on the surface characterized by selective binding of a particular agent and a specific physiologic effect that accompanies the binding. Exemplary receptors include cell surface receptors (such as those that can specifically bind to a particular peptide hormone, neurotransmitter, antigen, or immunoglobulin) and cytoplasmic receptors. Particular examples of a class of receptors are the GCPRs.

Restore function: An agent, such as a pharmacoperone agent, is said to restore function to a mutant protein (such as a mutant receptor) when contact of the agent with a mutant protein results in increased biological activity of the mutant protein, as compared to an amount of biological activity of a mutant protein not previously contacted with the agent. Restoring function to a mutant protein does not require restoration of 100% of wild-type activity. For example, an increase in biological activity of at least 25% when compared to no treatment with the agent indicates that the agent can restore activity to the mutant protein.

In one example, increasing activity of a mutant protein increases binding of a mutant protein to a molecule specific for the protein (such as increased binding of a ligand to its receptor), as compared to binding in the absence of the agent. For example, binding of a protein-specific molecule to the corresponding mutant protein having restored function increases at least 25% when compared to binding in the absence of the agent, such as increases of at least 50%, at least 60%, at least 75%, at least 80%, at least 90%, at least 100%, or even at least 200%. Such binding can be performed using the methods disclosed herein (for example, see Example 1).

In another or in an additional example, an agent is said to restore function to a mutant protein when contact of the agent with a mutant protein results in an increase in production of an intracellular marker of protein function (such as increased production of IP by a mutant GCPR in the presence of the agent), as compared to production in the absence of the agent. For example, production of an intracellular marker of protein function by a mutant protein having restored function increases at least 25% when compared to production by a mutant protein in the absence of the agent, such as increases of at least 50%, at least 60%, at least 75%, at least 80%, at least 90%, at least 100%, at least 200%, or even at least 500%. Determining an amount of production of an intracellular marker of protein function can be performed using the methods disclosed herein (for example, see Example 1).

In another or in an additional example, an agent is said to restore function to a mutant protein when contact of the agent with a mutant protein results in increased internalization of complexes that include surface proteins bound to a molecule specific for the protein, as compared to an amount of complex internalized in the absence of the agent. For example, an amount of complex internalized by a mutant protein having restored function increases at least 25% when compared to an amount of complex internalized by a mutant protein in the absence of the agent, such as increases of at least 50%, at least 60%, at least 75%, at least 80%, at least 90%, at least 100%, or even at least 200%. Determination of an amount of complex internalized can be performed using the methods disclosed herein (for example, see Example 2).

Sample: Biological samples such as samples containing nucleic acid molecules (such as genomic DNA, cDNA, RNA, or mRNA) or proteins. Exemplary samples are those containing cells of a subject, such as those present in peripheral blood, urine, saliva, tissue biopsy, surgical specimen, fine needle aspirates, amniocentesis samples and autopsy material.

Subject: Living multicellular vertebrate organisms. Includes human and veterinary subjects, such as mammals, rodents, and birds.

Test agent: Any polypeptide, organic compound, inorganic compound, or other molecule of interest. In particular examples, a test agent can permeate a cell membrane (alone or in the presence of a carrier).

Therapeutically effective amount: An amount of an agent (alone or in combination with other therapeutically effective agents) sufficient to achieve a desired biological effect, for example an amount that is effective to increase binding of an agonist to a mutant protein (such as binding of a ligand to its receptor) by at least a desired amount, increasing production of an intracellular marker of protein function by at least a desired amount, increasing surface-bound mutant receptor-ligand complex internalized by at least a desired amount, or combinations thereof, such as in the cell of a subject to whom it is administered.

In a particular example, it is an amount of a pharmacoperone agent effective to increase binding of an agonist to a mutant protein by at least a desired amount, such as an increase by at least 25%, at least 50%, at least 75%, at least 20%, or even at least 200% as compared to an amount of binding prior to treatment. In other or additional examples, it is an amount effective to increase production of an intracellular marker of protein function by at least a desired amount, such as increase by at least 25%, at least 50%, at least 75%, at least 20%, or even at least 200% as compared to an amount of production prior to treatment. In other or additional examples, it is an amount effective to increase surface-bound mutant receptor-ligand complex internalized by at least a desired amount, such as increase by at least 25%, at least 50%, at least 75%, at least 20%, or even at least 200% as compared to an amount of complex internalized prior to treatment.

In some examples, it is an amount of a pharmacoperone agent (alone or in combination with other therapeutically effective agents) that can restore function to a mutant protein that can improve signs or symptoms of a disease caused by the mutation. In other examples, it is an amount of an agent (alone or in combination with other therapeutically effective agents) that can increase an amount of wild-type receptor at the cell surface, for example by at least 10%, at least 20%, or even at least 50% as compared to the absence of the pharmacoperone agent. In particular examples, a therapeutically effective amount improves signs or symptoms of hypogonadism, for example such a condition associated with decreased functional GnRHR at the cell surface.

An effective amount of a pharmacoperone agent that restores function to a mutant protein can be administered in a single dose, or in several doses (for example daily, weekly, or monthly) during a course of treatment. However, the effective amount of agent may be dependent on the source of agent administered, the subject being treated, the severity and type of disease being treated, and the manner of administration. For example, a therapeutically effective amount of a pharmacoperone agent that restores function to a mutant protein can vary from about 1 µg/kg body weight to about 20 µg/kg body weight per dose, about 1 µg/kg body weight to about 10 µg/kg body weight per dose, about 10 µg/kg body weight to about 20 µg/kg body weight per dose, or about 1-2 µg agent/kg body weight/dose. In some examples, the pharmacoperone agent is administered, followed by a period where no pharmacoperone agent is administered (such as at least one day, at least 2 days, at least 7 days, at least 14 days or even at least 30 days), followed by another administration of the pharmacoperone agent. In particular examples, a therapeutically effective amount of a pharmacoperone agent peaks in the serum, then returns to negligible levels indicating that the agent has been removed from the rescued protein.

To assess restoration of mutant protein function, or increased expression of wild-type receptor at the cell surface, the methods disclosed herein can be used to compare a subject before and after treatment. For example, binding of an agonist to a mutant protein, production of an intracellular marker of protein function, and the surface-bound mutant receptor-ligand complex internalized can be determined using the methods described below.

Translocation: The transport of an agent, such as a protein, from one part of a cell to another part of the cell. In one example, it includes the transport of a wild-type or mutant receptor to the cell membrane.

All of the examples provided herein are non-limiting examples provided merely for illustration and not limitation.

Identification of Agents that Restore Function to Mutant Proteins

Provided herein are assays that permit detection, selection, or identification of one or more pharmacoperone agents for their ability to restore function to a mutant protein containing at least one amino acid mutation (such as a substitution, deletion, insertion, or combinations thereof) that results in mis-folding of the protein and reduced biological activity of the protein. Such mis-folding can result in improper cellular trafficking, localization, aggregation, or combinations thereof, and cause disease. In particular examples, the protein is a mutant receptor, such as a mutant G-protein coupled receptor (for example mutant GnRHR). In other examples, the protein is a mutant ion channel or a mutant enzyme. However, this disclosure is not limited to particular mutant proteins that are mis-folded. Administration of pharmacoperones to a subject at a therapeutically effective dose can therefore be used to treat diseases that result from mis-folded proteins.

The assay includes determining whether the test agent restores function to the mis-folded protein, wherein restoration of function indicates that the test agent is a pharmacoperone agent. Restoration of function does not require 100% restoration of the biological function of the native protein. Instead, restoration or rescue of function of a mis-folded protein includes increases in biological function of at least 20%, at least 50%, at least 70%, or even at least 90%, as compared to an amount of biological function of the mutant protein in the absence of the test agent (that is, a mutant protein that has not previously been contacted with the test agent). In particular examples, a test agent is said to rescue a mis-folded mutant protein if the percentage of properly folded proteins increases by at least 20%, for example at least 50%, or even at least 75%.

Generally, the assay includes screening a test agent (such as a plurality of test agents) for ability to restore functionality to a mutant protein that results in mis-folding of the protein. Test agents can penetrate through the outer cell membrane to reach the inside of the cell, and recognize and bind to the mutant protein with high specificity. In particular examples, a test agent has high specificity for the mutant protein if it can bind to the mutant protein at a therapeutic concentration with a binding affinity (also referred to as the dissociation constant or Kd) of no more than 1 µM, such as no more than 1 nM, no more than 1 µpM, no more than 1 µfM, for example a Kd of 1 µM-1 fM, but not bind significantly to other proteins in the cells (such as a Kd of greater than 1 μM for other proteins, such as 1 mM). However, a test agent may have a high specificity for classes of proteins, such as GPCRs, such that the test agent can bind to two or more different mutant GPCRs at a therapeutic concentration with a Kd of no more than 1 μM, but not bind significantly to non-GPCRs (such as a Kd of greater than 1 μM). In particular examples, the ratio of the Kd of the test agent for the mutant protein to another cellular protein is no more than 1:2, such as no more than 1:3, such as no more than 1:5.

The assay includes contacting the test agent with the mutant protein under conditions that allow interaction between the test agent and the mutant protein and that permit restoration of function to the mutant protein. Subsequently, a determination is made as to whether functionality was restored to the mutant protein. Test agents that restore functionality are considered to be pharmacoperones of the mutant protein, and can be selected for further study.

In some examples, the method includes determining an amount of specificity the test agent has for the protein, and not selecting those test agents that generally bind to many proteins in the cell. Methods known in the art can be used to determine the binding specificity of a test agent for the protein of interest. In one example, the Kd of the test agent for the protein of interest and for at least one other protein (such as at least two, at least five, or at least 10 other proteins) is determined. Particular examples of methods for determining dissociation rate are described in U.S. Pat. No. 6,720,190, herein by reference in its entirety. Test agents having a Kd of less than 1 μM for the protein of interest, and a Kd of greater than 1 μM are selected for further study, as this indicates that the test agent has a high specificity for the protein of interest. In contrast, test agents having a Kd of less than 1 μM for the protein of interest and for one or more other proteins, would not be selected as this indicates that the test agent generally binds no-specifically to many proteins, and does not have high specificity for the protein of interest.

In particular examples, the test agent has an ability to dissociate from the protein, and therefore, in some examples the method can further include determining an ability of the test agent to dissociate from the protein, and for example selecting those test agents that can dissociate from the protein for further study. For example, $K_{off}$ (dissociation rate) can be determined using methods known in the art. In one particular example, $K_{off}$ is determined by determining the "off rate" for test agent dissociating from the protein. Briefly, the test agent (such as a labeled test agent) is allowed to bind to the protein (such as a receptor), for example to equilibrium. Further binding of the test agent is terminated (for example by removing unbound test agent or adding a concentration of an unlabeled test agent sufficient to permit binding to nearly all the unoccupied proteins and thus block binding of the labeled test agent) to permit determining the rate of dissociation. Subsequently, the amount of binding of the test agent to the protein is determined at various times to determine how rapidly the test agent falls off the protein. For example, this can be determined by measuring a decrease in signal from the label on the test agent over time. In particular examples, the test agent has a $K_{off}$ of at least 0.05 $min^{-1}$, for example at least 0.1 $min^{-1}$, at least 0.3 $min^{-1}$, at least 0.5 $min^{-1}$, at least 1 $min^{-1}$, such as 0.1 $min^{-1}$ to 1 $min^{-1}$.

In yet other examples, the test agent has an ability to not compete with binding of a ligand the protein, and therefore, in some examples the method can further include determining an ability of the test agent to bind to the ligand binding site of the protein, and for example selecting those test agents that do not significantly bind to the ligand binding site for further study. Such methods are known in the art. In one example, a therapeutic amount of a test agent is contacted with the protein of interest, and a determination made as to whether the test agent activated or inhibited the biological activity of the receptor. Test agents that do not activate or inhibit receptor activity, do not bind with high affinity to the ligand binding site, and therefore do not significantly compete with binding of a ligand. In other example, a therapeutic amount of a test agent is contacted with the protein of interest and its ligand, and a determination made as to whether the test agent changed the ability (such as decreased) of the ligand to stimulate the biological activity of the receptor. For example, if the biological activity is not significantly altered in the presence of the test agent, this indicates that the test agent does not significantly interfere with binding of the ligand to its receptor, or compete with the ligand for binding to the receptor.

Methods for determining the ability of the test agent to penetrate the cell membrane to permit entry of the test agent into the cell are known in the art. For example, the hydrophobic character of the test agent can be determined. Agents that are hydrophobic are likely to be able to penetrate the cell membrane, and therefore can be selected for further study. Other methods include contacting the test agent with the cell, for example at 37° C., and determining the amount of test agent internalized into the cell at various time points. For example, the test agent can include a label, and the relative amount of label inside the cell determined, for example over a period of time.

In other example, following incubating the test agent with the cell, excess test agent is removed, the cells lysed, and the amount of test agent recovered from the cell determined. The mis-folded protein of interest can be expressed recombinantly in the cell using standard molecular biology methods. Alternatively, a cell that naturally expresses the mis-folded protein can also be used. In particular examples, the cell expressing the mis-folded protein is exposed to the test agent for an amount of time sufficient for the test agent to penetrate the cell membrane, contact the mis-folded protein, and allow the mis-folded protein to be properly folded (and in some examples trafficked to the native location in the cell). In other examples, the mis-folded protein is contacted with one or more test agents in vitro, and a determination made as to whether the protein is properly folded in the presence of the test agent (or following incubation with the test agent).

The method can include contacting more than one cell with the test agent (such as at least two, at least 10, at least 100, or even at least 1000 cells). In particular examples, at least two of the cells each express a different mutant protein (such as a protein with two different mutations [for example protein A with mutation 1 and mutation 2], or two different proteins [for example protein A with mutation 1 and protein B with mutation 2]). For example, the cells can express different hGnRHR mutations. As a control, cells not expressing the mutant protein, or a cell expressing a wild-type version of the protein can be used. Any cell that can express the protein of interest can be used. In particular examples, the cell is a mammalian cell, such as a human cell. Cells can be primary cells, or tissue culture cells, for example.

Based on the results provided herein, a model is proposed whereby chemically distinct agents (referred to herein as pharmacoperones) serve as molecular scaffolding, allowing mutant mis-folded proteins to fold correctly. The correctly folded protein can then be properly routed in the cell (or if the mis-folding results in aggregation, aggregation will decrease). For example, if the mutant protein is a mis-folded receptor that normally resides in the plasma membrane, pharmacoperones permit proper folding of the mutant receptors, thereby allowing the mutant receptor to traffic to the cell membrane and be available for ligand binding. Mis-folded mutants are good candidates for rescue by pharmacological chaperones that act as molecular scaffolding, promoting proper folding, maturation and correct targeting of the mutants from the endoplasmic reticulum to the cell surface. However, some mis-folded mutant proteins will be unable to be rescued by pharmacoperone treatment, due to the presence of structural defects critical for protein function (such as the S168R and S217R GnRHR mutations which are not rescuable).

Test Agents

In general, characteristics of molecules that function as pharmacoperones for conformationally defective proteins include one or more of the following characteristics: cell-permeability; high specificity for the mis-folded protein to be rescued (such as a Kd of no more than 1 µM for the protein of interest and a Kd of greater than 1 µM for another protein); an ability to arrive at the correct place in the cell (for example, the ability to penetrate the cell membrane, traffic to the endoplasmic reticulum, and remain undegraded long enough to stabilize the target mutant protein or change the protein mis-folding energetics of the mis-folded protein); and the ability to dissociate from the mutant protein (for example, to not compete with the physiological ligand) after the rescued protein arrives at its appropriate cellular location (such as the plasma membrane). Pharmacoperone assays can be used that select agents having one or more of these characteristics.

In particular examples, pharmacoperone agents that are successful in restoring function to one of a number of mutations found in a particular mutant protein will restore function to at least one other mutation found in that mutant protein. For example, if a particular pharmacoperone can restore function to the $E^{90}K$ human GnRHR mutant protein, then the pharmacoperone can restore function to at least one other human GnRHR mutant protein, such as protein including an $N^{10}K$ mutation, a $T^{32}I$ mutation, a $Q^{106}R$ mutation, an $A^{129}D$ mutation, an $R^{139}H$ mutation, a $A^{171}T$ mutation, a $C^{200}Y$ mutation, an $R^{262}Q$ mutation, a $L^{266}R$ mutation, a $C^{279}Y$ mutation, or a $Y^{284}C$ mutation.

The assay includes selecting a test agent (such as at least one or at least two test agents) that can penetrate a cell membrane and specifically bind to the protein of interest, without significantly interfering with the biological activity of the protein. If the test agent alone cannot penetrate a cell surface membrane to reach the inside of a cell, it can be provided in a vehicle (such as a lipid carrier, DMSO, alcohol, or other agents that are membrane permeable) that will facilitate transport of the test agent through the cell surface membrane and into the cell. In some examples, electroporation is used to introduce the test agent into the cell.

Ideally, the test agent binds with high specificity to the mis-folded protein of interest, but does not significantly bind to other proteins in the cell. In some examples, the test agent has a dissociation constant of no more than 1 µM at for the mis-folded protein of interest, but has a Kd of greater than 1 µM for one or more other proteins. In some examples, the method includes contacting the test agent with another cellular protein under conditions that permit the test agent to bind to the other protein, and determining whether the test agent can bind to the other protein. In some examples, the method includes determining the Kd of the test agent for the other protein. An inability to specifically bind to the other protein while having the ability to rescue a mis-folded mutant protein indicates that the test agent is a pharmacoperone substantially specific for the mutant protein.

Although the test agent in some examples may interfere with the biological activity of the corresponding native protein, in particular examples the test agent does not significantly interfere with the biological activity of the native protein. For example, in some examples, the test agent is not an antagonist, and therefore does not significantly interfere with the biological activity of the native protein. In particular examples, the test agent does not reduce the biological activity of the native protein by more than 25%, such as no more than 20%, such as no more than 10% as compared to an amount of activity by the protein which has not been contacted with the test agent.

In particular examples, selecting a test agent includes selecting a test agent that has the desired activity at a concentration that does not significantly interfere with binding of a ligand to the receptor protein. In some examples, a test agent does not significantly interfere with a ligand binding to its receptor, if at the concentration needed for rescue of the mis-folded receptor, the amount of ligand binding to the receptor does not decrease by more than 20%, such as no more than 10%, such as no more than 5%. Methods are known in the art for determining whether the test agent interferes with ligand binding. For example, a competition assay can be used wherein the test agent (at the minimum concentration needed to restore function to the mis-folded receptor) and an appropriate ligand are incubated with the receptor, and an amount of binding of the ligand to the receptor is determined. The amount of ligand binding can be compared to an amount of ligand binding in the absence of the test agent. Decreased binding in the presence of the minimum concentration of test agent needed to rescue the mis-folded receptor, for example a decrease of at least 20%, at least 50%, or at least 75%, indicates that the test agent interferes with binding of the ligand to the receptor.

In some examples, selecting a test agent includes selecting a test agent that is a peptidomimetic of a molecule that binds to the protein, such as a peptidomimetic of a ligand or agonist of a receptor.

In particular examples, the test agent can dissociate from the protein. Therefore, the methods disclosed herein can include determining the ability of the test agent to dissociate from the mutant protein, for example, after it has been rescued and folded in such a way as to increase the biological activity of the protein. In one example, $K_{off}$ is determined using methods known in the art. In another example, for example when the test agent is an agonist of the protein, dissociation can be determined empirically, for example by measuring a loss of activation of the protein. For example, after contacting the protein with a therapeutic amount of the test agent, dissociation of the test agent from the protein can be determined by measuring an amount of decrease in biological activity of the protein. In another example, for example where the test agent is an antagonist of the protein, dissociation can be determined empirically, for example by measuring a decrease in the ability of the test agent to decrease agonist activity. For example, after contacting the protein with a therapeutic amount of the test agent, dissociation of the test agent from the protein can be determined by measuring an amount of increase in biological activity of the protein in the presence of an agonist of the protein.

In one example, the test agent to be screened is an antagonist, such as a GnRHR antagonist. Exemplary antagonists include, but are not limited to derivatives, analogs, and mimetics of indole, quinolone, and macrolide antibiotics, such as Q89, (7-chloro-2-oxo-4-{2-[(2S)-piperidin-2-yl]ethoxy}-N-pyrimidin-4-yl-3-(3,4,5-trimethylphenyl)-1,2-dihydroquinoline-6-carboxamide); Q76, (N-(7-chloro-3-(3, 5-dimethylphenyl)-2-oxo-4-{2-[(2S)-piperidin-2-yl] ethoxy}-1,2-dihydroquinolin-6-yl)-N'-cyclopropylurea); Q08, ((2S)-2-(2-{[7-chloro-6-[(6,7-dimethoxy-3,4-dihydroisoquinolin-2(1H)-yl)carbonyl]-3-(3,5-dimethylphenyl)-2-oxo-1,2-dihydroquinolin-4-yl]oxy}ethyl)piperidinium trifluoroacetate); In30, ((2S)-2-[5-[2-(2-azabicyclo[2.2.2]oct-2-yl)-1,1-dimethyl-2-oxoethyl]-2-(3,5-dimethylphenyl)-1H-indol-3-yl]-N-{2-[4-(methylsulfinyl)phenyl]ethyl}propan-1-amine); In3, ((2S)-2-[5-[2-(2-azabicyclo[2.2.2]oct-2-yl)-1,1-dimethyl-2-oxoethyl]-2-(3,5-dimethylphenyl-1H-indol-3-yl]-N-(2-pyridin-4-ylethyl)propan-1-amine; A-64755.0 (11-deoxy-11-[carboxy-phenylethylamino]-6-O-methyl-erythromycin A 11,12-(cyclic carbamate)); A-177775.0, (3'-N-desmethyl-3'-N-cyclopentyl-11-deoxy-11-[carboxy-(3,4-dichlorophenylethylamino)]-6-O-methyl-erythromycin A 11,12-(cyclic carbamate)); and A-222509.0, 3',3'-N-desmethyl-3',3'-N-cyclopropylmethyl-11-deoxy-11-[carboxy-(3-chloro,4-fluoro-phenylethylamino)]-6-O-methyl-erythromycin A 11,12-(cyclic carbamate)). Analogs of these agents are examples of candidates for use in the disclosed screening assay.

In some examples, indoles and quinolones to be screened have an $IC_{50}$ of less than 5 nM for wild-type human GnRHR, for example less than 4 nM, less than 3 nM, less than 2.5 nM, less than 2.3 nM, less than 2 nM, or less than 1 nM. In other examples, the macrolide antibiotic to be screened, such as an erythromycin-derived macrolide, has an $IC_{50}$ of less than 700 nM for wild-type human GnRHR, for example less than 100 nM, less than 25 nM, less than 20 nM, or less than 5 nM.

In particular examples, test agents to be screened are developed using standard combinatorial chemistry methods.

The mis-folded protein can be a mis-folded receptor. In such examples, the test agent can bind to the ligand binding site of the receptor, and may stabilize the ligand binding site. In particular examples, the test agent is a non-antagonist of the receptor, such as an agonist or ligand of the receptor. In other examples, the test agent is an antagonist of the receptor and therefore may compete with the ligand for binding to the receptor. In some examples where the test agent is an antagonist of the receptor, the test agent can have an inhibitory concentration ($IC_{50}$) of less than 1000 nM (for example less than 700 nM, less than 100 nM, less than 20 nM, less than 5 nM, less than 3 nM, less than 2.5 nM, or less than 2 nM).

Methods of determining the $IC_{50}$ of an agent are known in the art. For example, the method can include contacting the test agent with a wild-type receptor, such as a native GnRHR sequence, under conditions that allow interaction between the test agent and the wild-type receptor, in the presence or absence of an agonist of the receptor, and then determining an $IC_{50}$ of the test agent for the wild-type receptor. The specificity of the agent for receptor, for example by measuring IP production (as described herein) in the presence of a range of receptor agonist concentrations (such as about $10^{-13}$ M-$10^{-7}$ M) and in the presence of a single concentration of agent (such as about 1 μg/ml) is determined. In particular examples, indoles and quinolones having an $IC_{50}$ of less than 3 nM for wild-type GnRHR, and macrolides with an $IC_{50}$ of less than 700 nM for wild-type GnRHR, are selected as candidate agents that can restore function to a mutant GnRHR.

However, the test agent can bind to a region of the receptor outside of the ligand binding site. Test agents that bind outside the natural ligand binding site of a receptor are not likely to interfere with subsequent activation of the receptor with an agonist.

Mis-Folded Proteins

A mis-folded protein includes at least one mutation (such as one, two, three, at least two, or at least three mutations) that affects folding of the protein, routing of the protein to the cell membrane surface, or both, and decreases the biological activity or function of the protein. Exemplary mutations include, but are not limited to, amino acid substitutions, deletions, insertions, or combinations thereof. The mis-folded protein results in or causes disease in a subject. In some examples, mutations in cell surface membrane receptors and channels, such as hGnRHR, occur in regions of the protein not involved in ligand binding or effector activation.

The mutant protein can be a mutant receptor that is mis-routed in the cell. Exemplary receptors include hormone receptors (such as sex hormones and hormones involved in homeostasis), receptors of the nervous system, cardiovascular system, renal system, pulmonary system, musculoskeletal system, and so forth. In particular examples the receptor is a G-coupled protein receptor that includes one or more mutations that results in disease in a subject. For example, mutations in the cystic fibrosis transmembrane conductance regulator (CFTR) (such as ΔF508 CFTR) can cause cystic fibrosis. Mutations in the gonadotropin-releasing hormone receptor (GnRHR) (such as $N^{10}K$ mutation, a $T^{32}I$ mutation, an $E^{90}K$ mutation, a $Q^{106}R$ mutation, an $A^{129}D$ mutation, an $R^{139}H$ mutation, a $A^{171}T$ mutation, a $C^{200}Y$ mutation, an $R^{262}Q$ mutation, a $L^{266}R$ mutation, a $C^{279}Y$ mutation, a $Y^{284}C$ mutation, or combinations thereof) can cause hypogonadotropic hypogonadism (HH). Mutations in rhodopsin (such as an $P^{23}H$, $R^{135}L$, $C^{759}F$, R677ter, or a L1447fs mutation in a human rhodopsin amino acid sequence, also see Seyedahmadi et al., *Exp. Eye Res.* 79:167-73, 2004, herein incorporated by reference) can result in retinitis pigmentosa. Mutations in alpha-1 antitrypsin (such as the deficiency allele Glu342Lys in the human sequence) can result in emphysema or alpha 1 antitrypsin deficiency liver disease.

However, one skilled in the art will appreciate that the mutant protein does not have to be a G-coupled protein receptor. The disclosed methods can be used to identify pharmacoperone agents specific for other proteins. For example, mutations in low-density lipoprotein (LDL) (such as C83Y, C675X, E119K, E207K, E207X, F382L, R574Q, or a P664L mutation in the human LDL sequence; also see mutations disclosed in Muller et al., *Atheroscler. Suppl.* 5:1-5, 2004 and Sozen et al., *Atheroscler. Suppl.* 5:7-11, 2004, herein incorporated by reference) can cause familial hypercholesterolemia. Mutations in the aquaporin-2 or the arginine-vasso-presin $V_2$ (AVP $V_2$) receptor (such as a R137H substitution in the human sequence) can cause nephrogenic diabetes insipidus. Mutations in lens crystallins (such as a P23T, G91del or a Y437H mutation in a human lens crystallin protein) can cause cataracts. Mutations in the mitochondrial branched-chain alpha-ketoacid dehydrogenase (BCKD complex) (such as N126Y, C219W (alpha subunit), H156Y (beta subunit), V69G (beta subunit), R274stop, H391R, or a S133stop mutation in a human BCKD amino acid sequence) can result in maple syrup urine disease. Mutations in ATP7A and ATP7B (such as those described in Hsi and Cox, Hum. Genet. 114(2):165-72, 2004, herein incorporated by reference) can result in Menkes disease. Mutations in ataxin-3 (such as those described in Brusco et al., *Arch Neurol.* 61(5):727-33, 2004, herein incorporated by reference) can result in Machado-Joseph disease. Mutations in p53, pp60, ubiquitin-activating enzyme E1, or the glucocorticoid receptor (such as those described in Kino and Chrousos, *Essays Biochem.* 40:137-55, 2004, herein incorporated by reference) can result in cancer. Mutations in an amyloid precursor protein, presenilin 1, or presenilin 2 (such as the T714A or V715A mutation in the human amyloid precursor protein; a Thr113-114ins, Leu85Pro, H163R, M139V, P117R, I213F, V272A, or R278I mutation in human presenilin-1; and a Q228L, M239V or M239I mutation in human presenilin 2) can result in Alzheimer's disease. Mutations in transthyretin (such as a V30M, V30A, or F33V mutation in a human sequence) can result in familial amyloid polyneuropathy (FAP), and mutations such as Asp18Glu and V122I can result in familial amyloidotic cardiomyopathy (FAC). Mutations in prion protein (such as a P102L, D178N with 129M and 129V polymorphism, T183A, V180I, F198S, E200K, R208H, V210I, or Q217R, mutation in the human protein) can result in spongiform encephalopathies. Mutations in beta-glucosidase protein (such as D63N, D106N, I158S, P182L, N188S, R257X, Y313H, E326K, N370S, P391L, N392I, 1402T, D409H, V230E, L444P, Y451Y, Y456X, H490R or double mutants N188S and E326K, and L444P and E326K, in the human sequence) can result in Gaucher disease. Mutations in beta-galactosidase protein can result in beta-galactosidosis. Mutations in amyloid can result in Creutzfeldt-Jakob disease. Mutations in alpha-synclein, Parkin, or ubiquitin C can result in Parkinson's disease. Mutations in hemoglobin (such as beta6 Glu to Val and beta142 Ala to Val) can result in sickle cell anemia. Mutations in amyloid fibrils can cause systemic amyloidosis.

In a particular example, the protein is a human GnRHR protein that includes one or more of the following mutations in a human GnRHR amino acid sequence: $N^{10}K$, $T^{32}I$, $E^{90}K$, $Q^{106}R$, $A^{129}D$, $R^{139}H$, $C^{200}Y$, $R^{262}Q$, $L^{266}R$, $C^{279}Y$ or a $Y^{284}C$ amino acid substitution. In a specific example, the protein is a human GnRHR protein that includes a $Q^{106}R/L^{266}R$ mutation, $A^{171}T/Q^{106}R$ mutation, a $L^{314}X_{(stop)}/Q^{106}R$ mutation, a $T^{32}I/C^{200}y$ mutation, a $R^{262}Q/A^{129}D$ mutation, a $R^{262}Q/Q^{106}R$ mutation, a $N^{10}Q/Q^{106}R$ mutation, or a $R^{262}Q/Y^{284}C$ mutation. In some examples, the protein is a human GnRHR protein that includes an E90K mutation. In other examples, the mutant GnRHR is a rat GnRHR including a Des325-327, DesL237-L241 or a C278A mutation.

Exemplary Assays for Determining Rescue of Function

Several types of assays can be used (alone or in combination) to determine whether functionality was restored to the mutant protein by the one or more test agents. Methods used to determine whether the test agent can restore biological function to the mutant protein can depend on the mutant protein of interest. Generally, the assay includes contacting a test agent with a mis-folded protein (such as contacting a cell expressing the protein with the test agent) under conditions that allow interaction between the test agent and the mis-folded mutant protein, and then determining whether functionality was restored to the mutant protein. For example, the conditions can include those that permit the test agent to cross the cell membrane and bind to the mis-folded protein for a time sufficient for the protein to be correctly folded.

Several methods are disclosed for determining whether functionality is restored to the mis-folded protein. However, the method of determining whether functionality was restored to the mutant protein by the test agent can depend on the biological activity of the protein, on the location of the protein in the cell, or other factors known to those in the art. Therefore, although particular methods are disclosed, the screening assays are not limited by these particular examples, as those skilled in the art will be able to identify the appropriate functional assay depending on the mis-folded protein of interest.

Exemplary methods that can be used to determine if the biological function of a mis-folded protein is rescued by one or more test agents include, but are not limited to: determining an amount of production of an intracellular molecule that indicates protein function (such as production of IP by a G-coupled-protein receptor), determining an amount specific binding of a molecule (such as an antibody, ligand, agonist, or antagonist) to the protein, determining an amount of molecule bound to the protein at the cell surface and internalized (such as an amount of internalized antibody-, ligand-, agonist-, or antagonist-mutant protein complex), or combinations thereof.

In some examples, the method of determining if the mutant receptor protein is rescued includes determining if the protein is trafficked to the cell surface membrane of a cell treated with the test agent. For example, if the mutation adversely affects receptor folding and diminishes proper localization of the receptor at the cell membrane, an amount of antibody, ligand, agonist, or antagonist binding at the cell surface can be determined using any method used by those skilled in the art. In one example, during or following incubation of the cell with the test agent, the cell is incubated with a molecule specific for the receptor (such as an antibody, ligand, agonist, or antagonist) for a time sufficient to allow binding of the molecule to the receptor present on the cell surface. Such molecules can include a label (such as a radiolabel or fluorophore) to permit detection of the molecule-receptor complex. Alternatively, another agent including a label that recognizes the molecule bound to the receptor, such as a labeled secondary antibody, can be used to detect the presence of the molecule-receptor complex. The presence of the molecule-receptor complex present on the surface can be detected and in some examples further quantitated. In some examples, a relative amount of molecule-receptor complex present on the surface is compared to an amount of molecule-receptor complex present on the surface of a cell not previously exposed or incubated with the test agent. An increase in molecule-receptor complex on the surface of a cell exposed to the test agent, compared to an amount of molecule-receptor complex present on the surface of a cell not previously exposed or incubated with the test agent, indicates that the test agent is a pharmacoperone agent for the mis-folded receptor. In particular examples, the amount of molecule-receptor complex present on the surface of a cell exposed to the test agent increases by at least 20%, such as at least 25%, at least 50%, at least 75%, at least 100%, at least 200%, or even at least 1000% as compared to an amount of molecule-receptor complex present on the surface of a cell not previously exposed or incubated with the test agent.

Another assay that can be used to determine whether functionality was restored to a mis-folded mutant protein includes determining an amount of molecules specific for the protein which are bound to the protein at the cell surface and internalized. Such a method can be used to determine whether an increased number of proteins traffic to the cell surface in the presence of the test agent. An increased number of proteins at the cell surface is an indication that the test agent is a pharmacoperone for the mis-folded mutant protein. Any method used by those skilled in the art can be used to measure internalization of surface-bound mutant protein-molecule complex. In one example, an antibody or other agent specific for an extracellular domain of the mutant protein (such as an agonist or ligand) can be incubated with the cells during or after incubation with the test agent. This incubation can be performed at 4° C. for a time sufficient to allow the agent specific for an extracellular domain of the mutant protein to bind to those proteins on the cell surface, thereby forming a mutant protein-molecule complex. Un-bound agent is removed, and the cells warmed, for example to 37° C., to allow internalization of the complex. The surface of the cells can be stripped at various times, to remove any un-internalized agent. Complexes (such as a ligand-protein, agonist-protein, or antibody-protein complex) that were internalized will not be removed, and can be detected, for example by detecting a label on the agent specific for an extracellular domain of the mutant protein. In another example, the agent specific for an extracellular domain of the mutant protein is incubated with the cells during or after incubation with the test agent at 37° C., and the complex allowed to internalize. At the desired time, the agent specific for an extracellular domain of the mutant protein is removed from the cell surface, and the amount of complex present in the cell determined, for example by detecting a label present on the agent specific for an extracellular domain of the mutant protein. In a particular example, the agent specific for an extracellular domain of the mutant protein includes a radiolabel or a fluorophore, and internalization is determined by quantitating the amount of radioactivity or fluorescence, respectively, present. An increase in internalized complexes in the presence of the test agent (or following incubation with the test agent), compared to an amount present in the absence of the test agent, indicates that the test agent is a pharmacoperone agent for the mutant protein. In particular examples, the amount of internalized complex present in a cell exposed to the test agent increases by at least 20%, such as at least 25%, at least 50%, at least 75%, at least 100%, at least 200%, or even at least 1000%, as compared to an amount of internalized complex present in a cell not previously exposed or incubated with the test agent.

In an example where the test agent is an agonist of a mis-folded mutant receptor, methods can be used to determine whether the agonist can restore function to the mutant protein. For example, the amount an intracellular marker produced which is indicative of protein function can be determined. In examples where the mutant protein is a mutant G-coupled protein receptor (GCPR), the method can include determining an amount of inositol phosphate (IP) production by the cell, wherein an increase in IP production by a cell exposed to the test agent as compared to an amount of IP production by a cell not exposed to the test agent indicates that the agent restored functionality to the mutant GCPR. In particular examples, IP production increases by at least 25%, such as at least 50%, at least 75%, at least 100%, at least 200%, or even at least 1000% in the presence of the test agent, as compared to an amount of IP production in the absence of the test agent. Any method used by those skilled in the art can be used to measure IP production. In one example, IP production is measured as follows. Following incubating the test agent with the cell expressing the mutant GCPR, the cell is washed to remove the test agent, then incubated with [$^3$H] inositol (a precursor of IPs) for a time sufficient to allow uptake of the inositol by the cell. The cell is then contacted the cell with a GCPR agonist for a time sufficient to allow stimulation of IP production, and the amount of IP produced determined, for example by disrupting the cells and the amount of radioactivity incorporated into total IPs is determined by liquid scintillation spectroscopy (for example, see the method described in Huckle and Conn, *Methods Enzymol.* 141:149-55, 1987). Exemplary GnRHR agonists include buserelin (D-tert-butyl-Ser$^6$, des-Gly$^{10}$, Pro$^9$, ethylamide-GnRH), leuprolide (D-Leu$^6$, Pro$^9$, des-Gly$^{10}$-ethylamide-GnRH), and GnRH. An exemplary rhodopsin agonist includes light.

In some examples where the mutant protein is a mis-folded receptor protein, the method can include determining if the test agent competes with a ligand specific for the receptor. The presence of competition between the ligand and the test agent for the ligand binding site indicates that the test agent binds to the ligand binding site, and the absence of detectable competition for the ligand binding site indicates that the test agent does not bind to the ligand binding site. In addition, the method can include determining if the test agent is a non-antagonist of the receptor. For example, if the test agent binds to the ligand-binding site of a receptor and interferes with binding of a ligand or agonist to the receptor ligand binding site, thereby resulting in decreased receptor-associated responses normally induced by the ligand or agonist (such as a decrease of at least 20% as compared to a response in the absence of the test agent), this indicates that the test agent is an antagonist of the receptor. In contrast, if the test agent binds to the receptor (whether at a ligand binding site or not) and increases receptor-associated biological responses (such as an increase of at least 20% as compared to a response in the absence of the test agent), this indicates that the test agent is a non-antagonist of the receptor.

The assay can further include determining which of at least two mutations (such as the one of two, three, four, five, six, seven, eight, nine, or even at least 10 different mutations) in a protein, is rescued by the greatest amount by a pharmacoperone. The mutation that is best rescued can be used to identify other pharmacoperones. For example, if the biological activity of mutant protein X with mutation 1 is increased by 20% in the presence of the test agent, and mutant protein X with mutation 2 is increased by 90% in the presence of the test agent, mutant protein X with mutation 2 (wherein mutation 1 or 2 can be any different combination of amino acid substitutions, deletions, or insertions) can be used in the disclosed screening assays to identify other pharmacoperones that can rescue the mutant protein. As described herein, it has been found that in some examples, a pharmacoperone agent that can rescue one mutation in a protein can also rescue at least one other mutation in the protein that results in mis-folding of the protein.

As described in the examples below, agents identified that were able to restore function to a mutant GnRHR, were also able to increase the presence of wild-type human GnRHR on the cell surface. Therefore, the methods described above can also be used to screen for agents that increase trafficking of wild-type proteins (such as receptors) to the cell surface. In particular examples, wild-type protein is contacted with the test agent, and the biological activity of the protein determined, for example using the methods described herein (such as determining an amount of production of an intracellular marker of protein function, and binding of a molecule having high affinity for the protein), and compared to an amount of activity in the absence of the agent. In one example, such agents can be used to treat subjects having hypogonadism, for example to alleviate symptoms associated with erectile dysfunction, infertility, decreased libido, decrease in beard and growth of body hair, decrease in size or firmness of the testicles, decrease in muscle mass and increase in body fat, enlarged male breast tissue, hot flashes, mood swings, irritability, depression, fatigue, osteoporosis, delayed puberty, or combinations thereof.

Restoring Function to Mis-folded Proteins

Methods are disclosed for restoring function to proteins that are mis-folded, and are mis-routed, mis-localized, or aggregated as a result of the misfolding. In particular examples, the disclosed methods can be used to treat a disease that results from a mis-folded protein. For example, a mutant receptor may be expressed in a cell, but not transported to the cell surface. In order to restore function to such receptors, the method includes contacting the cell with a therapeutically effective amount of a pharmacoperone agent that increases transport of the mutant receptor to the cell surface. By allowing the mutant receptor to correctly route to the plasma membrane, an increased number of receptors are available at the cell surface for ligand binding.

Accumulation and aggregation of misfolded proteins are responsible for some neurodegenerative diseases such as early-onset familial Alzheimer disease (due to a mutation(s) in β-amyloid), Parkinson disease (due to mutation(s) in alpha-synuclein, Parkin, or ubiquitin C), Creutzfeldt-Jakob (due to mutation(s) in amyloid) and spongiform encephalopathies (due to due to mutation(s) in prion glycoprotein), as well as for early onset cataracts (due to a mutation(s) in lens crystallin), $\alpha_1$-antitrypsin deficiency and emphysema (due to a mutation(s) in alpha 1 antitrypsin), type II diabetes mellitus and systemic amiloydoses (due to a mutation(s) in amyloid fibrils, light chain variable domains). In these diseases, proteins or fragments of proteins convert from their normally soluble conformations to insoluble, well-structured fibrillar aggregates, known as amyloids (such as β-amyloid in Alzheimer disease and α-synuclein in Parkinson disease), which are formed by cross-β-pleated sheet structures that accumulate intra/or extracellularly.

Many diseases associated with protein mis-folding, impaired intracellular trafficking, or increased degradation involve membrane-associated proteins. Diseases caused with cell-surface protein mis-localization or increased degradation of otherwise functionally competent molecules includes forms of familial hypercholesterolemia, retinitis pigmentosa, cystic fibrosis, and diabetes insipidus. Several mutations in the low-density lipoprotein (LDL) receptor involve defects in trafficking or processing that lead to accelerated degradation of the receptor. In cystic fibrosis, the $\Delta F^{508}$ mutation (found in ~70% of patients with this condition), leads to chaperone-mediated ER retention and rapid degradation of the incompletely processed (albeit functional) cystic fibrosis transmembrane conductance regulator (CFTR) by the proteasome; this prevents cell surface expression of the chloride channel protein and consequently loss of cyclic AMP-regulated chloride transmembrane conductance. In nephrogenic diabetes insipidus, urine concentration is defective due to resistance of the kidney to arginine-vasopressin (AVP) or to defects involving the arginine-vasopressin-responsive aquaporin-2 water channel. When expressed in vitro, most (~70%) AVP $V_2$ receptor mutations exhibit intracellular trapping of the receptor molecules that are then unable to reach the cell membrane. Similarly, mutations of aquaporin-2 water channel can cause misrouting of the protein, preventing its cell surface expression. In retinitis pigmentosa (a disease characterized by retinal degeneration and, ultimately, total blindness), mutations in the gene encoding rhodopsin result in defective molecules that misfold and accumulate in the ER. Mutations in the carboxyl-terminus of rhodopsin cause defects in receptor trafficking to the outer segment of the rod cell. Mutations in the gene of another GPCR, the GnRHR) cause misfolding of the receptor protein leading to impaired gonadal function. In a particular example, the subject to be treated has HH and at least one of the following mutations in their GnRHR amino acid sequence: a $N^{10}K$ mutation, a $T^{32}I$ mutation, an $E^{90}K$ mutation, a $Q^{106}R$ mutation, an $A^{129}D$ mutation, an $R^{139}H$ mutation, a $A^{171}T$ mutation, a $C^{200}Y$ mutation, an $R^{262}Q$ mutation, a $L^{266}R$ mutation, a $C^{279}Y$ mutation, a $Y^{284}C$ mutation, or combinations thereof.

Therefore, the disclosed methods can be used to treat any of the diseases noted herein, for example using a pharmacoperone identified for the mis-folded protein using the assays disclosed herein. However, the disclosure is not limited to the treatment of the particularly listed diseases, as those skilled in the art will recognize that other diseases that result from a mis-folded protein can be treated using the disclosed methods.

The disclosed methods include identifying, detecting, determining, or establishing which mutation(s) is present in the protein of interest, wherein the presence of a particular mutation indicates that the subject can be treated with a pharmacoperone specific for the mis-folded mutant protein. It has been determined that particular mutations are susceptible to treatment with a pharmacoperone, while other mutations are not. Based on the knowledge of which mutations are present in the protein of interest, subjects having the particular mutation(s) susceptible to treatment with a pharmacoperone are administered a therapeutically effective amount of the pharmacoperone. In some examples following administration of the pharmacoperone, the subject is administered a therapeutic amount of an agonist of the receptor to activate the rescued receptor.

The pharmacoperone can be cell membrane permeable and substantially specific for the protein of interest. In some examples, the pharmacoperone administered was selected using the assay described above. In some examples, the pharmacoperone does not bind to a ligand binding site of the receptor protein of interest. In yet other examples, the pharmacoperone is an agonist of the receptor. In examples where the pharmacoperone is an antagonist of the receptor protein, the receptor is not a V2 vasopressin receptor or a histamine-H2 receptor.

The disclosed methods of restoring function to a mis-folded mutant protein include contacting the protein with a therapeutically effective amount of a pharmacoperone, wherein contacting restores function to the mutant protein. Restoring function to the mutant protein can include increasing biological function by at least 20% as described above. In particular examples, the mutant protein (such as a mutant GCPR) is present in a subject, and the method includes administering a therapeutically effective amount of a pharmacoperone to the subject. The pharmacoperone can be administered in a pharmaceutically acceptable carrier, alone or in the presence of additional therapeutic agents. In one example, the subject has hypogonadotropic hypogonadism (HH).

In particular examples, the pharmacoperone is administered to the subject, followed by a period when the pharmacoperone is not administered to the subject (for example to permit dissociation of the pharmacoperone from the mutant protein), and subsequently administering additional pharmacoperone to the subject, or in some examples subsequently administering an agonist of the protein to activate the rescued protein. Administration can be achieved using any method available in the art. Exemplary routes of administration include, but are not limited to: topical, transdermal, transmucosal, intravenous, ip, intramuscular, and so forth.

In some examples, the period when the pharmacoperone is not administered to the subject is at least 2 hours, such as at least 3 hours, at least 6 hours, at least 12 hours, at least 24 hours, at least 48 hours, at least 72 hours, or even at least 96 hours. In some examples, this type of administration is used when the pharmacoperone is antagonist of the receptor. For example, if the pharmacoperone is an antagonist that binds to the receptor at its ligand binding site, thereby interfering with binding of the ligand, the pharmacoperone is removed from the receptor (for example by terminating administration of the pharmacoperone) so that the rescued receptor can more effectively bind ligand and couple to its effector protein. In other examples, antagonists bind to the receptor, but do so reversibly, thereby providing a mechanism for removing the therapeutic antagonist. In yet other examples where the antagonist does not bind to the receptor at its ligand binding site, and therefore does not interfere with binding of the ligand once the receptor reaches the cell surface, removal of the antagonist may not be needed before activating the receptor with an agonist.

Increasing Wild-type Proteins on the Cell Surface

Similarly, pharmacoperone agents identified using the disclosed methods can also be used to increase an amount of wild-type protein (such as a receptor) at the cell surface. In some examples, a therapeutically effective amount of a pharmacoperone agent that can restore function to a mutant protein can be used to increase expression of a wild-type protein (for example, on the cell surface). In particular examples, methods are also provided for increasing the amount of wild-type human GnRHR on the cell surface.

The method includes contacting a therapeutically effective amount of alpharmacoperone (such as a pharmacoperone identified using the screening assay described above) with the wild-type protein, wherein contacting increases expression of the protein at the cell surface. In one example, the amount of wild-type protein on the cell surface increases by at least 10%, for example at least 25%, at least 50%, at least 100%, or even at least 150%, in the presence of the agent, as compared to an amount present in the absence of the agent (for example an amount of expression of the wild-type protein at the cell surface in a cell not previously contacted with the test agent).

In some examples, the wild-type protein is present in a subject, and the pharmacoperone is administered to the subject in a therapeutically effective amount. In particular examples, the subject has hypogonadism, and may have one or more of the following symptoms: erectile dysfunction, infertility, decreased libido, decrease in beard and growth of body hair, decrease in size or firmness of the testicles, decrease in muscle mass and increase in body fat, enlarged male breast tissue, hot flashes, mood swings, irritability, depression, fatigue, osteoporosis, delayed puberty, or combinations thereof.

EXAMPLE 1

Pharmacological Rescue of GnRHR Mutants

This example describes methods used to demonstrate that agents from several different chemical classes can restore functionality to several rat and human GnRH mutant receptors. One skilled in the art will appreciate that similar methods can be used to screen other agents of interest, such as other indoles, quinolones, and erythromycin-derived macrolides. Furthermore, similar methods can be used to screen and restore function to other mutant G-protein-coupled receptors.

The following chemical structures (collectively referenced as "the agents") were utilized; those of the quinolone class are prefaced by the letter "Q" and those of the indole class by the letters "In" and were produced by Merck and Company (Ashton et al., *Bioorg. Med. Chem. Lett.* 11: 1727-31, 2001; Ashton et al. *Bioorg. Med. Chem. Lett.* 11: 1723-6, 2001; and Ashton et al., *Bioorg. Med. Chem. Lett.* 11:2597-602, 2001): Q89, (7-chloro-2-oxo-4-{2-[(2S)-piperidin-2-yl]ethoxy}-N-pyrimidin-4-yl-3-(3,4,5-trimethylphenyl)-1,2-dihydroquinoline-6-carboxamide); Q76, (N-(7-chloro-3-(3,5-dimethylphenyl)-2-oxo-4-{2-[(2S)-piperidin-2-yl]ethoxy}-1,2-dihydroquinolin-6-yl)-N'-cyclopropylurea); Q08, ((2S)-2-(2-{[7-chloro-6-[(6,7-dimethoxy-3,4-dihydroisoquinolin-2(1H)-yl)carbonyl]-3-(3,5-dimethylphenyl)-2-oxo-1,2-dihydroquinolin-4-yl]oxy}ethyl)piperidinium trifluoroacetate); In30, ((2S)-2-[5-[2-(2-azabicyclo[2.2.2]oct-2-yl)-1,1-dimethyl-2-oxoethyl]-2-(3,5-dimethylphenyl)-1H-indol-3-yl]-N-{2-[4-(methylsulfinyl)phenyl]ethyl}propan-1-amine); In31b, ((2S)-N-[2-(4-carboxyphenyl)ethyl]-2-[5-[1,1-dimethyl-2-(4-methylpiperazin-1-yl)-2-oxoethyl]-2-(3,5-dimethylphenyl)-1H-indol-3-yl]propan-1-aminium trifluoroacetate); In3, ((2S)-2-[5-[2-(2-azabicyclo[2.2.2]oct-2-yl)-1,1-dimethyl-2-oxoethyl]-2-(3,5-dimethylphenyl)-1H-indol-3-yl]-N-(2-pyridin-4-ylethyl)propan-1-amine.

Erythromycin-derived macrolides were prepared by Abbott Laboratories (Bush et al. (1999) Program and Abstracts of the 81st Annual Meeting of the Endocrine Society, San Diego, Calif., Abstract P3-225; Diaz et al. (1999) Program and Abstracts of the 81st Annual Meeting of the Endocrine Society, San Diego, Calif., Abstract P3-226) and are prefaced by the letter "A." A-7662.0, (Erythromycin A); A-64755.0 (11-deoxy-11-[carboxy-phenylethylamino]-6-O-methyl-erythromycin A 11,12-(cyclic carbamate)); A-177775.0, (3'-N-desmethyl-3'-N-cyclopentyl-11-deoxy-11-[carboxy-(3,4-dichlorophenylethylamino)]-6-O-methyl-erythromycin A 11,12-(cyclic carbamate)); A-222509.0, 3',3'-N-desmethyl-3',3'-N-cyclopropylmethyl-11-deoxy-11-[carboxy-(3-chloro,4-fluoro-phenylethylamino)]-6-O-methyl-erythromycin A 11,12-(cyclic carbamate)).

Wild-type (WT) hGnRHR cDNA in pcDNA3 was subcloned into pcDNA3.1 at KpnI and XbaI restriction enzyme sites. All GnRHR mutants were constructed, sequenced and prepared using standard molecular biology techniques (Janovick et al., *J. Clin. Endocrinol. Metab.*, 87:3255-62, 2002). Naturally occurring mutants of hGnRHR associated with human hypogonadotropic hypogonadism, $N^{10}K$, $T^{32}I$, $E^{90}K$, $Q^{106}R$, $A^{129}D$, $R^{139}H$, $S^{168}R$, $C^{200}Y$, $S^{217}R$, $R^{262}Q$, $L^{266}R$, $C^{279}Y$ and $Y^{284}C$, were generated. Manufactured mutants of the rGnRHR included the shortest rat GnRHR c-terminal truncation mutant that results in receptor loss-of-function, $des^{325-327}$-rGnRHR; two deletion mutants ($des^{237-241}$-rGnRHR, and $des^{260-265}$-rGnRHR) and two Cys mutants ($C^{229}A$-GnRHR and $C^{278}A$-GnRHR).

Large-scale plasmid DNAs were prepared using a Qiagen Endotree Maxi-prep kit (Qiagen, Valencia, Calif.). The purity and identity of the amplified plasmid DNAs were further verified by restriction enzyme analysis. WT and mutant hGnRHR were separately transiently expressed in COS-7 cells using standard molecular biology methods (Leaños-Miranda et al., *J. Clin. Endo. Metab.*, 87:4825-8, 2002). Briefly, cells were maintained in growth medium (DMEM) containing 10% fetal calf serum (FCS; Life Technologies, Grand Island, N.Y.) and 20 µg/ml gentamicin (Gemini Bioproducts, Calabasas, Calif.) in a 5% $CO_2$ humidified atmosphere at 37° C. One hundred thousand cells/well were seeded in 24-well plates (Costar, Cambridge, Mass.). Twenty-four hours after plating, the cells were transfected with 0.05 µg DNA per well (for IP production assay) or 0.1 µg DNA per well (for saturation binding studies) using 2 µl lipofectamine in 0.25 ml OPTI-MEM containing 1% DMSO (vehicle) or 1 µg/ml of each indole, quinoline or erythromycin macrolide prepared in vehicle.

After five hours, 0.25 ml of DMEM containing 20% FCS with or without indole, quinoline or erythromycin macrolide (as indicated) was added to each well. The cells were incubated for an additional 18 hours at 37° C., then washed and fresh growth medium with (1 µg/ml) or without the therapeutic agent was added to the cells for another 28 hours at 37° C.

The cells were then washed twice with DMEM/0.1% BSA/Gentamicin and were preloaded with $^3$H-inositol (for IP assays) or DMEM (for internalization studies) for 18 hours prior to stimulation with agonist. During this latter 18 hour period, as well as the period of GnRH stimulation, indole, quinoline and erythromycin macrolide were not present.

The quantification of IP production and saturation binding were determined as described previously (Huckle and Conn, *Methods Enzymol.* 141:149-55, 1987).

To determine the saturation binding, the cells were washed twice with warm DMEM/BSA prior to incubating with the GnRH agonist [$^{125}$I]-buserelin [D-tert-butyl-Ser$^6$, des-Gly$^{10}$, Pro$^9$, ethylamide-GnRH; specific activity, 700 μCi/μg; 230,000 cpm/0.5 ml, pH 7.4; Hoeschst-Roussel Pharmaceuticals (Somerville, N.J.); also see Marian et al., *Mol. Pharmacol.* 19:399-405, 1981] and nonspecific binding was measured in the presence of 1 μM GnRH (NIDDK National Hormone and Peptide Program, Bethesda, Md.). Cells were incubated at room temperature for 90 minutes. The medium was removed, plates containing the cells were placed on ice and washed twice with ice-cold PBS. Then, 0.2 M NaOH/0.1% SDS (Costa et al., *J Clin. Endocrinol. Metab.* 86:2680-6, 2001) was added to the wells to solubilize the cells. The sample was transferred to a glass tube and counted in a gamma counter (Packard Instruments; Downers Grove, Ill.). Specific binding was calculated by subtracting non-specific binding (binding measured in the presence of 1 μM GnRH) from total binding (no GnRH).

To measure inositol phosphates (IP) production, anywhere from 4-51 hours after the start of transfection with WT or mutant GnHRH, transiently transfected COS-7 cells were washed twice with DMEM (no indole, quinoline or erythromycin macrolide) containing 0.1% bovine serum albumin (BSA), and intracellular inositol lipids were incubated in inositol-free DMEM supplemented with 4 μCi/ml [$^3$H]myo-inositol for 18 hours at 37° C. After the preloading period, cells were washed twice with DMEM (inositol free) containing 5 mM LiCl (no indole, quinoline or erythromycin macrolide) and incubated for 2 hours at 37° C. in the absence or presence of the indicated doses of GnRH agonist buserelin dissolved in 0.5 ml DMEM (inositol free)-LiCl. At the end of the incubation period, medium was removed, and 1 ml 0.1 M formic acid was added to each well. Cells were then frozen and thawed to disrupt the cell membranes.

IP accumulation was measured by Dowex anion exchange chromatography and liquid scintillation spectroscopy, as previously described (Huckle and Conn, *Methods Enzymol.* 141: 149-55, 1987). Briefly, 1 ml aliquots of cell lysates were applied to 0.4 ml columns of Dowex 1-X8 (200-400 mesh, formate form). Free [$^3$H]inositol was eluted with 10 bed volumes of water; labeled IP$_1$, IP$_2$, and IP$_3$ with 8 bed volumes each of 0.2, 0.5, and 1.0 M ammonium formate in 0.1 M formic acid, respectively. Radioactivity was determined in the various Dowex fractions by liquid scintillation spectroscopy. Under these chromatographic conditions, [$^3$H]IPs are not eluted from Dowex columns, and can be identified by thin layer chromatography.

The IC$_{50}$ for each indole, quinoline and erythromycin macrolide was calculated as follows. Cells expressing wild-type GnRHR are incubated in the presence of 1 μg/ml of the indole, quinoline or erythromycin macrolide and in the presence of various concentrations of $^{125}$I-buserelin ($10^{-13}$ M-$10^{-7}$M), and the amount of IP production measured as described above. The IC$_{50}$ concentration for the unlabeled indole, quinoline or erythromycin macrolide in a competition experiment is the concentration required to inhibit the radiolabeled ligand ($^{125}$I-buserelin) to the specific ligand binding site of GnRHR by 50%. Although the IC$_{50}$ value can often be visually determined, the most accurate method for determining IC$_{50}$ values is to use non-linear regression analysis using the equation for a sigmoid plot.

$$Y = \text{Bottom} * \frac{(\text{Top} \cdot \text{Bottom})}{(1 - 10^{X \times \log IC50})}$$

where Top is the top of the curve, Bottom is the bottom of the curve; Y is the amount bound (either as cpm or as % of control); and X is the concentration of unlabeled agent. The IC$_{50}$ determined for each agent is shown in the FIGS. 1-3.

Figure 1B:
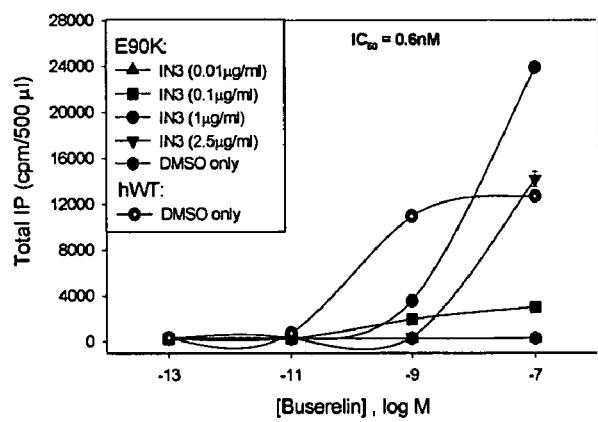
Figure 1C:
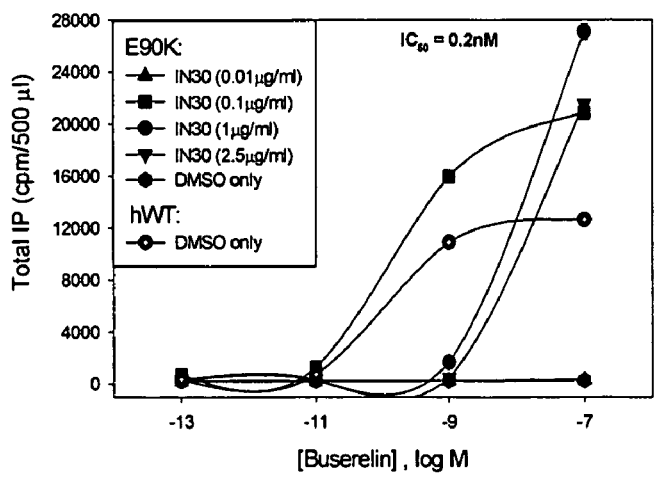
Figure 2A:
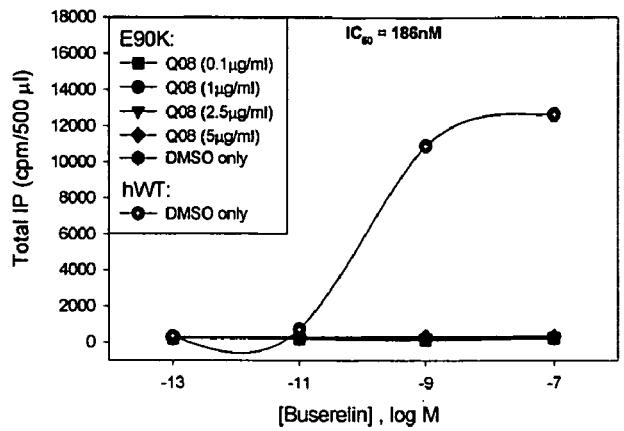
FIGS. 2A-C are graphs showing the efficacy (assessed by IP production) of quinolones (A) Q08, (B) Q76, and (C) Q89, on restoration of function to the GnRHR mutant $E^{90}K$.
Figure 2B:
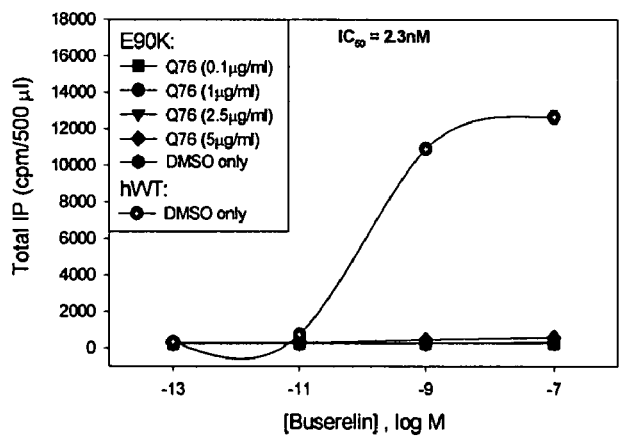
Figure 2C:
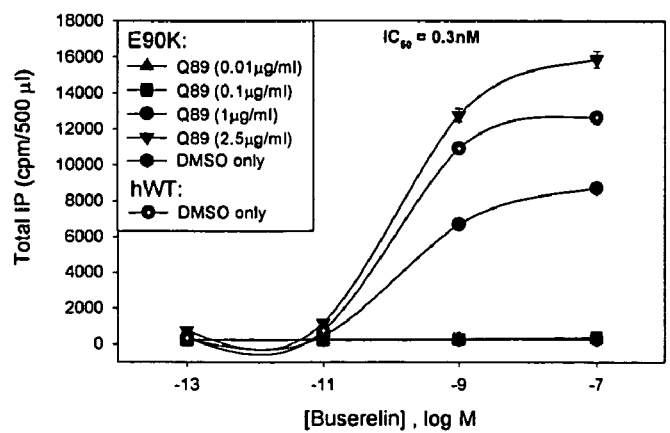
Figure 3A:
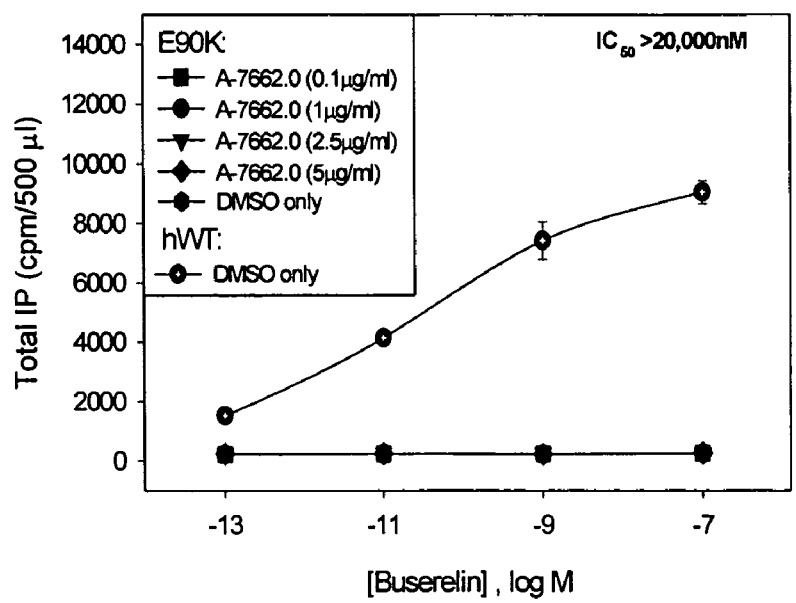
FIGS. 3A-D are graphs showing the efficacy (assessed by IP production) of erythromycin macrolides (A) A-7662.0, (B) A-64755.0, (C) A-177775.0, and (D) A-222509.0, on restoration of function to the GnRHR mutant $E^{90}K$.
Figure 3B:
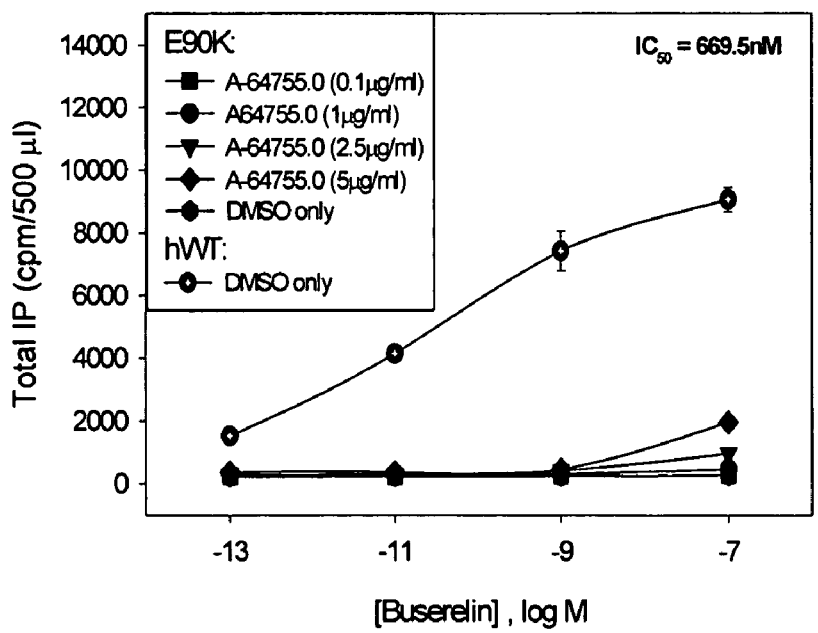
Figure 3C:
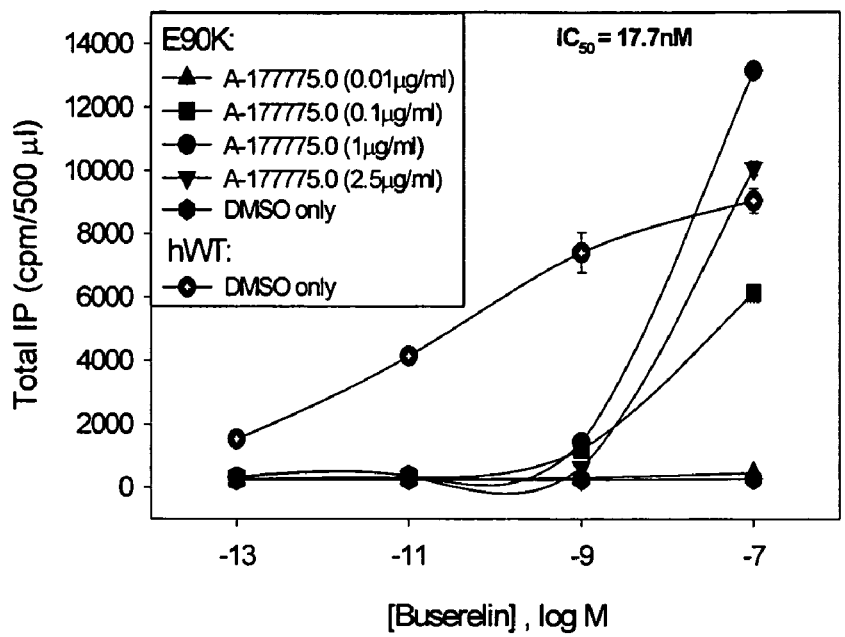
Figure 3D:
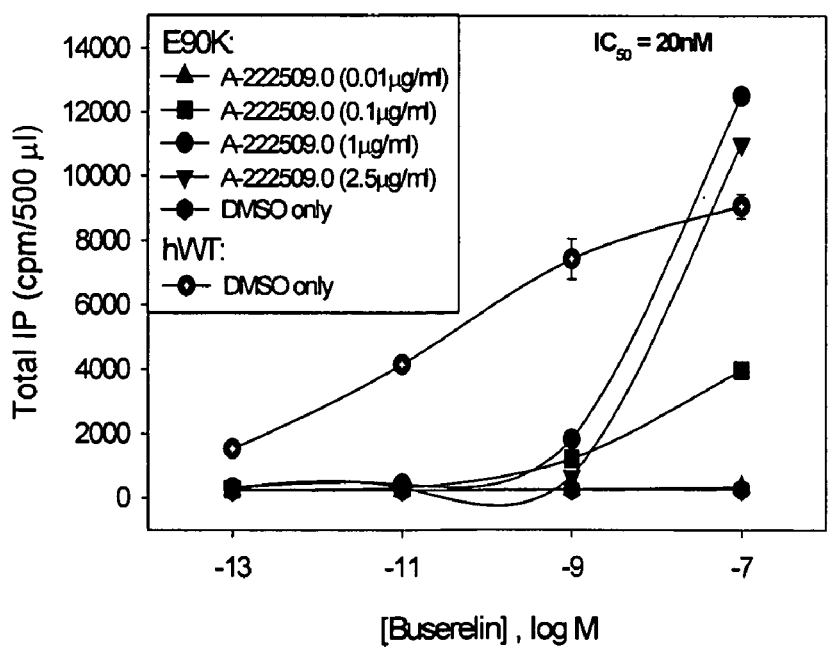
Figure 5:
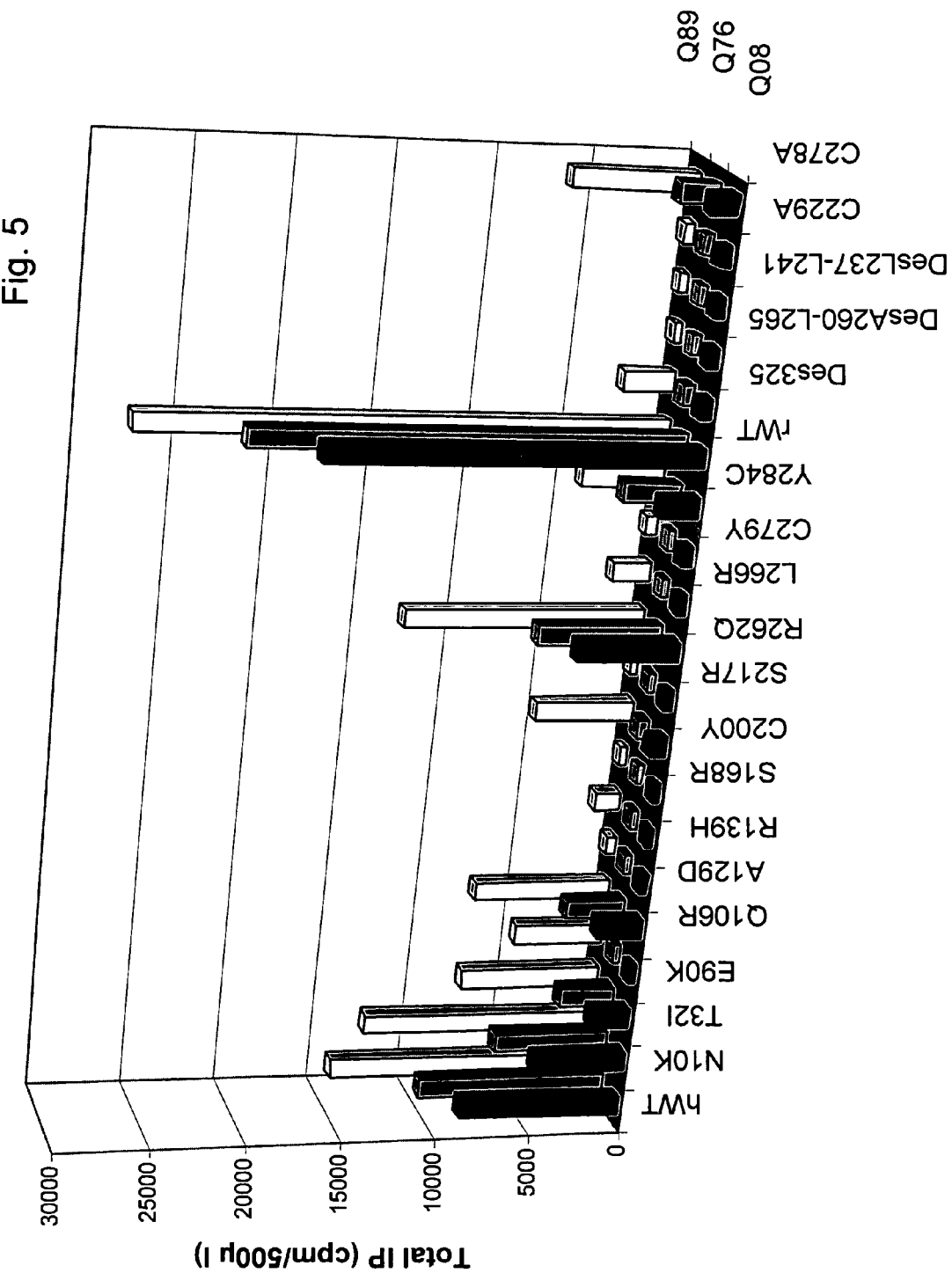
FIG. 5 is a bar graph showing the effect of 1 μg/ml of three quinolones in restoring function to each GnRHR mutant. IP production in the presence of $10^{-7}$ M buserelin is shown. For clarity the SEM bars were omitted. The standard deviation was typically less than 10% of the corresponding mean.
Figure 6:
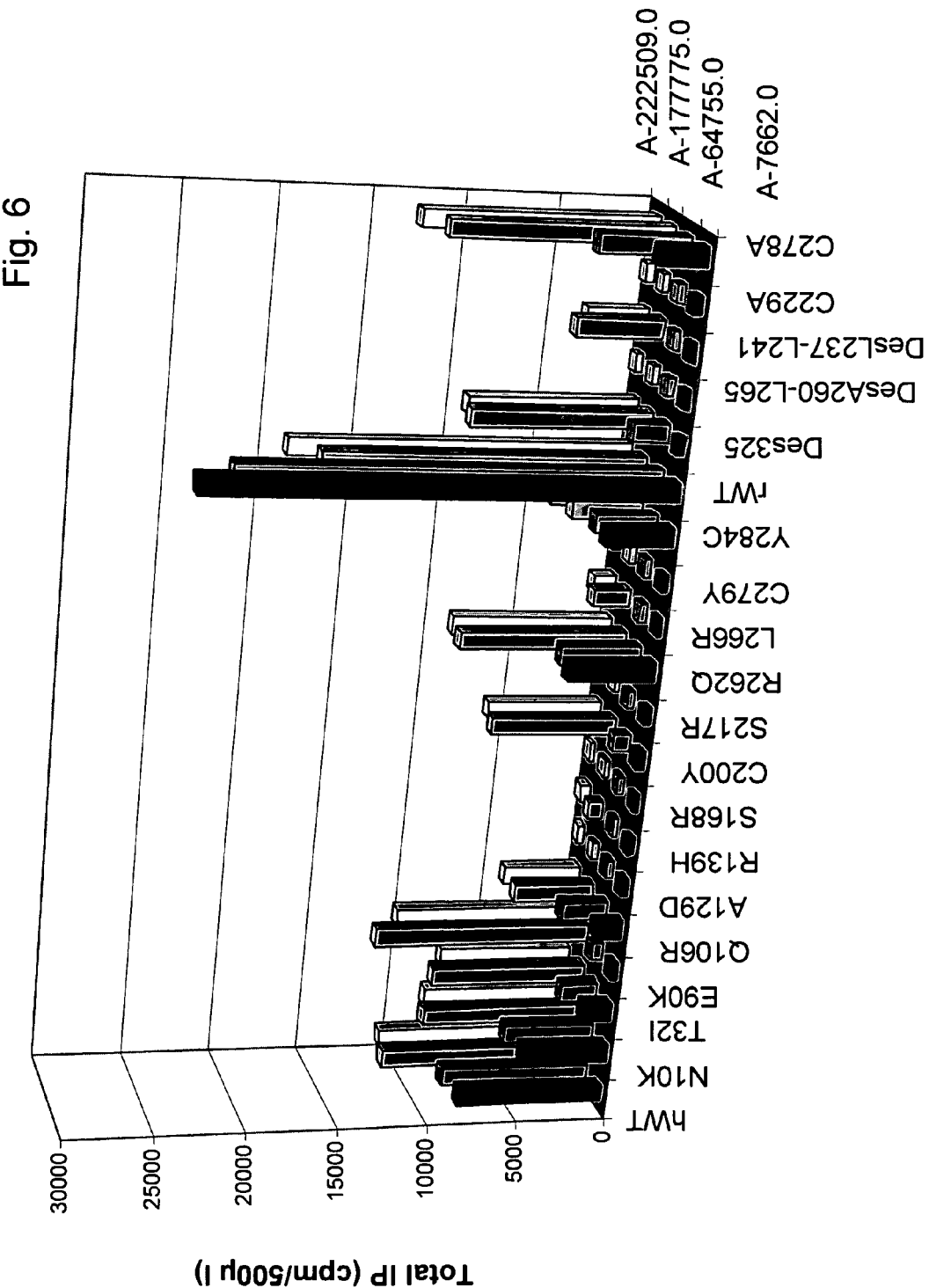
FIG. 6 is a bar graph showing the effect of 1 μg/ml of four erythromycin macrolides in restoring function to each GnRHR mutant. IP production in the presence of $10^{-7}$ M buserelin is shown. For clarity the SEM bars were omitted. The standard deviation was typically less than 10% of the corresponding mean.

FIGS. 1A-C(indoles), 2A-C (quinolones) and 3A-D (erythromycin macrolides) show the efficacy (assessed by IP production) of each agent assayed for restoring function to the E$^{90}$K mutant. The data shown in FIGS. 1-3 are the means±SEM from triplicate determinations. For each chemical class, the data are presented with the lowest IC$_{50}$ value (for the hGnRHR, shown in figures) first. The data indicate that a concentration of 1 μg/ml is, in most cases, the dose of agent that elicits an optimum response.

FIGS. 4 (indoles), 5 (quinolones) and 6 (erythromycin macrolides) show the effect of the 1 μg/ml concentration of each agent in restoring function to each mutant.

Figure 7:
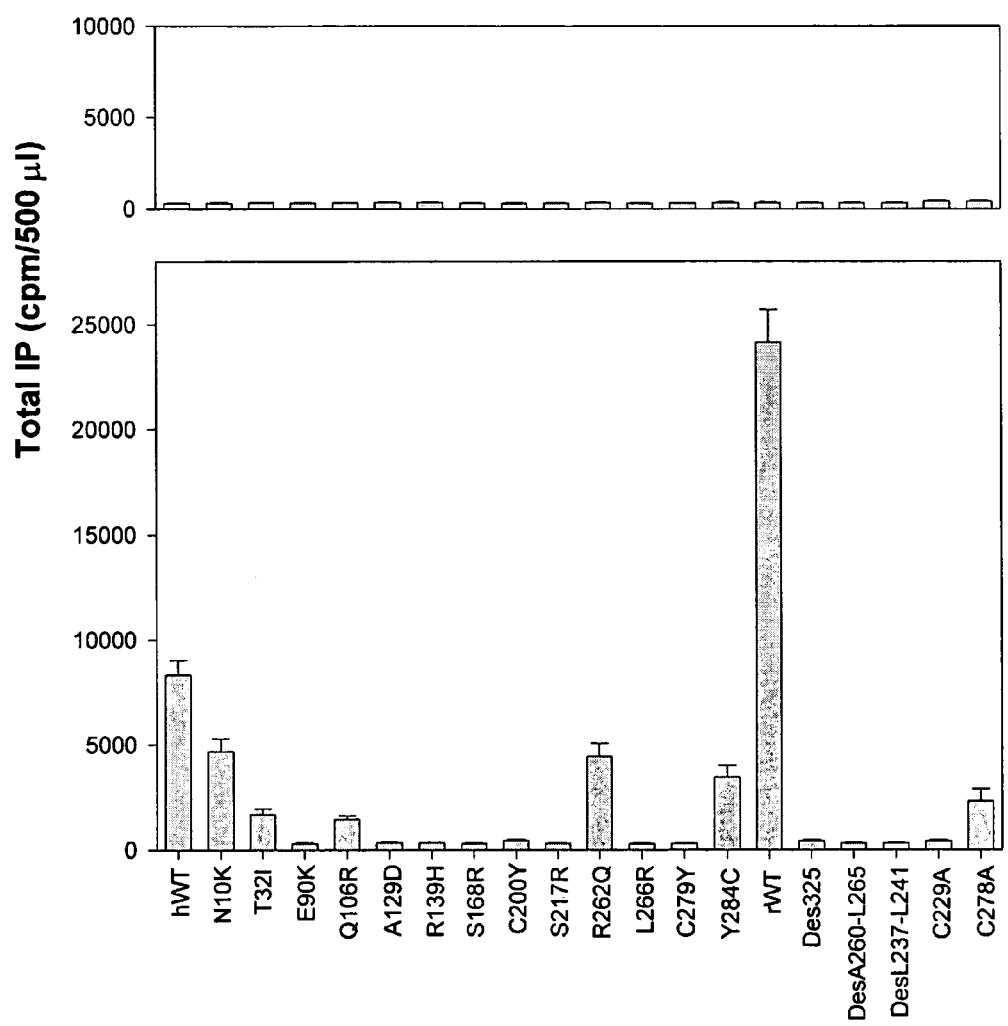
FIG. 7 is a bar graph showing the unrescued (no drug) coupling of receptor in the absence (upper graph) or presence (lower graph) of $10^{-7}$ M buserelin.
Figure 8:
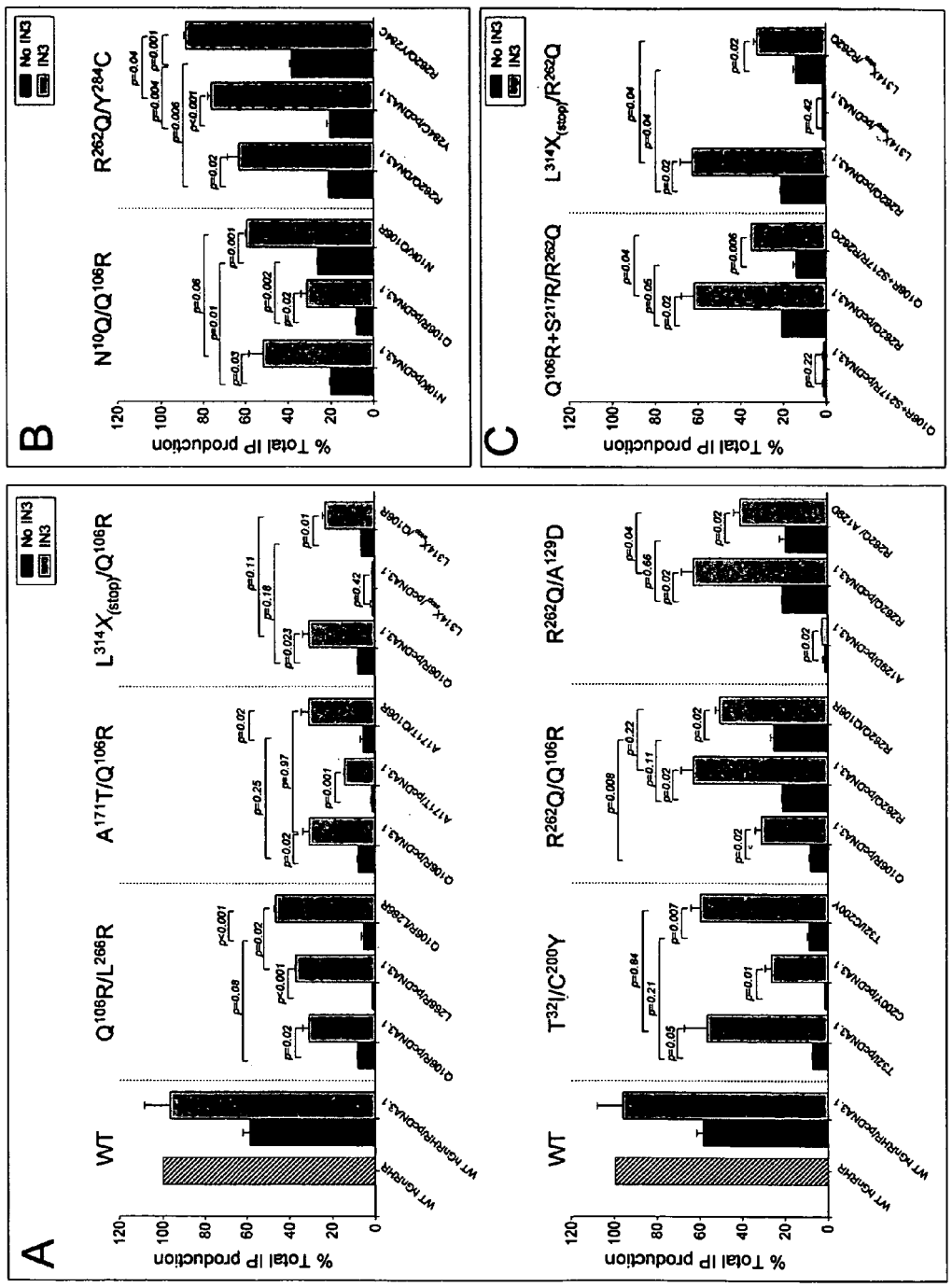
FIGS. 8A-C are bar graphs showing the Buserelin-stimulated ($10^{-7}$ M) IP production in COS-7 cells cotransfected with different heterozygous hGnRHR mutants or the empty vector at a 1:1 ratio, (A) WT hGnRHR as compared to the hGnRHR $Q^{106}R/L^{266}R$ mutation, $A^{171}T/Q^{106}R$ mutation, $L^{314}X_{(stop)}/Q^{106}R$ mutation, $T^{32}I/C^{200}Y$ mutation, $R^{262}Q/Q^{106}R$ mutation, or $R^{262}Q/A^{129}D$ mutation, (B) the hGnRHR $N^{10}Q/Q^{106}R$, or $R^{262}Q/Y^{284}C$ mutation, and (C) the hGnRHR $Q^{106}R+S^{217}R/R^{262}Q$, or $L^{314}X_{(stop)}/R^{262}Q$ mutation, and cultured in the absence or presence of IN3. Data are expressed as the percent of maximal IP production relative to that exhibited by control cells transfected with 0.050 μg of the WT hGnRHR cDNA (set as 100%).

For reference, FIGS. 7 and 8 show the unrescued coupling of the receptor in the absence (FIG. 7) or presence (FIG. 8) of $10^{-7}$ M buserelin, a GnRHR agonist. The member of each drug class with the lowest affinity for the human GnRHR is oriented closest to the viewer.

EXAMPLE 2

Pharmacological Rescue of Compound GnRHR Mutations

This example describes methods used to demonstrate that mutant GnRH receptor (GnRHR) pairs associated with compound heterozygous patients can be rescued with a pharmacoperone. Although this example describes particular use of IN3 to rescue compound mutations, those skilled in the art will appreciate that other pharmacoperones specific for GnRHR will have similar effects.

Nine pairs of GnRHR mutants and an unreported combination (L$^{314}$X$_{(stop)}$/R$^{262}$Q) were examined (Table 1). Mutations in the hGnRHR isolated from subjects with HH are widely distributed across the entire sequence of the protein. Six homozygous and 10 compound heterozygous combinations of hGnRHR mutants have been described in individuals exhibiting either partial or complete forms of HH. Some mutants are completely non-functional (E$^{90}$K, A$^{129}$D, R$^{139}$H, S$^{168}$R, A$^{171}$T, C$^{200}$Y, S$^{127}$R, L$^{266}$R, C$^{279}$Y, P$^{320}$L, and L$^{314}$X$_{stop}$) while others retain a variable degree of function (N$^{10}$K, N$^{10}$K+Q$^{11}$K, T$^{32}$I, Q$^{106}$R, R$^{262}$Q, and Y$^{284}$C) (Karges et al., *Hum. Reprod. Update* 6:523-30, 2003; Ulloa-Aguirre et al., *Hum. Reprod. Update* 10:177-92, 2004). Mutations may alter any of several functions of the molecule including ligand binding, effector coupling or receptor expression at the cell surface. Patients with hGnRHR mutations (either homozygotes or compound heterozygotes) may exhibit a broad spectrum of phenotypes, ranging from complete to partial hypogonadism (Karges et al., *Hum. Reprod Update* 6:523-30, 2003; Ulloa-Aguirre et al., *Hum. Reprod. Update* 10: 177-92, 2004; Leaños-Miranda et al., *J. Clin. Endocrinol. Metab.* 88:3360-7, 2003).

TABLE 1

Genotype/phenotype relationships of the compound heterozygous HH subjects bearing the hGnRHR mutations examined

| Genotype | Phenotype |
|---|---|
| $R^{262}Q/Q^{106}R$ | Partial (♀ and ♂) or complete (♀) |
| $R^{262}Q/Y^{284}C$ | Complete |
| $Q^{106}R + S^{217}R/R^{262}Q$ | Complete (♂) or partial (♀) |
| $R^{262}Q/A^{129}D$ | Complete (♂ and ♀) |
| $L^{314}X_{stop}/Q^{106}R$ | Complete (♀) |
| $T^{32}I/C^{200}Y$ | Complete (♂) |
| $Q^{106}R/L^{266}R$ | Partial (♀) |
| $N^{10}K/Q^{106}R$ | Partial or complete (♂ and ♀) |
| $A^{171}T/Q^{106}R$ | Complete (♂) |

Wild-type and mutant hGnRHR cDNAs were subcloned into pcDNA3.1 at KpnI and XbaI restriction enzymes sites. All hGnRHR mutants were constructed by overlap extension PCR (Ashton et al., Bioorg. Med. Chem. Lett. 11:1727-31, 2001); the double hGnRHR $Q^{106}R/S^{217}R$ variant was synthesized using the $Q^{106}R$ mutant as template. For transfection, large-scale plasmid DNAs were prepared using an Endofree maxiprep kit (QIAGEN, Valencia Calif.). The identity of all constructs and the correctness of the PCR-derived sequences were verified as previously described (Leaños-Miranda et al., Misrouted proteins as a novel disease etiology and therapeutic target: rescue of hypogonadotropic hypogonadism-causing and manufactured mutants as a proof of principle, in Kumar, R., Ed Molecular Endocrinology: Methods and Protocols, Humana Press, 2003).

Wild-type hGnRHR and mutant receptors were transiently expressed in COS-7 cells using standard molecular biology techniques (Janovick et al., J. Pharmacol. Exp. Ther. 305: 608-614, 2003). Fifty thousand cells/well were plated in 48-well plates (Costar, Cambridge, Mass.). Twenty-four hours later, the cells were transfected or co-transfected with 0.05 μg/well total cDNA (0.025 μg of each hGnRHR mutant cDNA or pcDNA3.1 empty vector, as indicated) for inositol phosphates (IP) production or with 0.2 μg total cDNA per well (0.1 μg of each hGnRHR mutant cDNA or empty vector, as indicated) for [$^{125}$I]-Buserelin binding, using 1 μl Lipofectamine in 0.125 ml OPTI-MEM. After 5 hours, 0.125 ml of DMEM containing 20% FCS was added to each well. The cells were incubated for an additional 18 hours at 37° C., and then washed with fresh growth medium and incubated for another 4 hours at 37° C. The cells were then washed twice with DMEM/0.1% BSA/gentamicin and preloaded with [$^3$H] myo-inositol (for IP assays) or DMEM (for binding studies) as described below. IP production was measured following exposure of the cells to the GnRH agonist, buserelin for 2 hours.

Treatment with IN3 (Merck Research Laboratories, Rahway, N.J.) was performed as follows. Cultured COS-7 cells were transiently transfected with hGnRHR cDNA solutions containing either 1% DMSO (vehicle) or 1 μg/ml IN3 prepared in vehicle, as previously described (Maya-Núñez et al., J. Clin. Endocrinol. Metab. 87:2144-2149, 2002; Janovick et al., J. Clin. Endocrinol. Metab. 87:3255-3262, 2002; herein incorporated by reference). Cells were continuously exposed to the antagonist during the period of transfection and thereafter until the start of the [$^3$H]myo-inositol or DMEM 18 hour preloading periods.

Quantification of IP production by Dowex anion exchange chromatography and liquid scintillation spectroscopy was performed as described in Example 1. The receptor binding assay was performed as described in Example 1. Briefly, COS-7 cells were transiently transfected as described above. Twenty-seven hours after the start of transfection, the cells were washed twice with warm DMEM/BSA/HEPES and cultured in DMEM for 18 hours before the addition of [$^{125}$I]-Buserelin (specific activity, 700 μCi/μg, ~$10^6$ cpm/0.5 ml, pH 7.4). Cells were incubated at room temperature for 90 minutes in the presence or absence of excess (1 μM) GnRH plus $^{125}$I-Buserelin. Thereafter, the medium was removed, the plates containing the cells were placed on ice, washed twice with ice-cold PBS, and then the cells were solubilized by the addition of 0.2 M NaOH/0.1% SDS. Aliquots of samples were then transferred to glass tubes and counted in a gamma counter (Packard Instruments, Downers Grove, Ill.). Specific binding was calculated by subtracting non-specific binding (binding measured in the presence of 1 μM GnRH) from total binding (no GnRH added).

The IP3 results shown are the means±SEM from representative experiments from three or more independent experiments in triplicate incubations. Non-paired or paired Student's t tests were employed for comparisons between-groups, as appropriate. In all experiments, the standard deviation was typically less than 10% of the corresponding mean, except at basal levels in which the cpm were low. A two-tailed P value<0.05 was considered statistically significant.

GnRH agonist-stimulated IP production in COS-7 cells expressing individually the WT or the mutant hGnRHRs is shown in FIGS. 8 and 9A-C. The $N^{10}K$, $T^{32}I$, $Q^{106}R$, $R^{262}Q$ and $Y^{284}C$ hGnRHR mutants partially responded to Buserelin stimulation, whereas in the $Q^{106}R+S^{217}R$, $A^{129}D$, $A^{171}T$, $C^{200}Y$ and $L^{314}X_{(stop)}$ mutants, agonist-stimulated IP production was virtually abolished. Addition of 1 μg/ml IN3 resulted in variable degrees of functional rescue; cells expressing $N^{10}K$, $T^{32}I$, $R^{262}Q$, and $Y^{284}C$ mutants showed a significant increase in Buserelin-stimulated IP production, which was similar to that exhibited by the WT receptor in the absence of IN3. A modest pharmacological rescue was observed for $Q^{106}R$, $C^{200}Y$, and $L^{266}R$ mutant receptors, whereas lower, but significant rescue was shown for $A^{129}D$ and $A^{171}T$ hGnRHR variants. IN3 had no detectable effect on the double $Q^{106}R+S^{217}R$ mutant and the $L^{314}X_{(stop)}$ truncated receptor. Buserelin-stimulated IP production by cells bearing the WT hGnRHR was increased by the addition of IN3. Radioligand binding correlated well with the IP production assays (FIGS. 9D-F).

Figure 9:
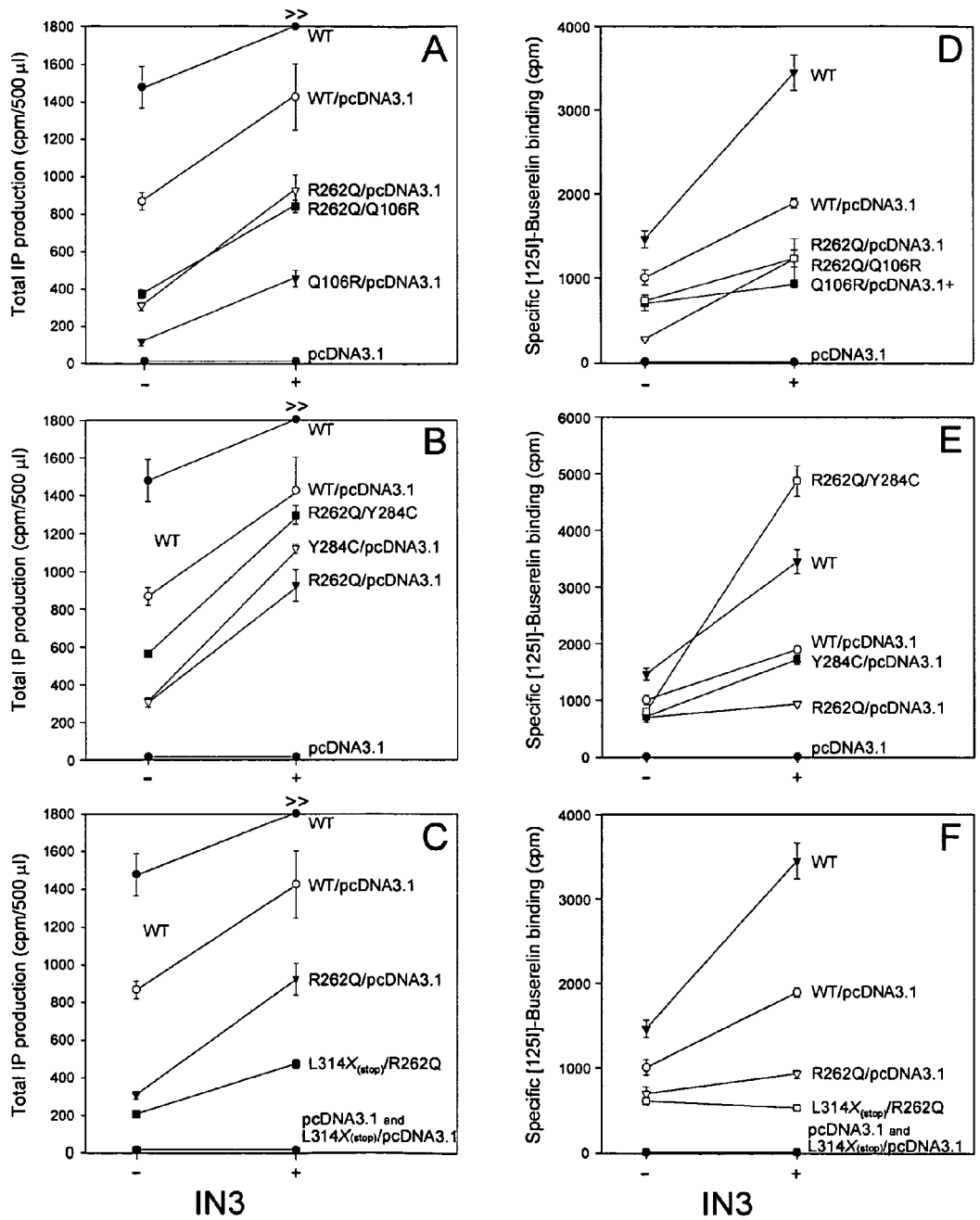
FIGS. 9A-F are graphs showing the Buserelin-stimulated ($10^{-7}$ M) (A-C) maximal IP production and (DE) specific [$^{125}$I]-Buserelin binding (mean±SEM) in COS-7 cells transiently expressing the $R^{262}Q$, $Q^{106}R$ and $R^{262}Q/Q^{106}R$ (A and D), $R^{262}Q$ $Y^{284}C$ and $R^{262}Q/Y^{284}C$ (B and E), and $L^{314}X_{(stop)}$, $R^{262}Q$ and $L^{314}X_{stop}/R^{262}Q$ (C and F) naturally occurring mutant hGnRHRs. IP production and ligand binding shown by cells transfected with 0.050 μg of the WT hGnRHR (WT) is shown. The results are representative of at least three independent experiments (A-C) or the mean of triplicate determinations (D-F).

As shown in FIGS. 8 and 9, coexpression of each pair of mutants in COS-7 cells led to variable Buserelin-provoked IP effects. COS-7 cells were cotransfected with equal amounts of each mutant hGnRHR cDNA as presented (and presumably expressed) by compound heterozygous HH patients. As shown in FIG. 8, coexpression of each pair of hGnRHR mutants resulted in GnRH agonist-provoked IP responses that were classified into three groups: i) Active predominant effect (the combination of mutants yielded similar responses to agonist stimulation as did the more active of the two mutants cotransfected individually with the empty vector alone: $Q^{106}R/L^{266}R$, $A^{171}T/Q^{106}R$, $L^{314}X_{(stop)}/Q^{106}R$, $T^{32}I/C^{200}Y$, $R^{262}Q/A^{129}D$, and $R^{262}Q/Q^{106}R$ mutant hGnRHR); ii) Additive effect (the combination of each pair of mutants produced an effect similar to the sum of the single mutants cotransfected with the empty vector $N^{10}Q/Q^{106}R$ and $R^{262}Q/Y^{284}C$ hGnRHR pairs), and iii) Dominant negative effect (the response of a single mutant was attenuated by the companion mutant: $Q^{106}R+S^{217}R/R^{262}Q$ and $L^{314}X_{(stop)}/R^{262}Q$ GnRHRs).

For all combinations, addition of IN3 increased both agonist binding and effector coupling. The response to IN3 was similar ($N^{10}Q/Q^{106}R$, $R^{262}Q/Q^{106}R$, $A^{171}T/Q^{106}R$, $T^{32}I/C^{200}Y$, and $L^{314}X_{(stop)}/Q^{106}R$), higher ($R^{262}Q/Y^{284}C$ and $Q^{106}R/L^{266}R$) or lower ($R^{262}Q/A^{129}D$, $Q^{106}R+S^{217}R/R^{262}Q$, and $L^{314}X_{(stop)}+R^{262}Q$) compared to the response exhibited by the less affected mutant in the presence of the IN3. Representative examples of agonist-stimulated IP production and [$^{125}$I]-Buserelin binding in response to IN3 are shown in FIG. 9. Based on these results, the clinical phenotype in patients expressing complex heterozygous alleles appears to be dictated both by the contribution from each mutant and by a dominant negative effect similar to that reported for mutants and wild-type receptor.

Figure 10:
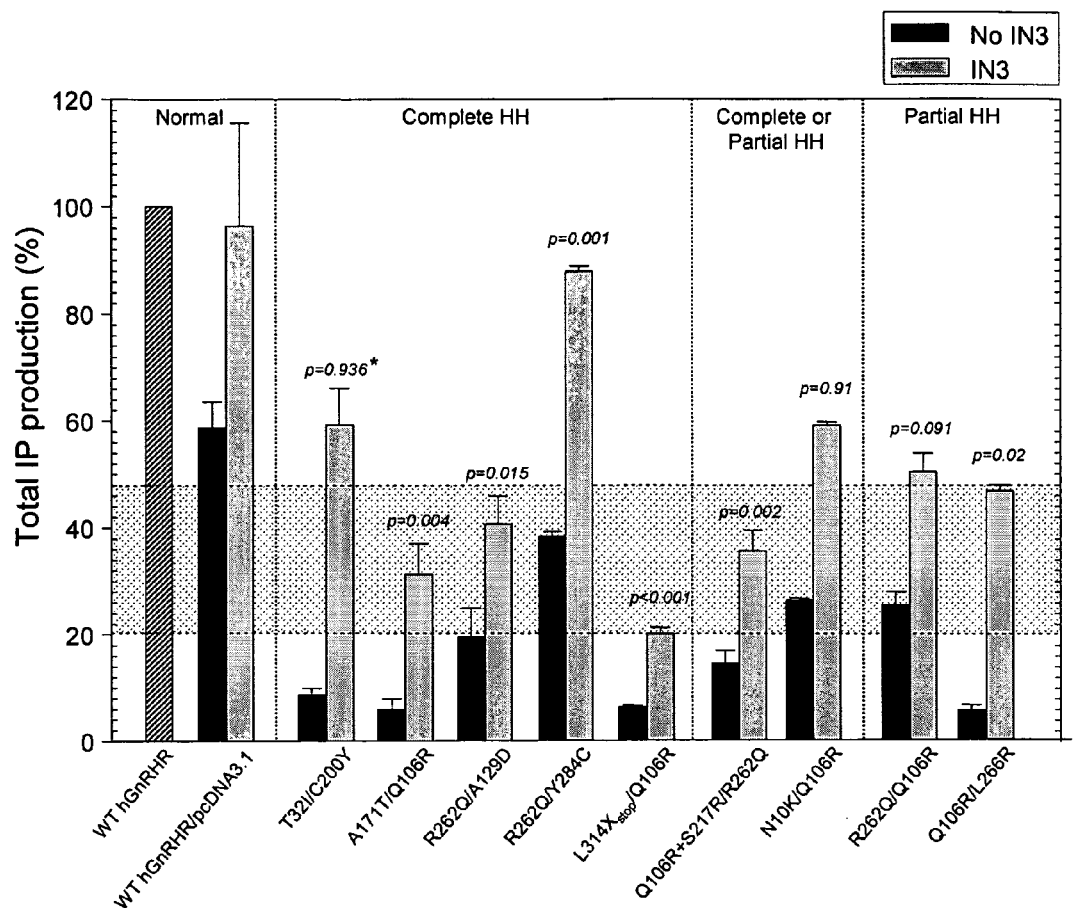
FIG. 10 is a bar graph showing the maximal Buserelin-stimulated IP production in COS-7 cells coexpressing different hGnRHR mutant combinations separated according to the clinical phenotype reported in HH patients (maximal IP production in cells transfected with 0.050 μg of the WT hGnRHR cDNA is taken as 100%). Cells were cultured in the absence (black bars) or presence (gray bars) of IN3. The upper discontinuous horizontal line is set at −2 SD of the maximal Buserelin-stimulated IP production from cells cotransfected with the WT hGnRHR and the empty vector, and cultured in the absence of IN3, whereas the lower horizontal line denotes −2 SD of the mean maximal IP production exhibited by the coexpression of the heterozygous hGnRHR mutants leading to complete or partial ($N^{10}K/Q^{106}R$) or to partial ($R^{262}Q/Q^{106}R$) forms of HH. The shaded area delimits the functional level of hGnRHR mutants that upon pharmacological rescue would predict partial correction of the HH; levels above this area would lead to complete recovery and restoration of a normal phenotype, whereas levels below the area would predict complete or nearly complete failure to pharmacological rescue. Values above gray bars indicate the level of significance vs WT hGnRHR/pcDNA3.1 No IN3.

FIG. 10 compares the total IP production of the WT hGnRHR with the different pairs of mutant hGnRHRs in the absence or presence of IN3 and grouped according to the clinical phenotypes reported in HH patients (Table 1). In the case of the $T^{32}I/C^{200}Y$ and $R^{262}Q/Q^{106}R$ combinations (both leading to complete forms of HH), functional rescue of the hGnRHR was completely achieved by IN3 treatment, whereas in the $A^{171}T/Q^{106}R$ and $R^{262}Q/A^{129}D$ mutations (also leading to complete HH) agonist-provoked IP production (following IN3) was below 2 standard deviations (SD) compared to that evoked by the WT hGnRHR coexpressed with the empty vector, but above 2 SD of the mean activity exhibited by $N^{10}K/Q^{106}R$ and $R^{262}Q/Q^{106}R$ combinations (which lead to partial HH) (shaded area in FIG. 10).

The $L^{314}X_{(stop)}/Q^{106}R$ receptor pair was not significantly rescued by IN3, reflecting both the severity of the truncation in receptor function imposed by the truncated hGnRHR and its negative effect on the $Q^{106}R$ receptor mutant (FIG. 10). Likewise, pharmacological rescue of the mutant $Q^{106}R+S^{217}R/R^{262}Q$ combination (which leads to sex-dependent complete or partial forms of HH) was similar to that by the $A^{171}T/Q^{106}R$; in the former combination, the $Q^{106}R+S^{217}R$ exerted a dominant negative effect on the $R^{262}Q$ mutant both in the absence or presence of the pharmacoperone (FIG. 10), whereas in the case of the latter mutant, the $A^{171}T$ mutation leads to complete receptor inactivation.

IN3 effected complete ($N^{10}K/Q^{106}R$ and $R^{262}Q/Q^{106}R$ receptor mutants) or nearly complete ($Q^{106}R/L^{266}R$ mutant) rescue of the three hGnRHR mutant combinations known to cause partial forms of HH in compound heterozygous individuals (FIG. 10).

Without wishing to be bound to a particular theory, possible explanations for this disparity of responses might include: i) the mutants coexpressed did not interfere with one another's function (such as $T^{32}I/C^{200}Y$, $N^{10}Q/Q^{106}R$, and $R^{262}Q/Y^{284}C$), despite the potentially strong negative effects that one of the mutants (such as hGnRHR $C^{200}Y$) may exert on its pair. The coexpressed mutant hGnRHRs might even interact with each other to counteract any intrinsic functional impairment of the mutants, allowing the complex to reach levels of function similar to those found for the WT receptor in response to IN3 treatment (such as the $R^{262}Q/Y^{284}C$ mutant pair); ii) the mutants interact with each other, with one of the mutants exerting dominant negative effects on the other in the case in which the net response was less than expected under conditions of pharmacological rescue ($A^{171}T/Q^{106}R$ and $Q^{106}R/L^{266}R$ mutants). In this case, interaction between the mutant receptors may potentially impede the complex to attain normal function in response to IN3, and iii) the mutants interact with each other and exert dominant negative effects on hGnRHR function, significantly reducing the function of the complexed receptors either in the absence and/or presence of IN3 (such ash $Q^{106}R+S^{217}R^{262}Q$ and $R^{262}/A^{129}D$ pairs and the unreported $L^{314}X_{(stop)}/R^{262}Q$ combination) or precluding, in some instances, that a given pair with one mutant highly sensitive to pharmacological rescue may reach the expected response to pharmacoperone treatment (such as the $R^{262}Q/Q^{106}R$ receptor combination).

It is possible that in addition to the potential differential effects that some hGnRHR mutants may exert on signal transduction, the dominant negative effects imposed by one of the defective heterozygous receptors might also impact on the extent of clinical response to pharmacological rescue. For example, with the hGnRHR $R^{262}Q/A^{129}D$ and $Q^{106}R+S^{217}R/R^{262}Q$ genotypes, expression of the hGnRHR $A^{129}D$ and $S^{217}R$ alleles may preclude the $R^{262}Q$ receptor to attain normal function in response to IN3; subjects bearing this genotype would respond partially to pharmacoperone treatment (FIG. 10). Likewise, in the $L^{314}X_{(stop)}/Q^{106}R$ genotype, expression of the former allele would prevent the $Q^{106}R$ receptor mutant to be pharmacologically rescued to the expected levels (~30%), leading to a poor clinical response to pharmacoperone therapy. In the case of the $T^{32}I/C^{200}Y$ and $R^{262}Q/Y^{284}C$ mutants and all three genotypes leading to partial HH ($N^{10}Q/Q^{106}R$, $R^{262}Q/Q^{106}R$ and $Q^{106}R/L^{266}R$), the potential interactions between mutant receptor would not affect, or might even favor, the clinical response to pharmacoperone treatment; in these cases, a complete clinical response may be achieved (FIG. 10).

These results demonstrate that treatment of subjects can be achieved by determining the mutation present in the subject, and selecting an appropriate therapy. This is more fully discussed in Examples 5 and 6. Briefly, those subjects having a mutation shown to be effectively rescued by a pharmacoperone can be administered the pharmacoperone, while subjects having a mutation shown to be not effectively rescued by a pharmacoperone can be administered another therapy for the disorder.

As shown in FIG. 10, treatment with the pharmacoperone IN3 also increased the expression level of WT hGnRHR. This observation indicates that a large portion (nearly 50%) of the WT hGnRHR is intentionally inefficiently processed by the cell, retained in the ER and eventually degraded by the proteasome. Incompletely processed receptors may function as a reserve pool of molecules that can be called upon when needed quickly (such as when exposed to IN3).

EXAMPLE 3

Internalization of Rescued Receptors

This example describes methods that can be used to determine whether a receptor can traffic to the cell surface and bind ligand, and then be internalized. Some wild-type receptors traffic to the cell surface, bind ligand, and then internalize along with the bound ligand. When such receptors are mutated, this can affect trafficking of the receptor to the cell surface, thereby decreasing the amount of receptor-ligand complex internalized. Therefore, agents that can rescue this defect can be identified by determining whether in the presence of a test agent, the amount of receptor internalized increases. Such a method can be therefore be used to screen agents for their ability to restore function to mutant receptors.

Although a particular example is presented for determining an amount of GnRHR internalization in the presence of a potential therapeutic agent, such as a GnRHR antagonist, the disclosure is not limited to this receptor. For example, similar methods can be used to determine whether a mutant rhodopsin receptor, mutant insulin receptor, mutant LDL receptor or mutant alpha I anti-tryspsin receptor is internalized (and thus rescued) in the presence of a test agent. In such examples, the appropriate ligand can include a label that permits detection of the internalized receptor.

In examples where the GnRHR is used, cells can be transfected with mutant or wild-type GnRHR as described in Example 1. In some examples, 12 well plates were used and $2 \times 10^5$ cells were plated per well, thereby allowing each plate to serve as one time point. The agent, such as a GnRHR antagonist or vehicle alone is incubated as described in Example 1 for the IP assay (Example 2). Following transfection, a radioligand acid wash method (Marian et al., *Mol. Pharmacol.* 19:399-405, 1981; Heding et al., *Endocrinology* 141:299-306, 2000) is used to measure internalization of the mutant or WT human GnRHRs. This method distinguishes internalized and non-internalized receptor. Briefly, cells are washed twice with 0.5 ml DMEM containing 0.1% BSA, then incubated with [$^{125}$I]-buserelin (see Example 1). At the desired time, the iodinated ligand is removed and the plate placed on ice. Cells are washed twice with 0.5 ml ice cold PBS, then 0.5 ml acid wash solution (50 mM acetic acid and 150 mM NaCl, pH 2.8) is added to each well and incubated for 12 minutes on ice.

To determine the surface-bound iodinated ligand, the acid wash is collected and counted on a Packard gamma counter (Downers Grove, Ill.). To determine the internalized radioligand-receptor complex, the cells are solubilized in 0.5 ml PBS containing 0.1% Triton-X100, collected and counted. Nonspecific binding for all conditions is determined using the same method but in the presence of 10 µM unlabeled GnRH. Nonspecific binding is subtracted from the surface-bound and internalized radioligand, and the amount of internalized radioligand is expressed as the percent internalized of the total bound at each time point.

EXAMPLE 4

Indole, Quinolone, and Macrolide Mimetics

Also disclosed are biologically active, non-peptide organic molecules that mimic the action of the indoles, quinolones, and macrolides described in Example 1 that can restore function to a GnRHR mutant protein, such as a GnRHR protein containing an N10K, T321, E90K, Q106R, A129D, R139H, C200Y, R262Q, L266R, C279Y, or Y284C substitution, or combinations thereof. The ability of a mimetic of the indoles, quinolones, and macrolides described in Example 1 to restore function to a GnRHR mutant can be determined using the methods disclosed herein.

A person of ordinary skill in the art will appreciate that certain structural changes can be made to compounds of the present disclosure, as long as such structural changes do not alter the biological activity of the indoles, quinolones, and macrolides disclosed herein, that is, their ability to restore function to GnRHR mutants. For example, the indole derivative IN3 includes a number of alkyl substituents, specifically methyl groups, such as the gem dimethyl groups and the methyl group at the chiral center adjacent to the indole. These alkyl substituents may vary in length and position on the molecule, and typically are selected from the group consisting of lower (such as ten carbon atoms or fewer) aliphatic groups, more particularly lower alkyl groups, including straight and branched chains, as well as all biologically active stereoisomers. Also, the methyl groups of the 3,5-dimethylbenzene ring can be varied to be other lower aliphatic groups, most likely lower alkyl groups, and the relative positioning of such lower aliphatic groups can be other than 3,5. Additionally, the number of lower aliphatic groups can vary from 1-5.

Moreover, IN3 includes an amide functionality, and such amide can vary from the [2.2.2]bicycloaminooctane moiety of IN3. For example, other cyclic compounds, as well as acyclic amides, may be included. Also, with reference to such amides, the carbonyl oxygen can be replaced with other heteroatoms, most notably sulfur. Also the nitrogen atom of the heterocyclic amines also can vary, and potentially can be replaced with an atom selected from the group consisting of oxygen and sulfur. Furthermore, regioisomers of the oxygen, nitrogen and sulfur heterocycles can replace the heterocyclic amine moieties. Thus, the indole moiety may be replaced by fused bicyclic aromatic moieties, such as benzimidazole, benzofuran, and benzothiophene derivatives. Particular aromatic heterocycles are selected from the group consisting of furan, pyrrole, thiophene, oxazole, imidazole, thiazole, quinoline, isoquinoline, pyrimidine, purine, benzofuran, benzothiophene, and derivatives thereof. The hydrogen atom bonded to the nitrogen atom of the aliphatic amine also can be replaced with lower aliphatic substituents, with such substituents typically being selected from the group consisting of lower alkyl groups, with methyl groups being a likely such substituent. The substitution pattern of the pyridine derivative can be varied, for example a 2-pyridine or a 3-pyridine derivative can be used in place of the 4-pyridine moiety of IN3. Additionally, the pyridine moiety can be replaced with another aromatic group, such as a five membered, six membered, or fused aromatic heterocycle. Finally, the number of methylene units spacing particular functional groups and moieties of IN3 can be varied. For example, IN3 includes 2 methylene units that space the amine portion of IN3 from the pyridine ring. The number of methylene units may vary from about 1-10, more typically from about 2-5.

EXAMPLE 5

Dominant-Negative Effects by GnRHR Mutants

This example describes methods used to demonstrate that some GnRHR mutations observed in patients with HH can exert a dominant-negative (DN) effect on the human wild-type GnRHR, due to oligomerization and retention in the ER.

To determine the residue(s) responsible for the loss of dominant negativity by the rWT GnRHR, mouse and rat homologs of the dominant negative human mutant $E^{90}K$, along with WT and other HH mutants in which combinations of the four non-conservative changes were made (mouseXXrat: P11Q, I24T, I160T, and G216S, where XX is the amino acid sequence position). The role of a primate-specific amino acid ($Lys^{191}$) that is inserted in the human GnRHR sequence and is associated with a decrease in the proportion of the human GnRHR that is routed to the plasma membrane, was determined.

Cells were cultured using the methods described in Example 1. For tranfections, $5 \times 10^4$ COS-7 cells were plated in 0.25 ml growth medium in 48 well Costar cell culture plates. Twenty-four hours after plating, the cells were washed once with 0.5 ml OPTI-MEM (Promega, Madison, Wis.) then transfected with 100 ng total cDNA (pcDNA3.1+without insert "empty vector" was included to bring the total cDNA to 100 ng/well, unless otherwise indicated) and 1 µl lipofectamine in 0.125 ml OPTI-MEM (room temperature), according to manufacture's instructions. For co-transfection, the cells were co-transfected with WT GnRHR (5 ng/well) and empty vector or mutant GnRHR (95 ng/well) or other GPCR cDNAs, as indicated, using 1 µl Lipofectamine (Promega, Madison, Wis.) in 0.125 ml Opti-MEM. Constant amounts of Opti-MEM were achieved by the addition of sterile milli-Q H2O to the cDNA mixtures. The total amount of DNA transfected remained constant, as complementary amounts of empty pcDNA3.1+(empty vector), were included in the transfection mixture. After five hours, 0.125 ml DMEM with 20% FCS and 20 µg/ml gentamicin was added to the wells. Twenty-three hours after transfection the medium was removed and replaced with 0.25 ml fresh growth medium.

The IP production was measured 27 hours after transfection, as described in Example 1, except that following the preloading, cells were treated for 2 hours in 0.25 ml of Buserelin (100 nM), and at the end of the incubation period, the cells were frozen and thawed in the presence of 0.5 ml of 0.1 M formic acid. Data ($n \geq 3$) was analyzed with one-way ANOVA and then paired Student's t-test (SigmaStat 3.0, Jandel Scientific Software, Chicago, Ill.; $P<0.05$ was considered significant).

Figure 12:
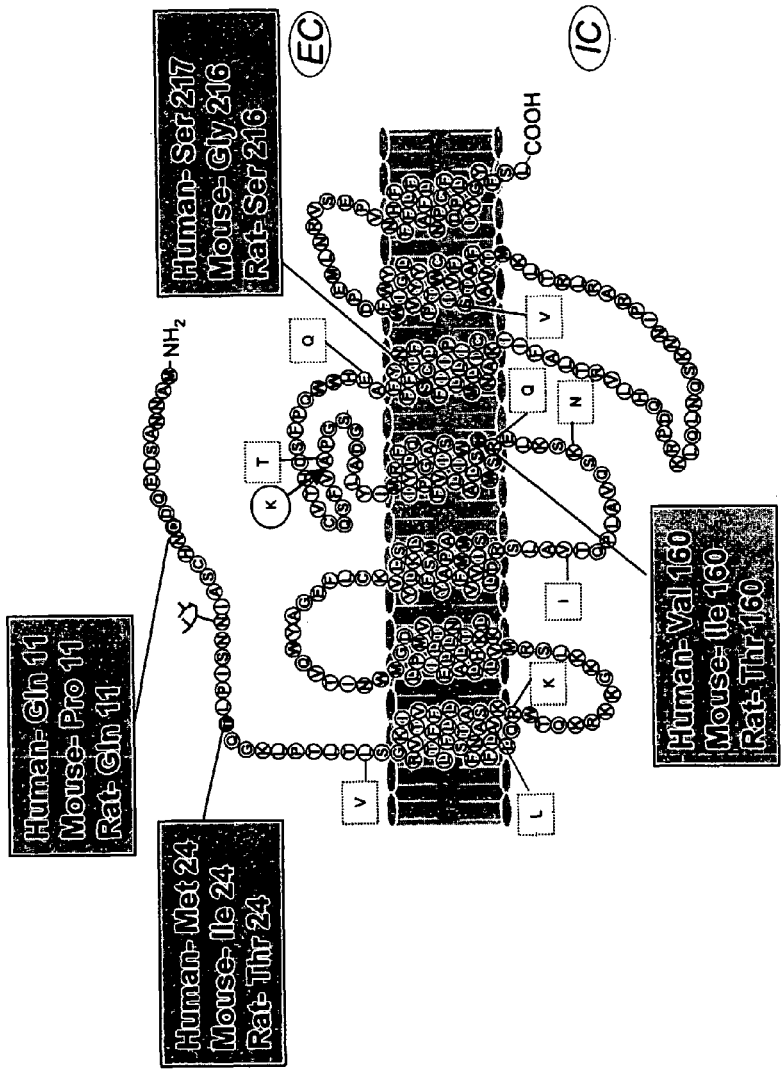
FIG. 12 is a schematic diagram showing the four semi- or non-conservative locations in mouse and rat GnRHR (SEQ ID NO: 2). Of the thirteen amino acid residue differences between mouse and rat GnRHR sequences, there are nine conservative differences (small boxes with single letter shows the mouse substitution) and four non-conservative differences. The non-conservative locations (amino acids 11, 24, 160, and 216) are shown by shaded boxes that also compare the human, mouse and rat substitutions at those positions. Evolutionary insertion of primate-specific Lys191 (site shown by circle and arrow) to the human GnRHR results in amino acid 217 corresponding to amino acid 216 in the mouse and rat GnRHR sequence. The large box compares the human, mouse and rat sequence in the fifth transmembrane sequence, (amino acids 200-249 of SEQ ID NO: 2), showing position 216/217 in bold. The extracellular (EC) and intracellular (IC) plasma membrane orientation is shown.

FIG. 12 shows the rat GnRHR sequence, indicating the four positions of non-conservative mutations between the rat and mouse sequence (shaded boxes: mouseXXrat: P11Q, I24T, I160T, and G216S, where "XX" is the amino acid position). The amino acid at each of the four positions in the human sequence is also shown for comparison (shaded boxes). Conservative substitutions compared with the mouse sequence at shown in the small unshaded boxes. The human GnRHR also contains an "extra" amino acid, Lys191 (circle, site of insertion shown by an arrow) that is absent in the all pre-primate species sequenced to date. The sequences for the fifth transmembrane domain of the three species are shown.

Figure 13:
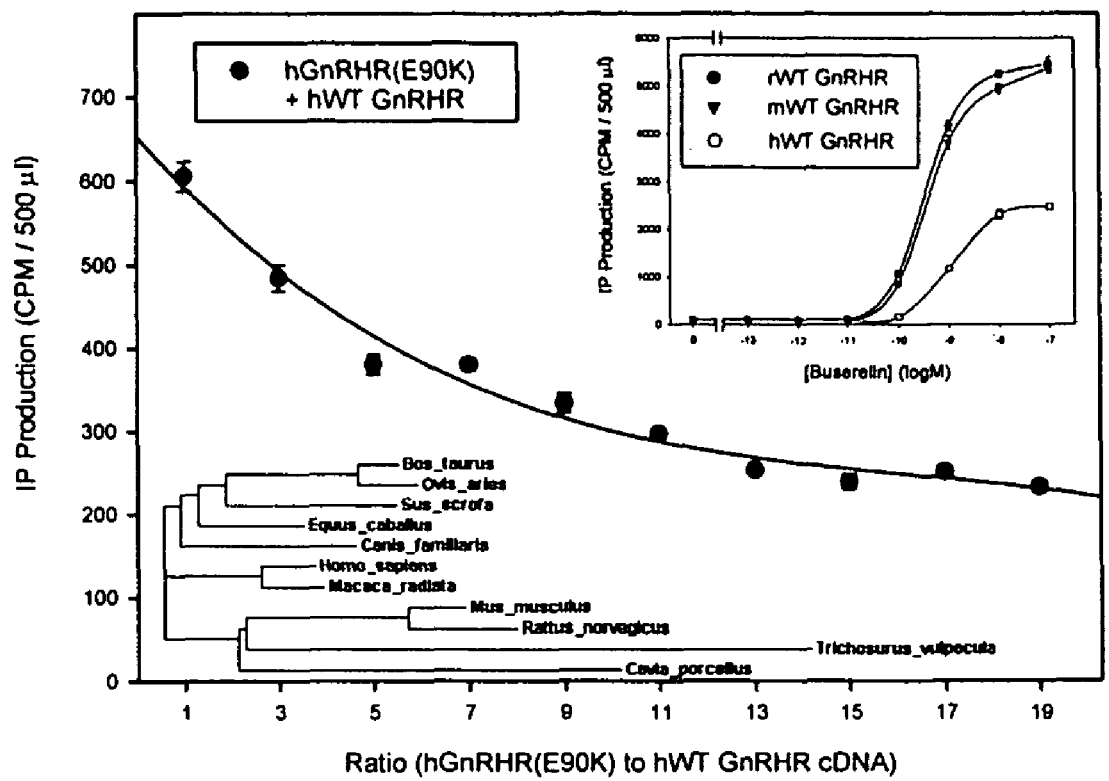
FIG. 13 is a graph showing the dominant negative action of GnRH mutants. Upper inset: WT hGnRHR transfected and treated with 0 to $10^{-7}$ M Buserelin; IP response is maximal in response to $10^{-7}$ M Buserelin. Data are expressed as mean±SEM. The phylogram, showing the relationship between the GnRHR from human, mouse, rat and other species was produced from reported protein sequences.

The maximal response on IP production in cells transfected with 100 ng of WT hGnRHR, occurred with $10^{-7}$ M of the GnRH agonist Buserelin (FIG. 13, inset). For this reason that amount was used for this example. FIG. 13 demonstrates the dominant negative effect of the hGnRH mutant $E^{90}K$ on function of the human WT GnRHR. Although the dominant negative effect of human $E^{90}K$ on human WT is measurable at a mutant:WT ratios of less than 19:1, a higher ratio was used to pronounce the effect in vivo, each cell in a human heterozygote (mutant:WT) would likely express those genes equally, a condition that may not occur when equal amounts of vectors are transfected into cells in vitro. Further, since heterozygotic patients expressing highly dominant-negative mutants would likely be infertile, such mutations would have been selected against and those that appear in the population would be among the least severe in this regard. Accordingly, higher ratios were used.

Figure 14:
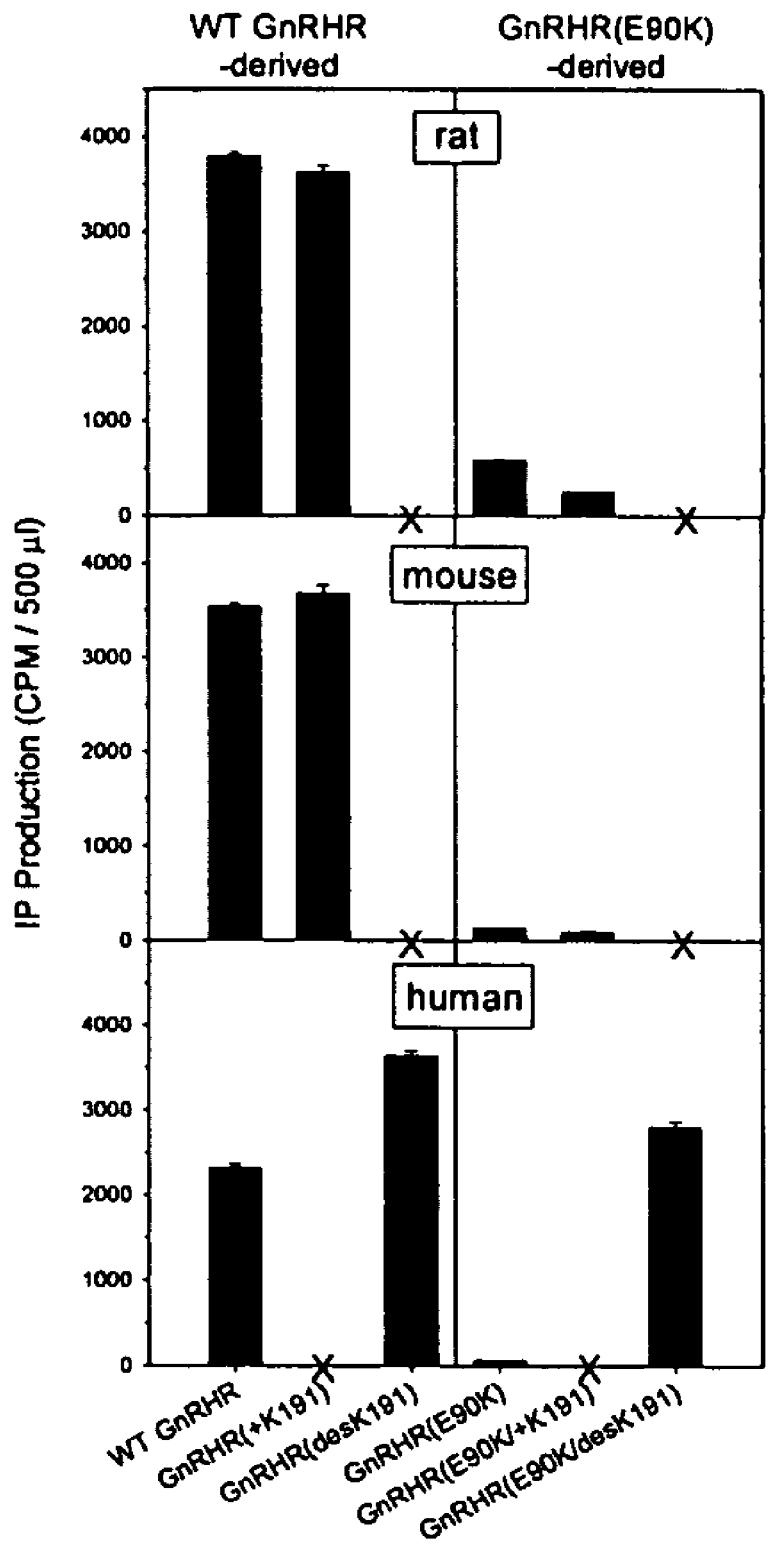
FIG. 14 is a bar graph showing the IP production in response to rat, mouse, and human WT GnRHR and mutants substituted with E90K, and +/des $Lys^{191}$ mutants, alone or in combination. When 100 ng of empty vector was transfected and treated similarly, the result was 73.7±1.3 cpm and was indistinguishable from that measured with hGnRHR(E90K). Columns marked with an "X" denote a GnRHR sequence identical to the individual species WT sequence.

FIG. 13 also shows a phylogram constructed from the reported sequences of GnRHRs and the relationship between rat, mouse and human receptors. The mGnRHR sequence is closer to the human sequence than the rGnRHR, indicated by the shorter line length. The relative amount of IP production for mouse, rat and human, WT and the $E^{90}K$ mutant of the GnRHR are shown in FIG. 14. IP production was used as an indication of receptor-effector coupling. IP production accurately reflects plasma membrane expression of these moieties. In addition, the effect of inserting this amino acid into rat and mouse WT and $E^{90}K$-derived sequences was determined.

As shown in FIG. 14, removal of $K^{191}$ from human GnRHR increases expression of both the WT and mutant $E^{90}K$ forms of the receptor, since this amino acid normally precludes complete expression of the receptor at the plasma membrane. Mouse WT GnRHR was not affected by the $K^{191}$ insertion, while the rat mutant showed modestly decreased plasma membrane expression when the $K^{191}$ was present. In both rodent sequences, expression of $E^{90}K$ mutants was reduced by the $K^{191}$ insertion. The rat GnRHR($E^{90}K$) mutant expresses 15.06% (±0.32% SEM) compared to the WT, followed by very modest expression of the mouse GnRHR ($E^{90}K$) mutant (3.59%+0.20% SEM) compared to the WT. The human $E^{90}K$ mutant was indistinguishable from a "vector only" control.

Figure 15:
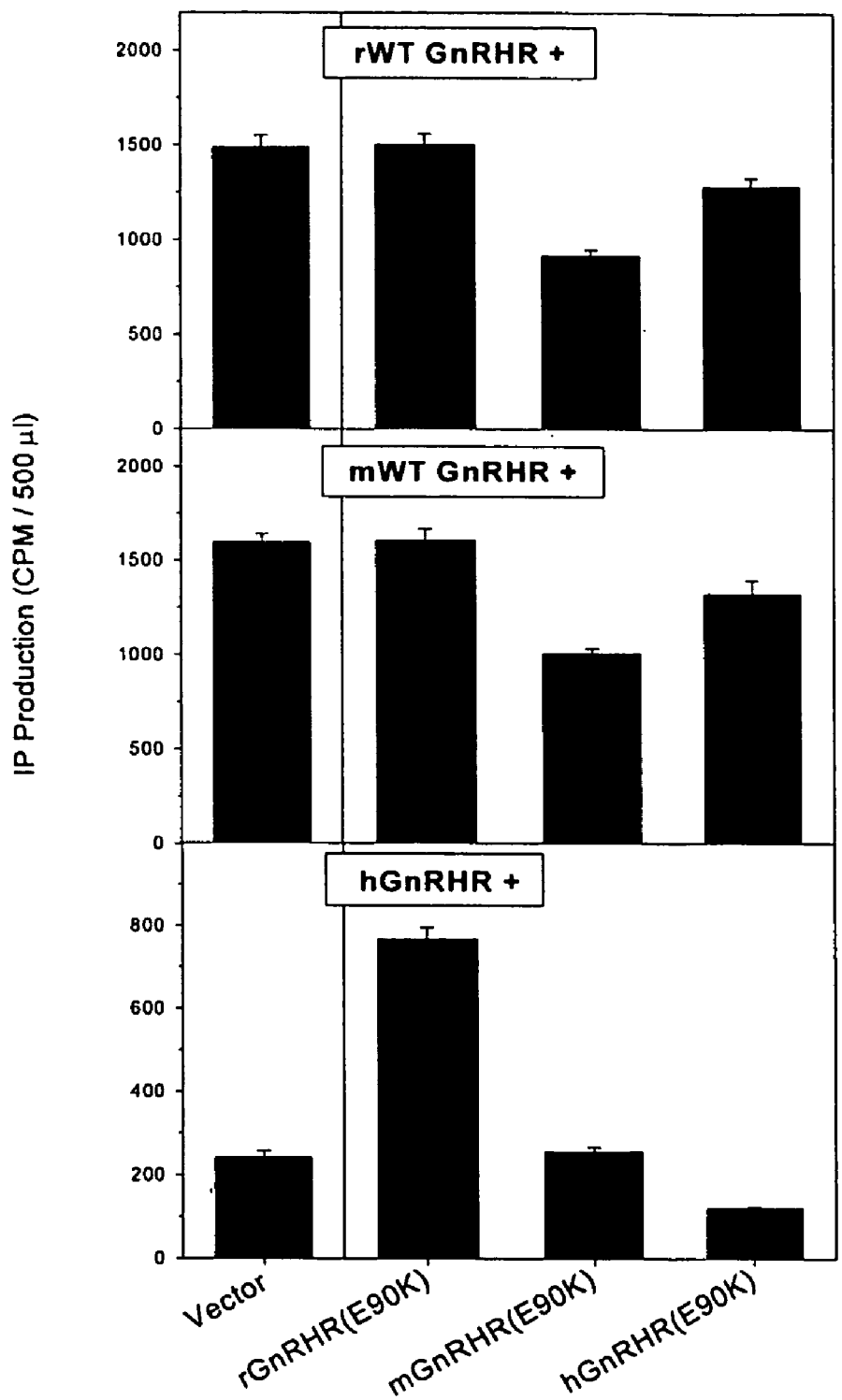
FIG. 15 is a bar graph showing the specificity of rat, mouse, and human E90K mutants to exert a dominant negative effect on WT receptors from these species. Data are mean cpm per 500 ul sample, showing SEM. Transfection with 100 ng of empty vector (not shown) produced 81.4±2.9 CPM.

The species specificity of the rat, mouse, and human GnRHRs modified at $E^{90}K$ to exert a dominant-negative effect on the WT receptor from each of the three species is shown in FIG. 15. As shown in FIG. 15, the rat $E^{90}K$:rat WT pair does not show dominant negativity, although both mouse $E^{90}K$ and human $E^{90}K$ GnRHR mutants show dominant-negative activity with the rat WT. This observation indicates that these human and mouse mutants are still able to interact with the rat WT, and that the difference in the rat (compared to human or mouse) is not due to loss of the ability to oligomerize. The human mutant was more effective as a dominant-negative regulator of the human WT and the mouse mutant is more effective in actions on both rodent WT receptors.

Figure 16:
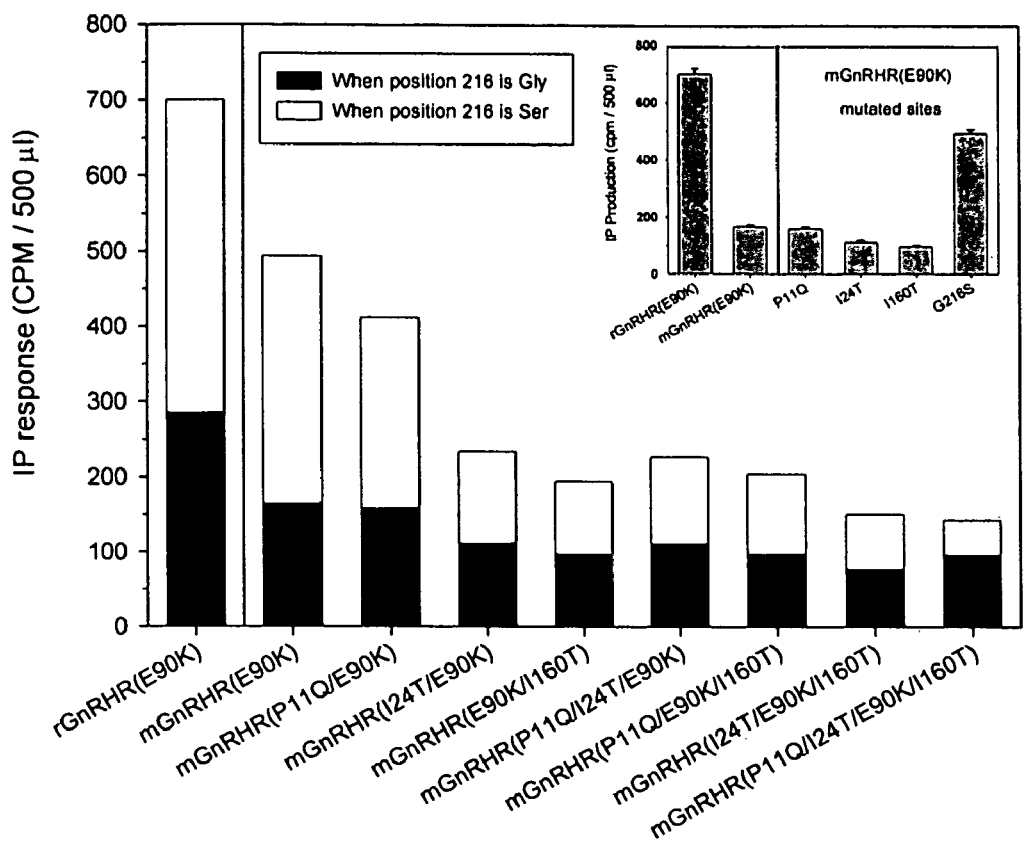
FIG. 16 is a bar graph showing the results of modification in the mouse GnRH sequence at sites corresponding to the differences found in the rat sequence. The inset figure shows the effect of individually mutating the four non-conservative site differences between mouse and rat WT receptors (amino acids 11, 24, 160 and 216) in the mouse E90K sequence. Data are presented as mean CPM±SEM per 500 ul sample. 100 ng of empty vector (not shown) produced 71.0±0.9 CPM. Multiple mutants were created in the mouse E90K sequence with the naturally occurring G216 sequence (front row, main image) and the mutant G216S mutant (rear row, main image) and IP production was assessed following transfection (100 ng DNA). For comparison the rat (normally S216) and mouse E90K (normally G216) sequence are shown on the left of the main image. Note that this difference in the naturally occurring sequence means that the rat WT is in the rear and the mouse WT is in the front row.

Each of the four semi- or non-conservative amino acid changes (between the rodent species) were made singly in the mouse GnRHR($E^{90}K$) sequence to make it more "rat-like." As shown in FIG. 16 (inset), individual modification of three of these residues resulted in no significant change in IP production; however the substitution mGnRHR($E^{90}K/G^{216}S$) markedly increased plasma membrane expression of the mouse (double) mutant. This interspecific construct had about 75% of the activity of the rat GnRHR($E^{90}K$). As shown in FIG. 16, modification of the rat GnRHR($E^{90}K$) sequence to make it more "mouse-like" ($S^{216}G$) resulted in a 2-fold loss of plasma membrane expression. Progressive modification of the remaining three semi- or non-conservative sites in the mouse GnRHR($E^{90}K$) sequence (with either G216S or $G^{216}$) resulted in a loss of plasma membrane expression, indicating a role for the conservative substitutions in the sequence (FIG. 15).

Figure 17:
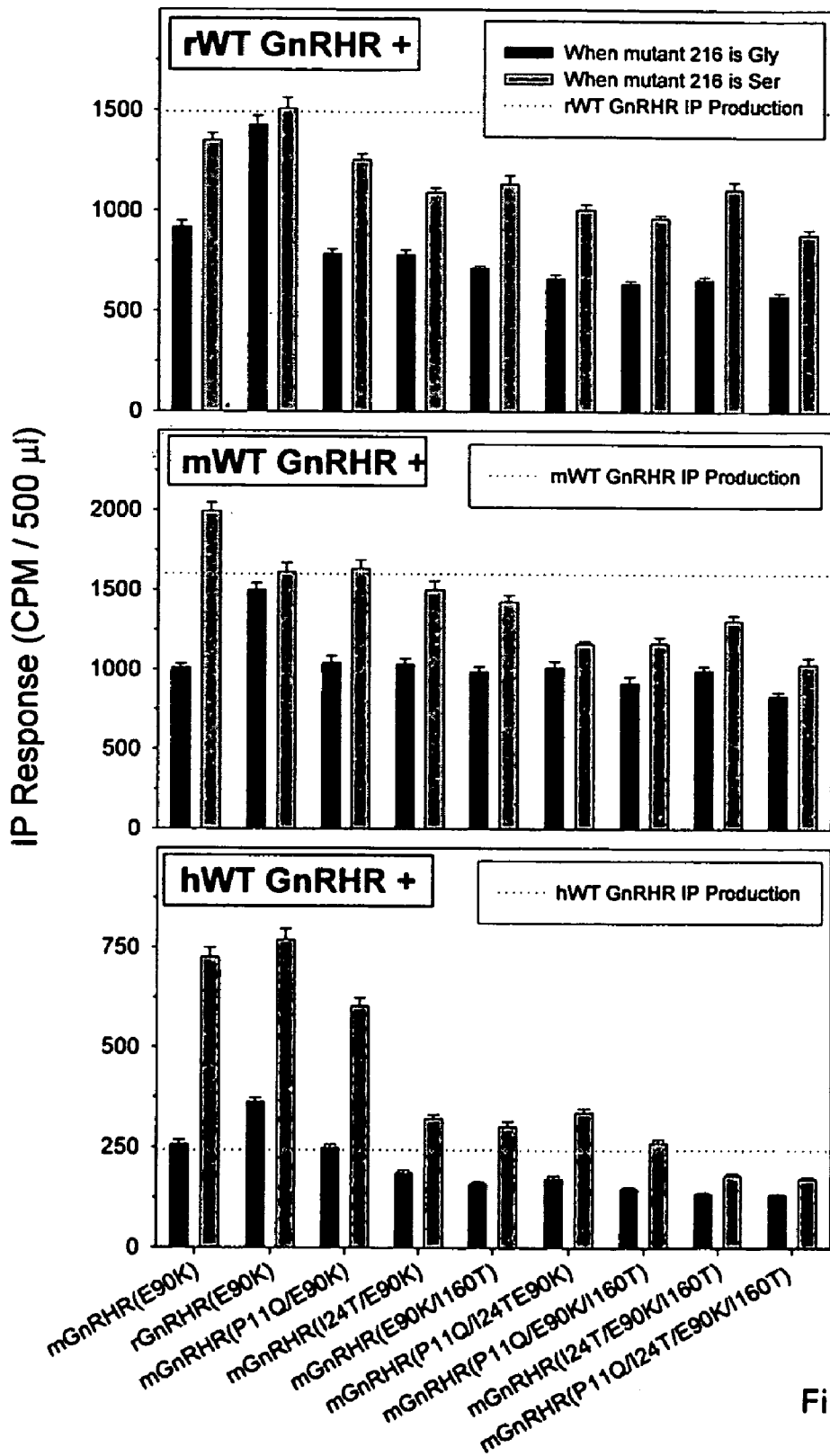
FIG. 17 a bar graph showing the results on IP production of co-transfecting rat, mouse or human WT receptors with mouse E90K bearing double, triple, and quadruple mutants. Rat, mouse, and human WT sequences shown on the x-axis contain the native 216 amino acid ($S^{216}$ for rat and human, and $G^{216}$ for mouse), the only modifications (seen on the y-axis) were to the mouse E90K sequences that were co-transfected with WT and the rat E90K sequence. Data are presented as mean CPM±SEM per 500 ul sample. 100 ng of empty vector produced 81.4±2.9 CPM.

FIG. 17 shows the co-transfection of rat, mouse, and human WT GnRH receptors with mouse GnRHR($E^{90}K$) mutants in which the four rat-specific amino acids were altered singly or in combination. When mouse GnRHR ($E^{90}K$) sequences contain the $G^{216}S$ mutation, the result is a loss in the ability of the mutant mouse sequence to produce a dominant-negative effect on WT GnRHR. When other "rat" mutants are created that result in making the mouse GnRHR ($E^{90}K$) sequence more "rat-like", the dominant-negative effect is also lost whenever the $G^{216}S$ substitution is present.

Figure 18:
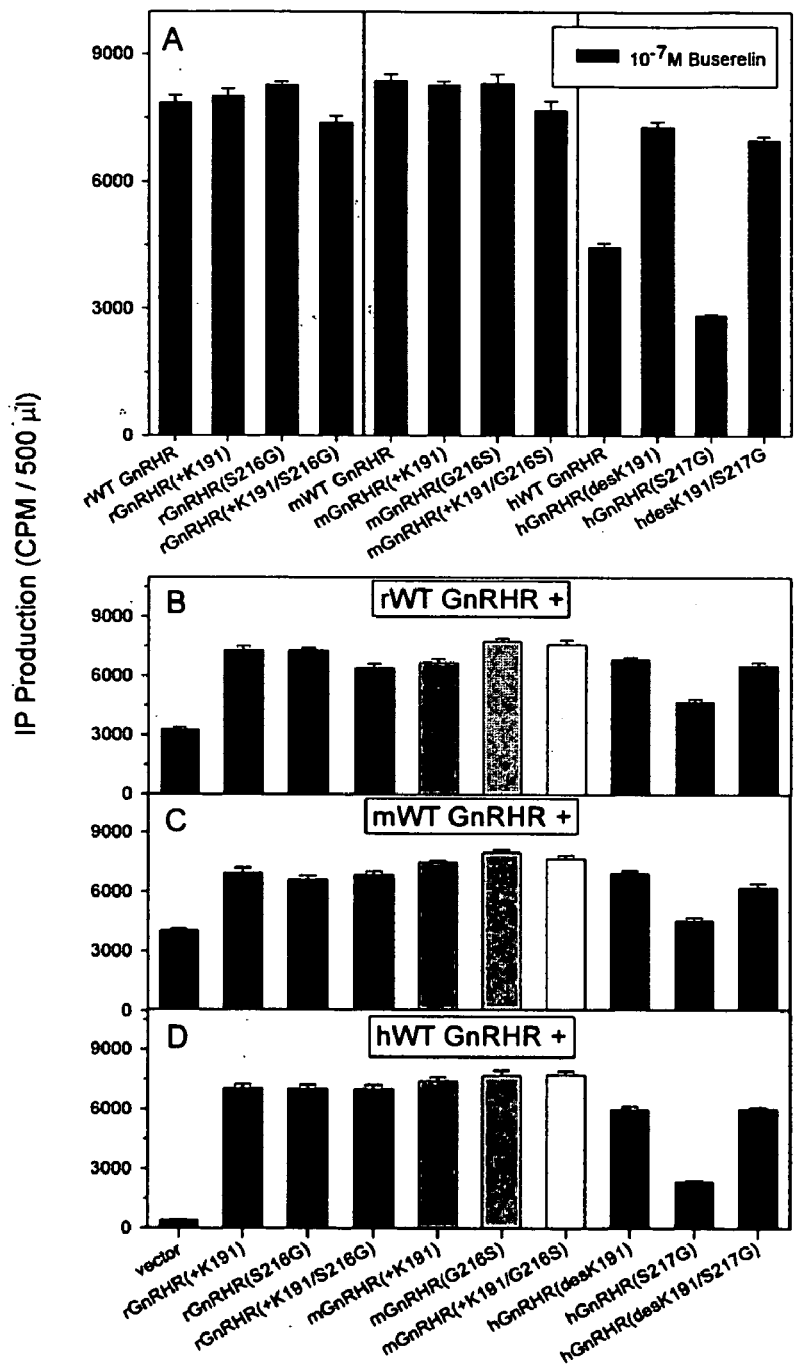
FIGS. 18A-D are bar graphs showing the effect of Lys191 on plasma membrane expression and the dominant negative effect of the rodent 216 and human 217 double mutants. (A) The indicated sequences were expressed in Cos-7 cells to assess the effect of Lys191. Expression data are shown for rat, mouse and human sequences. (B-D) The dominant negative action of these sequences on WT sequence is shown. Data presented as mean CPM±SEM per 500 ul sample. For comparison, 5 ng of rat, mouse or human WT with empty vector is shown on the left of figures B-D. 100 ng of empty vector produced 109.0±2.0 cpm (A) and 98.3±3.3 cpm (B-D).

FIG. 18A shows the effect of inserting the $K^{191}$ residue in rat, human, and mouse WT as well as in $G^{216}S$ (mouse) and $S^{216}G$ (rat, human) mutants. Both mouse and rat WT GnRHR ($+K^{191}$) mutants show no altered IP production as compared to respective WT. However when rat GnRHR contains the $S^{216}G$ mutation, the insertion of $K^{191}$ decreases IP production. In contrast, when the mouse $G^{216}S$ mutant contains the inserted $K^{191}$, IP production decreased. This indicates a relationship between amino acids 191 and 216 of GnRHR. Both human WT GnRHR and human GnRHR($S^{217}G$) show increased IP production when the $K^{191}$ residue is removed. FIGS. 18. B-D show the result of co-transfection of the GnRH mutants in FIG. 18A with the indicated WT GnRHR sequence. No dominant negative action was observed, but rather an additive effect was noticed in all cases. This observation indicates that these mutants do not oligomerize (as seen with the GnRHR($E^{90}K$) mutants) but rather express both WT and mutant GnRH at the plasma membrane.

Figure 19:
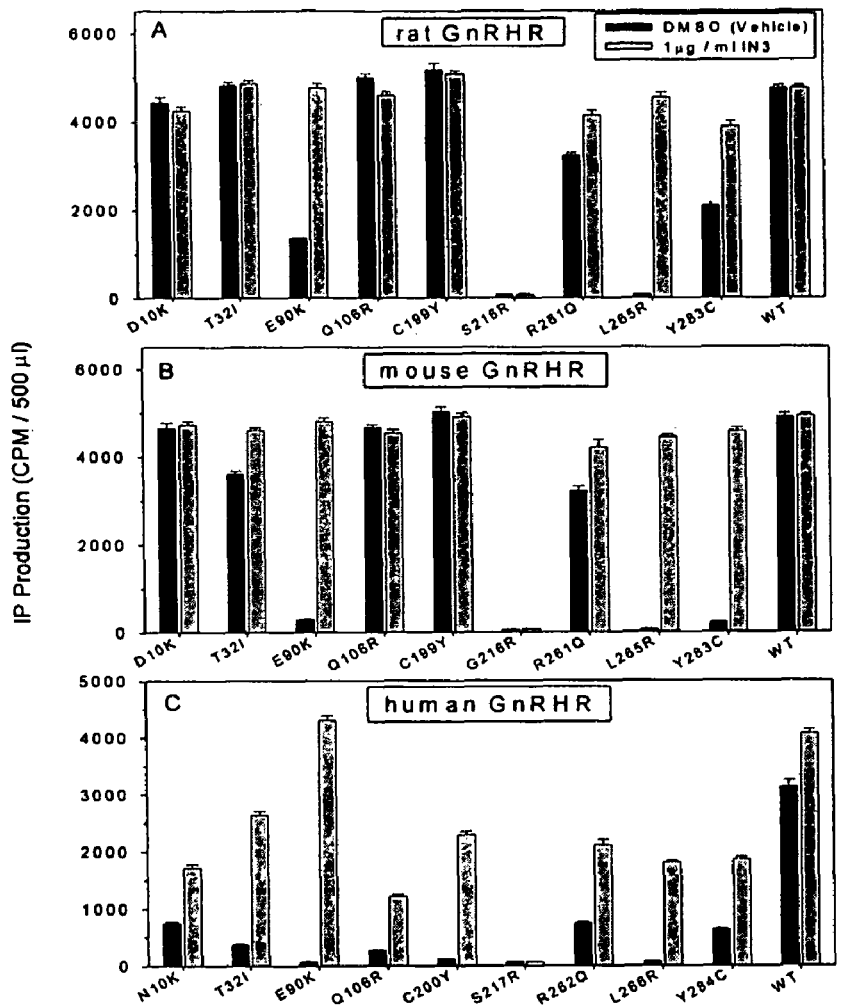
FIGS. 19A-C are bar graphs showing the effect of mutations in the human GnRHR from patients with hypogonadotropic hypogonadism in the mouse and rat receptor sequences. When IN3 was present, it was added at 1 μg/ml (results in optimum rescue). Vector alone produced a response of 79.0±4.9 cpm.

FIGS. 19A and B show the effect of inserting human GnRHR mutations into rodent GnRHR sequences. The human GnRHR point mutations have been observed in patients with HH. For comparison, the human data is shown (FIG. 19C). The pharmacoperone IN3 was used to restore proper folding and thereby rescue the misrouted mutant receptor. In the case of the rat GnRHR, the ability of these mutations to cause misrouting of the rat mutant is lost or greatly diminished (compared to their effects on hGnRHR), except with mutations $S^{216}R$, $L^{265}R$, and $Y^{283}C$. The rodent GnRHRs appear to be less tolerant of mutation than is the human GnRHR. Additionally, insertion of human mutations into the mouse GnRHR reduce plasma membrane expression of the mutant GnRHRs to a greater extent than was observed for the rat. This observation physiologically demonstrates the importance of the small number of semi- and non-conservative differences between the mouse and rat GnRHRs.

Figure 20A:
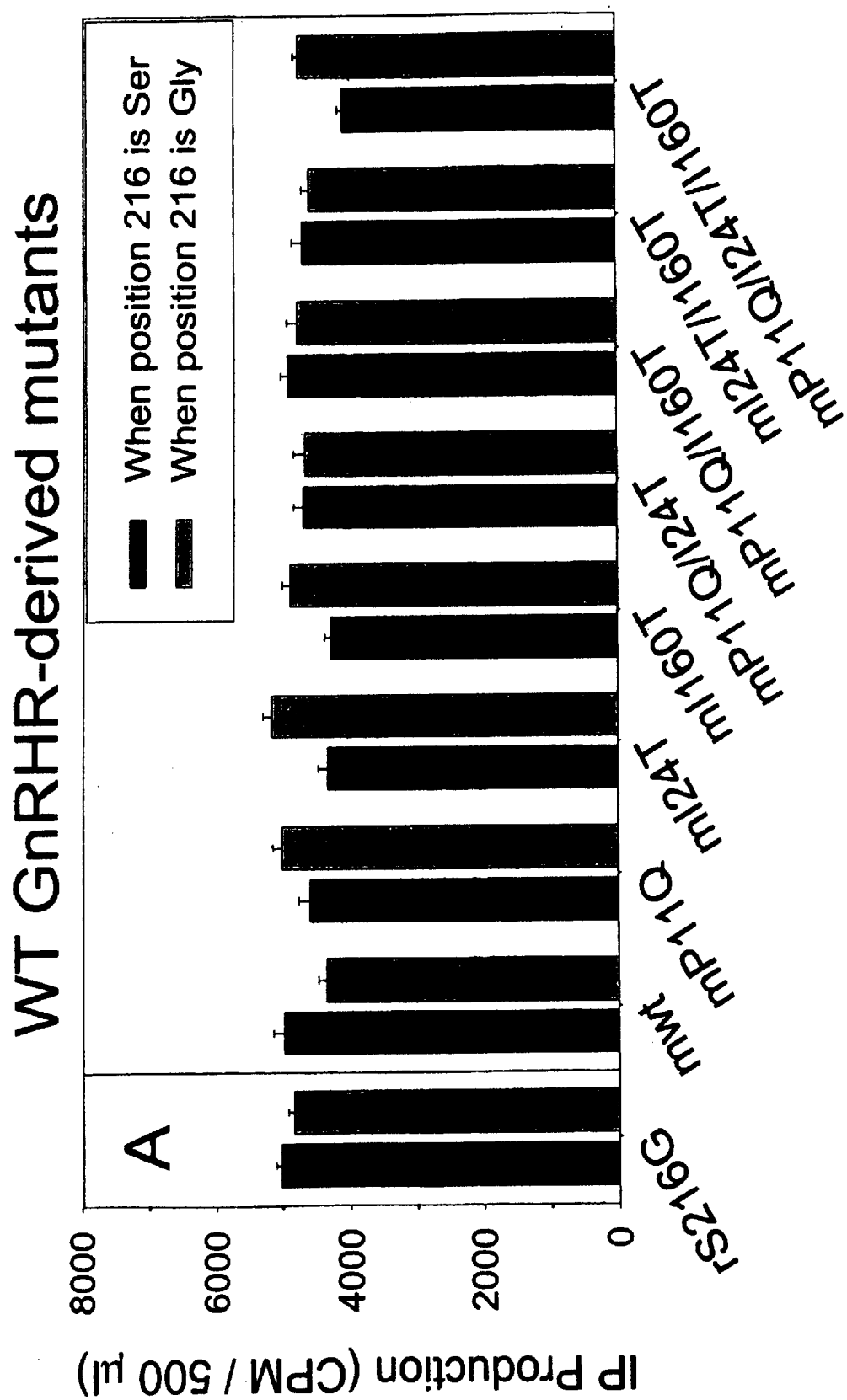
FIGS. 20A-D are bar graphs showing the effect of the four semi- and non-conservative rodent differences on the WT human GnRHR sequence. (A) shows expression of mouse WT GnRHR-derived mutants. (B-D) show co-transfection with indicated WT GnRHR. The dotted lines indicate IP production of WT GnRHR co-transfection with vector. Vector alone produced responses of 71.6±0.9 cpm (A) and 81.4±2.9 (B-D).
Figure 20B:
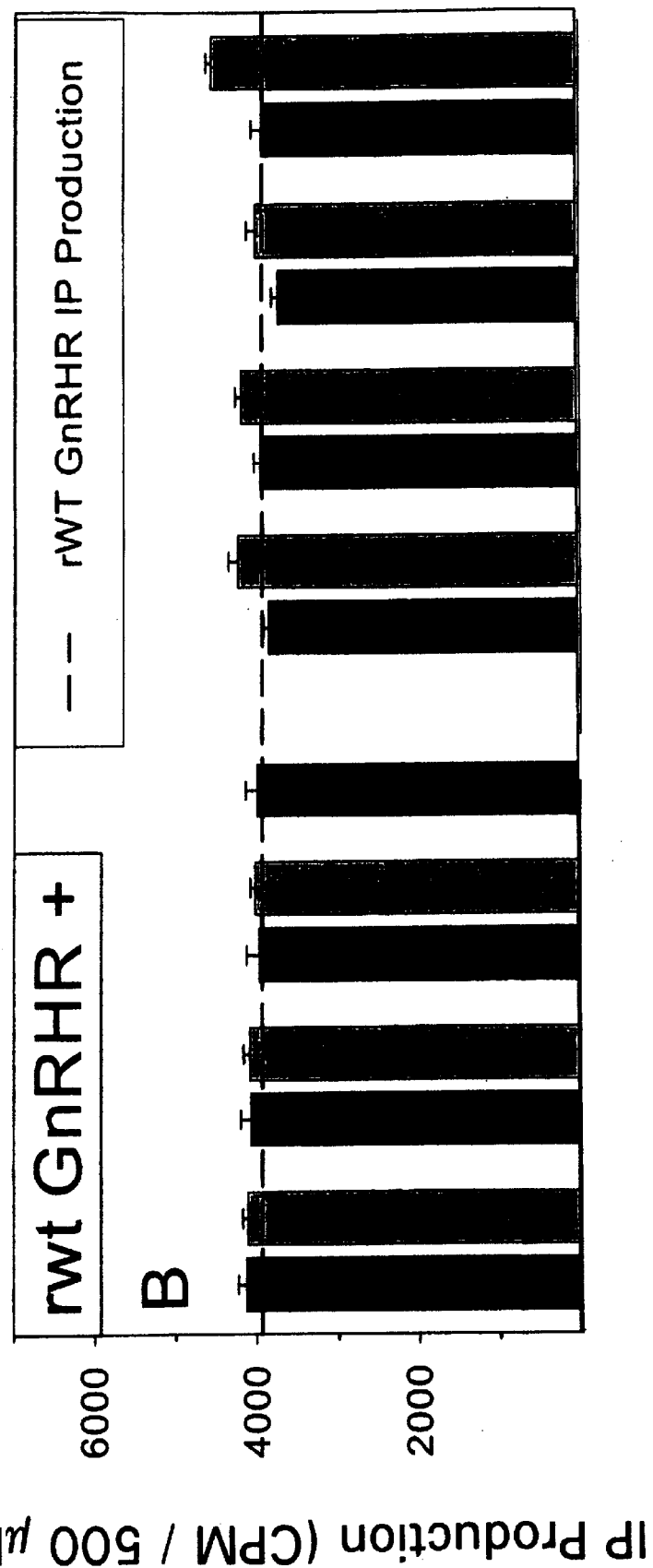
Figure 20C:
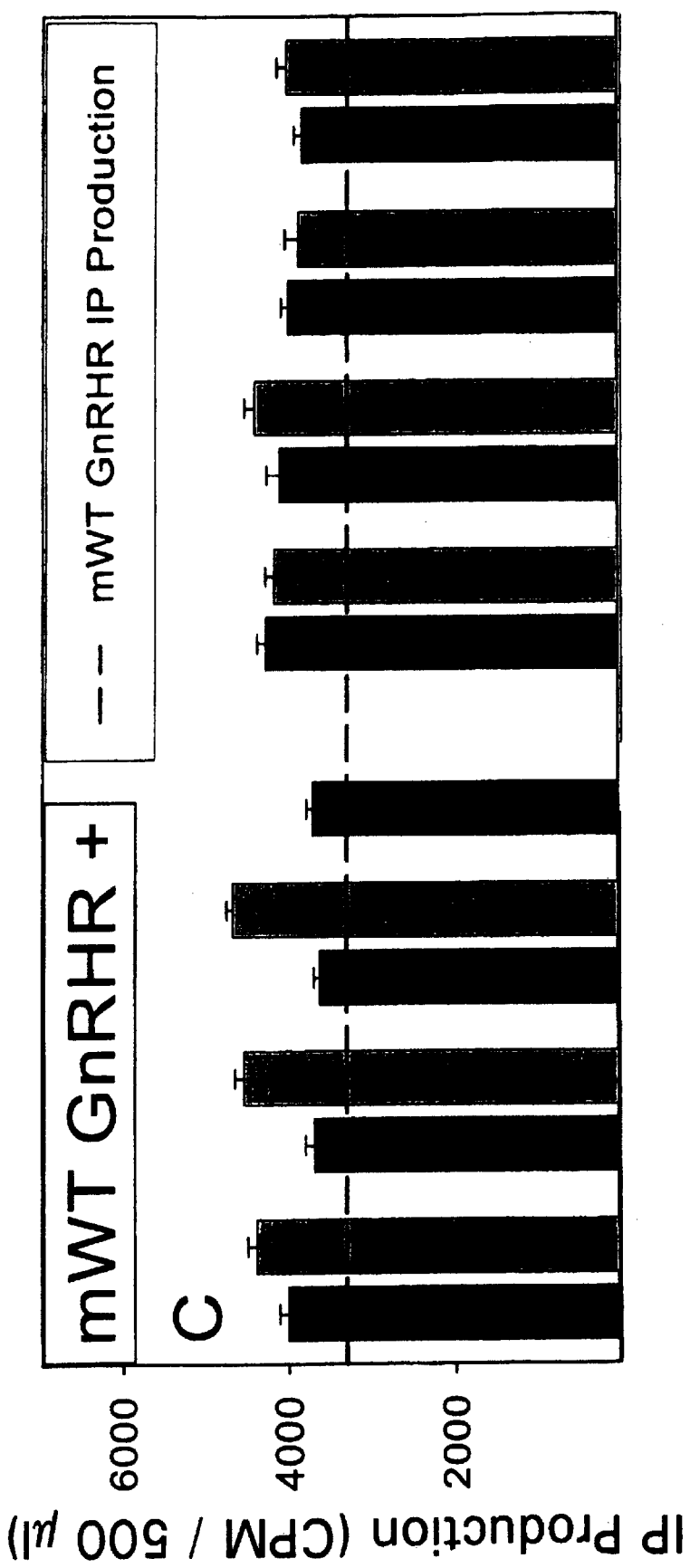
Figure 20D:
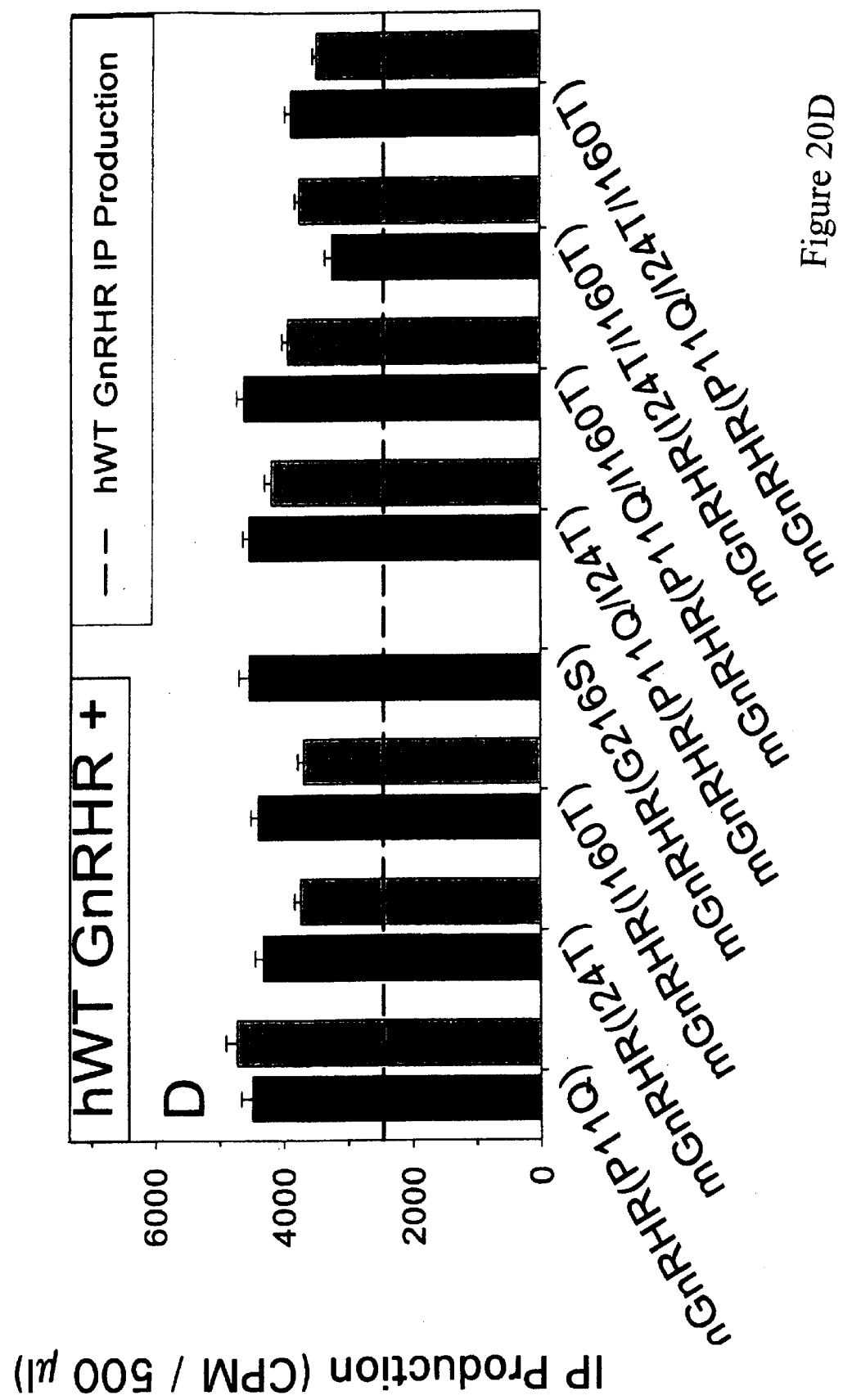

FIG. 20A shows the effect of inserting the four semi- and non-conservative rodent differences in the mouse WT GnRHR into rat GnRHR. The rat GnRHR($S^{216}G$) is shown on the left for comparison. There were only very modest differences between any of the singly or multiply-modified mouse mutants in comparison with mouse WT GnRHR plasma membrane expression levels. This indicates that the difference between the rat and mouse at position 216 has no effect on wild type expression and is only observed when mutations are present that decrease expression at the plasma membrane. No dominant negative effects were observed (FIGS. 20B-D) with the mouse mutants on any of the three species WT GnRHR.

This data demonstrates that a single amino acid, $S^{216}$, in the rat GnRHR sequence increases the efficiency of routing to the plasma membrane of rat mutants that are otherwise retained in the ER. This same amino acid is responsible for loss of the dominant-negative effect of rat mutants when co-expressed with WT receptor. The homologous amino acid in the hGnRHR is also Ser ($S^{217}$), and is compensated for by the primate-unique insertion of $K^{191}$ that, alone, dramatically decreases routing of the receptor.

The dominant-negative effect in primates is restored by insertion of $K^{191}$ (along with $S^{217}$) into the GnRHR sequence, which greatly diminishes expression of the human sequence at the plasma membrane, and greatly increases the susceptibility of disturbing the conformation of this receptor with single charge changes in the primary sequence.

In humans, the rat $S^{216}$ homologous locus is also the site of a naturally occurring mutation in the human receptor that leads to HH ($S^{217}R$). This mutation is one of two known mutations that cannot be rescued by pharmacological chaperones (see Example 1), indicating that either such mutations have a dramatic effect on the conformation of the GnRHR or that this area is important for ligand binding or effector activation.

Based on the observation that particular human GnRHR mutations result in a dominant negative effect, one can predict the severity of disease in a subject having a GnRHR mutation, based on the particular mutation the subject has (see Example 6).

EXAMPLE 6

Prediction of Disease Severity

Based on the results described in Example 5, subjects having or suspected of having HH can be screened to determine which GnRHR mutations are present, to identify those subjects that will have a more severe form of HH. As described in Example 5, particular GnRHR mutations result in a dominant negative effect on GnRHR receptor activity and trafficking. For example, it would normally be expected that a heterozygous subject having a GnRHR mutation would have a less severe phenotype than a homozygous subject having a GnRHR mutation. However, as shown in Example 5, some GnRHR mutations result in a greater decrease in the amount of wild-type GnRHR available for ligand binding at the cell surface than other GnRHR mutations.

Currently, there are eighteen known mutants of GnRHR known to cause isolated HH. Of these, two are missing large sequences: one being a truncation of all amino acids between 314 and the amino terminal amino acid 328, and the other, a deletion mutant missing exon 2. Such large sequence omissions likely have a dramatic effect on the receptor structure. The remaining mutations are subtler, involving only a single amino acid. Of these, three involve loss (two occurrences, such as $Pro^{320}Leu$) or gain (one occurrence) of a cysteine residue, which would likely cause disruption of required bridges or formation of inappropriate bridges and disrupt protein structure. One of these recently reported mutations.

The remaining 12 HH-associated mutants are caused by modest changes in a single charge. Ten of these twelve mutations involve Lys (three occurrences), Arg (six occurrences) or Asp (one occurrence). Introduction of (even minor) charge changes appear sufficient to alter the structure. None of the reported mutations are conservative in which, for example, Ala replaces a Gly or Thr replaces a serine; in each case adding a single carbon without modifying the net charge. Likewise, there are no examples of simple hydrophobic for hydrophobic exchanges (Val for Ala, for example), positive for positive (e.g. Lys for Arg) exchanges or negative for negative (e.g. Asp for Glu) exchanges. Such exchanges may occur, but may be clinically silent or, alternatively, the phenotype may not survive.

In the case of the mutant positions in human GnRHR associated with disease, the amino acid in the corresponding human WT is significantly conserved in mammals. The exceptions are $Asn^{10}Lys$ (for which Asp is found in mouse and rat, but Asn in other mammals sequenced), $Ser^{168}Arg$ (for which I is found in mouse and rat, but Ser is in other mammals sequenced), $Ser^{217}Arg$ (mouse is Gly; guinea pig is Ile), $Cys^{200}Tyr$ (Gly in pig), $Tyr^{284}Cys$ (pig is Leu). The $Arg^{139}His$ is part of the DRS motif (DRY in most mammalian receptors) in intracellular region 2.

This charge sensitivity of the human GnRHR may diminish the efficiency of transfer of this protein to the plasma membrane by insertion of $K^{191}$. As shown in the above Examples, pharmacoperone-rescue indicates that insertion of this charged amino acid decreases the expression of the human WT receptor by about 40%. In contrast, the rodent WT receptors appear to be fully expressed at the plasma membrane.

Generally, the method includes (if not already known) screening subjects having or suspected of having HH, to identify the GnRHR mutation present. Methods of performing such screening are known in the art, and include the specific methods provided in Example 7 below. Those subjects having a GnRHR mutation that has a dominant negative effect (that is, wherein the mutant GnRHR protein decreases ligand binding and ligand activated second messenger production by wild-type GnRHR present) will likely have a greater disease severity, than will a subject having a GnRHR mutation that has no such dominant negative effect. Such information can also be used to select a particular therapy for the subject. For example, a subject having a mutant GnRHR that has a dominant negative effect will likely not respond to treatment that includes administration of wild-type GnRHR (protein or nucleic acid), and instead could be administered a pharmacoperone that can rescue mis-folded GnRHR. In contrast, a subject having a mutant GnRHR that does not have a dominant negative effect could respond to treatment that includes administration of wild-type GnRHR (protein or nucleic acid), or administration of a pharmacoperone that can rescue mis-folded GnRHR.

Subjects having an $E^{90}K, S^{168}R, S^{217}R$, or $L^{266}R$, mutation in a human GnRHR amino acid sequence (or combinations thereof) would be expected to have a greater severity of one or more symptoms associated with HH, than would a subject having a $A^{129}D, R^{139}H, C^{200}Y, C^{279}Y$ AND $W^{205}X$ hGnRHR mutation. Therefore, a subject having a $E^{90}K, S^{168}R, S^{217}R$, or $L^{266}R$ hGnRHR mutation (or combinations thereof), would not be selected for treatment by administration of a GnRHR protein or nucleic acid sequence.

EXAMPLE 7

Identification of Subjects that Could Benefit from Pharmacoperone Therapy

Based on the results described in Example 2, subjects having or suspected of having HH can be screened to determine which GnRHR mutations are present, to identify those subjects that would benefit from treatment with a pharmacoperone. This example describes methods that can be used to identify such subjects.

Generally, the method includes (if not already known) identifying one or more genetic mutations associated with protein misfolding, for example misfolding that affects cellular trafficking of the protein (for example protein transport within the cell or to the plasma membrane). The ability of the genetic mutations to be rescued by a pharmacoperone is then determined (if not already known). Subjects are screened to identify whether they have a mutation in a protein of interest. Those subjects having a mutation shown to be rescued with a pharmacoperone are selected to receive pharmacoperone therapy, while those subjects having a mutation shown to not be rescuable with a pharmacoperone are not administered a pharmacoperone. Depending on the genotype of the subject, partial or full restoration of receptor function in response to pharmacological chaperones can be achieved in subjects bearing inactivating mutations in the gene. Although particular examples are provided for the GnRHR, one skilled in the art will appreciate that similar methods can be used to screen subjects having other mis-folded proteins that are improperly trafficked.

In one example, subjects having a GnRHR mutation that can be rescued with one or more pharmacoperones are selected to receive pharmacoperone therapy, while those subjects having a mutation that is not rescuable with a pharmacoperone are not administered a pharmacoperone. Depending on the genotype of the subject, partial or full restoration of receptor function in response to pharmacological chaperones can be achieved in HH subjects bearing inactivating mutations in the hGnRHR gene.

Samples containing nucleic acid molecules or proteins can be obtained from any appropriate specimen, for instance blood or blood-fractions (such as serum). Techniques for acquisition of such samples are well known in the art (for example see Schluger et al. *J. Exp. Med.* 176:1327-33, 1992, for the collection of serum samples). Serum or other blood fractions can be prepared in the conventional manner. For example, about 200 μL of serum can be used for the extraction of DNA for use in sequencing reactions.

Once a sample has been obtained, the sample can be used directly, concentrated (for example by centrifugation or filtration), purified, or combinations thereof. In one example, DNA is prepared from the sample, yielding a nucleotide preparation that is accessible to, and amenable to, nucleic acid sequencing. Similarly, RNA can be prepared using a commercially available kit (such as the RNeasy Mini Kit, Qiagen, Valencia, Calif.). In yet another example, proteins are prepared from the sample (for example by using a commercially available kit, such as the Compartment Protein Isolation Kit from BioChain Institute, Inc., Hayward, Calif.) yielding a protein preparation that is accessible to, and amenable to, protein sequencing.

Methods for determining the sequence of a nucleic acid molecule or a protein are routine in the art. Exemplary methods of nucleic acid sequencing include, but are not limited to, the Maxam-Gilbert chemical degradation method (Maxam and Gilbert, 1977,*Proc. Natl. Acad. Sci., USA* 74:560), the Sanger dideoxy chain termination method (Sanger et al., 1977, *Proc. Natl. Acad. Sci., USA* 74:5463), and improvements on these methods, such as those described in U.S. Pat. No. 5,124,247 to Ansorge, U.S. Pat. No. 5,242,796 to Prober et al., U.S. Pat. No. 5,306,618 to Prober et al., U.S. Pat. No. 5,360,523 to Middendorf et al., U.S. Pat. No. 5,556,790 to Pettit, U.S. Pat. No. 5,821,058 to Smith et al., U.S. Pat. Nos. 5,221,518 and 5,064,754 to Mills, U.S. Pat. No. 4,863,849 to Melamede, U.S. Pat. No. 5,302,509 to Cheeseman, U.S. Pat. Nos. 4,962,037 and 5,405,747 to Jett et al., U.S. Pat. No. 5,674,743 to Ulmer, and Karger, *Nucl. Acids Res.* 19:4955-62, 1991. Exemplary methods of protein sequencing include, but are not limited to, Edman chemistry and peptide mass spectrometry, and those methods described in U.S. Pat. No. 4,548,904 to Kent et al., U.S. Pat. No. 5,064,767 Le et al.

Subjects having a $N^{10}K, T^{32}I, E^{90}K, Q^{106}R, A^{129}D, R^{139}H, A^{171}T, C^{200}Y, R^{262}Q, L^{266}R, C^{279}Y$, or $Y^{284}C$ mutation in a human GnRHR amino acid sequence (or combinations thereof such as $Q^{106}R/L^{266}R, A^{171}T/Q^{106}R, L^{314}X_{(stop)}/Q^{106}R, T^{32}I/C^{200}Y, R^{262}Q/A^{129}D, R^{262}Q/Q^{106}R, N^{10}Q/Q^{106}R$, and $R^{262}Q/Y^{284}C$) would be expected to respond better to administration of a pharmacoperone than would a subject having a $S^{168}R, S^{217}R, Q^{106}R/S^{217}R, Q^{106}R/S^{217}R/R^{262}Q, L^{314}{}_{(stop)}/R^{262}Q$, or a $L^{314}X_{(stop)}$ truncated hGnRHR. Therefore, a subject having a $N^{10}K, T^{32}I, E^{90}K, Q^{106}R, A^{129}D, R^{139}H, A^{171}T, C^{200}Y, R^{262}Q, L^{266}R, C^{279}Y$, or $Y^{284}C$ GnRHR mutation (or combinations thereof such as $Q^{106}R/L^{266}R, A^{171}T/Q^{106}R, L^{314}X_{(stop)}/Q^{106}R, T^{32}I/C^{200}Y, R^{262}Q/A^{129}D, R^{262}Q/Q^{106}R N^{10}Q/Q^{106}R$, and $R^{262}Q/Y^{284}C$), can be selected for treatment with one or more pharmacoperones, while a subject having a $S^{168}R, S^{217}R, Q^{106}R/S^{217}R, Q^{106}R/S^{217}R, Q^{106}R/S^{217}R/R^{262}Q$, or a $L^{314}X_{(stop)}/R^{262}Q$ mutation, or a $L^{314}X_{(stop)}$ truncated hGnRHR, would not be selected for treatment with a pharmacoperone.

EXAMPLE 8

Treatment of Subjects

This example describes methods that can be used to treat a subject having a disorder resulting from mis-folding of a protein. The method includes screening a subject having or thought to have a mutation in a protein that results in misfolding of the protein and disease, to identify those subjects that can benefit from administration of a pharmacoperone. There are many known diseases that result from misfolded and misrouted proteins which can benefit from the methods disclosed herein.

As described in Example 7, identification of the mutations which are rescuable by a pharmacoperone can be used to identify those subjects that will benefit from administration of a pharmacoperone. If a determination has not been made as to which mutations that result in protein mis-folding and improper cellular trafficking are rescuable by one or more pharmacoperones, the method includes this step. Mutations for a particular protein can then be categorized as rescuable or non-rescuable by a pharmacoperone. Subjects are then screened to determine which mutation is present, for example using the methods described in Example 7. Subjects having one or more mutations that can be rescued with a pharmacoperone are selected to receive pharmacoperone therapy, while those subjects having a mutation not rescuable with a pharmacoperone are not administered a pharmacoperone. Those subjects selected to receive pharmacoperone therapy are administered a pharmacoperone.

Restoration of function to the mutant protein need not result in 100% restoration of protein function, nor treatment of 100% of the symptoms associated with the disease. Depending on the genotype of the subject, partial or full restoration of receptor function in response to pharmacological chaperones can be achieved in subjects bearing inactivating mutations in the gene.

In some examples, following administration of a therapeutic amount of a pharmacoperone, the pharmacoperone is removed. For example, if the pharmacoperone is an antagonist of the protein (such as an antagonist of the mutant receptor), the pharmacoperone can be removed to permit the rescued protein to have its biological activity. For example, if the protein is a receptor, removal of the antagonist may permit binding of the receptor to its ligand, thereby permitting the receptor to exert is biological activity on the cell. In some examples, removal of the pharmacoperone includes a period of time where the pharmacoperone is not administered to the subject. For example, the subject can be administered a therapeutic amount of a pharmacoperone, followed by a period of non-administration, which can then be followed by another administration of the pharmacoperone, administration of a therapeutically effective amount of other agent that increases biological activity of the rescued protein (such as an agonist of the mutant rescued protein), or combinations thereof in any order needed to treat the subject. This type of administration can be used, for example, when the pharmacoperone dissociates from the rescued protein after a period of time. In other examples where the pharmacoperone (in the absence of other agents) does not effectively dissociate from the rescued protein, an agent that increases dissociation of the pharmacoperone from the rescued protein (such as an increase of at least 10% as compared to an amount of dissociation in the absence of the agent) can be administered at a therapeutic amount to the subject. For example, the subject can be administered a therapeutic amount of a pharmacoperone, followed by administration of an agent that increases dissociation of the pharmacoperone from the rescued protein, which can then be followed by another administration of the pharmacoperone, followed by another administration of the pharmacoperone, administration of a therapeutically effective amount of other agent that increases biological activity of the rescued protein (such as an agonist of the mutant rescued protein), or combinations thereof in any order needed to treat the subject.

The mode of administration can be any used in the art, such as those described in Example 13. The amount of pharmacoperone, agonist, or other agent administered to the subject can be determined by a clinician, and may depend on the particular subject treated. Specific exemplary amounts are provided herein.

EXAMPLE 9

Screening Assays

This example describes methods that can be used to screen agents for their ability to restore functionality to a mutant protein, such as a mutant receptor that is not properly trafficked in the cell or to the plasma membrane. Agents identified via the disclosed assays can be useful, for example, in restoring function to mutant mis-folded proteins, for example in treating a subject having a disease that results from the mis-folding. Although particular examples are provided for screening for pharmacoperones that can specifically bind to a mutant GnRHR, one skilled in the art will recognize that similar methods can be used to screen for pharmacoperones that bind with high specificity to other mutant mis-folded proteins.

As disclosed in the Example 1, agents from several different chemical families, including indoles, quinolones, and macrolides, were able to restore function to many GnRHR mutants, such as amino acid substitutions or deletions that lead to the development of HH in a subject. Therefore, screening assays can be used to identify and analyze other agents, such as other GnRHR antagonists, for example other derivatives of indoles, quinolones, and macrolides, that can also restore function to mutant GnRHR. However, the present disclosure is not limited to the particular methods disclosed herein, nor are the screening assays limited to the use of indoles, quinolones, and macrolides, which are provided as specific examples of classes of compounds that could be screened. Similar screening assays can be used to identify and analyze test agents to identify pharmacoperones that can restore function to other mutant proteins.

In particular examples, agents identified via the disclosed assays can be useful in restoring function to mutant GnRHR molecules, for example in treating a subject having HH. In addition, agents identified via the disclosed assays can be useful, for example, in increasing cell-surface expression of wild-type GnRHR, for example in treating a subject having hypogonadism. Assays for testing the effectiveness of the identified agents, are discussed below.

Exemplary agents that can be screened include, but are not limited to, any peptide or non-peptide composition in a purified or non-purified form, such as peptides made of D-and/or L-configuration amino acids (in, for example, the form of random peptide libraries; see Lam et al., *Nature* 354:82-4, 1991), phosphopeptides (such as in the form of random or partially degenerate, directed phosphopeptide libraries; see, for example, Songyang et al., *Cell* 72:767-78, 1993), antibodies, and small or large organic or inorganic molecules. A test agent can also include a complex mixture or "cocktail" of molecules. Particular test agents include indole, quinolone, and macrolide derivatives and mimetics.

The basic principle of the assay systems used to identify agents that restore function to a mutant protein, increase expression of wild-type receptor to the cell surface, or both, involves preparing a reaction mixture containing the wild-type or mutant protein and the agent under conditions and for a time sufficient to allow the mutant protein and agent to interact and bind and restore function to the mutant protein (or increase expression of the wild-type protein on the cell surface, or both). Controls are incubated without the test agent or with a placebo. Exemplary controls include agents known not to bind to or restore function to mutant protein. In particular examples, controls for GnRHR can include A-7662.0, Q08, and IN31b. The ability of the agent to restore function to the mutant protein (or increase expression of the wild-type protein on the cell surface, or both) is then determined.

The ability of the agent to increase binding of an agonist to a mutant protein, increase production of an intracellular marker indicative of biological function of the protein, increase surface-bound mutant receptor-ligand complex internalized, or combinations thereof, by at least a desired amount, such as an increase of at least 10%, at least 20%, at least 50%, at least 100%, or even at least 200% in the presence of the agent as compared to an amount of activity in the absence of the agent, indicates that the agent can be used to restore function to the mutant protein, and is therefore an agent that can be used to treat subjects having a disease or disorder associated with the mutant protein. For example, agents that increase binding of a GnRHR agonist to a mutant GnRHR, increase GnRH agonist-stimulated IP production by a mutant GnRHR, increase surface-bound mutant GnRHR-ligand complex internalized, or combinations thereof are agents that can be used to treat subjects having HH.

In addition, the ability of the agent to increase expression of the wild-type protein on the cell surface by at least a desired amount, such as an increase of at least 10%, at least 20%, or even at least 50% in the presence of the agent as compared to an amount of cell-surface expression in the absence of the agent, indicates that the agent can be used to treat a subject having a disorder resulting from decreased expression of the protein on the cell surface. For example, if the agent can increase expression of a wild-type GnRHR on the cell surface by at least 10%, this indicates that the agent can be used to treat hypogonadism, such as secondary hypogonadism.

Methods that can be used to assess these activities are described herein, for example, see Examples 1 and 2. In particular examples cells expressing a GnRHR protein (wild-type or mutant) are contacted with the agent. The amount of agent administered can be determined by skilled practitioners. In some examples, several different doses of the potential therapeutic agent can be administered, to identify optimal dose ranges. Following incubation with the agent, assays are conducted to determine the amount of binding of a GnRHR agonist to a mutant GnRHR, the amount of GnRH agonist-stimulated IP production by a mutant GnRHR, the amount of surface-bound mutant GnRHR-ligand complex internalized, the amount of wild-type GnRHR on the cell surface, or combinations thereof, using the methods described in Examples 1 and 2. Similar methods can be used for any misfolded protein of interest, using an appropriate agonist and an appropriate pharmacoperone.

The ability of an agent, such as those identified using the methods provided above, to restore function to a mutant protein, to increase cell-surface expression of wild-type protein, or both, can be assessed in animal models. For example, an animal model of hypogonadism, such as HH, can be made using standard methods known in the art (for example, see U.S. Pat. Nos. 6,037,521; 6,323,390; and 6,576,811, all herein incorporated by reference). Briefly, a gene-targeting vector is generated using standard molecular biology methods. The targeting vector is transfected into ES cells, for example by electroporation. Surviving clones are selected, and analyzed by Southern blot to identify homologous recombinants. Homologous recombinants are expanded, re-verified by Southern blot, and used to generate mouse chimeras by blastocyst injection. The resulting chimeras are crossed, and the resulting progeny tested to identify those that are heterozygous for the mutation. Heterozygotes are crossed to generate homozygous mutants.

The resulting homozygous mutant animal models can also be used to screen agents for an ability to ameliorate symptoms associated with the disease that results from the mis-folding, such as hypogonadism. In addition, such animal models can be used to determine the $LD_{50}$ and the $ED_{50}$ in animal subjects, and such data can be used to determine the in vivo efficacy of potential agents. Animals of any species, including, but not limited to, mice, rats, rabbits, guinea pigs, pigs, micro-pigs, goats, and non-human primates, such as baboons, monkeys, and chimpanzees, can be used to generate an animal model of the desired disease associated with protein mis-folding if needed.

The appropriate animal is administered one or more agents identified in the examples above, alone or in combination with other therapeutic agents. The amount of agent administered can be determined by skilled practitioners. In some examples, several different doses of the potential therapeutic agent can be administered to different test subjects, to identify optimal dose ranges. Subsequent to the treatment, animals are observed for the symptoms associated with the disease that results from the mis-folding, such as hypogonadism. A decrease in the symptoms associated with the disease that results from the mis-folding, such as hypogonadism, in the presence of the agent provides evidence that the agent is a therapeutic agent that can be used to restore function to a mutant misfolded protein (such as mutant GnRHR) or increase expression of wild-type protein (such as GnRHR), or both.

EXAMPLE 10

Treatment of Hypogonadism

This example describes methods that can be used to increase expression of a wild-type hGnRHR on the cell surface, for example to treat, or reduce the symptoms of hypogonadism, such as erectile dysfunction, infertility, decreased sex drive, decrease in beard and growth of body hair, decrease in size or firmness of the testicles, decrease in muscle mass and increase in body fat, enlarged male breast tissue, hot flashes, mood swings, irritability, depression, fatigue, osteoporosis, delayed puberty, or combinations thereof.

As described in Example 1, several indoles, quinolones and macrolides increased expression of wild-type GnRHR on the surface of the cell. Therefore, use of those agents, as well as other indoles, quinolones, macrolides, or other compound, such as agents identified using the methods described in the examples above, can be administered to a subject at a therapeutically effective dose, thereby relieving the symptoms associated with hypogonadism (for example as sometimes found in older men and women). Such agents can also be administered with other therapeutic agents, such as testosterone and estrogen. By increasing trafficking of wild-type GnRHR to the surface, more receptors are available for ligand binding.

If the agent administered is a GnRHR antagonist, in some examples the antagonist is removed from the GnRHR at the cell surface, to facilitate binding of the receptor to its ligand, GnRH. Methods for removing GnRHR at the cell surface include using an antagonist that reversibly binds to the receptor, and allowing the antagonist to fall off of the receptor over time. For example, following administration of a therapeutic amount of a GnRHR antagonist, the pharmacoperone (antagonist) is removed. In some examples, removal of the antagonist includes a period of time where the antagonist is not administered to the subject. For example, the subject can be administered a therapeutic amount of an antagonist, followed by a period of non-administration, which can then be followed by another administration of the antagonist or by administration of a therapeutic amount of an angonist, such as a ligand of the receptor. This type of administration can be used, for example, when the antagonist dissociates from the rescued protein after a period of time. In other examples where the antagonist (in the absence of other agents) does not effectively dissociate from the rescued protein, an agent that increases dissociation of the antagonist from the rescued protein (such as an increase of at least 10% as compared to an amount of dissociation in the absence of the agent) can be administered at a therapeutic amount to the subject. For example, the subject can be administered a therapeutic amount of an antagonist, followed by administration of an agent that increases dissociation of the antagonist from the rescued protein. This can then be followed by another administration of the antagonist, or followed by administration of a therapeutic amount of the agonist.

The mode of administration can be any used in the art, such as those described in Example 13. The amount of pharmacoperone, agonist, or other agent administered to the subject can be determined by a clinician, and may depend on the particular subject treated. Specific exemplary amounts are provided herein.

EXAMPLE 11

Treatment of Hypogonadotropic Hypogonadism (HH)

This example describes methods than can be used to treat or reduce the symptoms of a disorder associated with expression of mutant GnRHR, such as hypogonadotropic hypogonadism.

As described in Example 1, several indoles, quinolones and macrolides increased IP production and agonist binding at the cell surface. Therefore, use of those agents, as well as agents identified using the methods described herein, can be administered to a subject at a therapeutically effective dose, thereby reliving the symptoms associated with HH due to a mutant GnRHR. Such agents can also be administered with other therapeutic agents, such as testosterone and hCG. By restoring at least partial function to mutant GnRHR, GnRHR is are available at the cell surface for ligand binding.

If the agent administered is a GnRHR antagonist, in some examples the antagonist is removed from the GnRHR at the cell surface as described in the examples above.

The mode of administration can be any used in the art, such as those described in Example 13. The amount of pharmacoperone, agonist, or other agent administered to the subject can be determined by a clinician, and may depend on the particular subject treated. Specific exemplary amounts are provided herein.

EXAMPLE 12

Calculation of IC50

This example describes a method that can be used to determine the inhibitory concentration ($IC_{50}$) of an agent, such as a GnRHR antagonist. However, one skilled in the art will appreciate that other methods can be used.

Agents can be tested over a range of concentrations (for example, $10^{-1}$ to $10^{-8}$ μM). For example, serial 10-fold dilutions of each agent are prepared in a vehicle (such as DMSO) and stored on ice. Cells, such as COS-7 cells, are transfected with wild-type or mutant hGnRHR as described in Example 1. Cells are transfected with about 0.01 μg-0.05 mg DNA for inositol phosphate production, or 0.1 mg DNA for saturation binding studies. Cells expressing wild-type GnRHR are incubated in the presence of the agent, such as 1 μg/ml, and in the presence of various concentrations of $^{125}$I-buserelin ($10^{-13}$ M-$10^{-7}$M), and IP production or saturation binding measured as described in Example 1. The most accurate method for determining $IC_{50}$ values is to use non-linear regression analysis, as described in Example 1.

EXAMPLE 13

Pharmaceutical Compositions and Modes of Administration

This example provides methods and pharmaceutical compositions that can be used to administer a pharmacological chaperone (pharmacoperone) (alone or in combination with other therapeutic agents) that can restore function to mutant mis-folded protein, to increase expression of wild-type proteins at the cell surface, or both. In particular examples, the pharmacoperone is an agonist or an antagonist of the protein. Administration of such compositions to a subject can begin whenever treatment of symptoms associated with a disease associated with a mis-folded protein, for example decreased binding of GnRH to its receptor GnRHR, for example due to expression of a mutant GnRHR, is desired. While compositions that include a pharmacoperone may typically be used to treat human subjects, they can also be used to treat similar or identical diseases in other vertebrates such as other primates, farm animals such as swine, cattle and poultry, and sport animals and pets such as horses, dogs and cats.

The pharmaceutical compositions that include a pharmacoperone can be formulated in unit dosage form, suitable for individual administration of precise dosages. A therapeutically effective amount of a pharmacoperone can be administered in a single dose, or in multiple doses, for example daily, during a course of treatment. Compositions that include a pharmacoperone can be administered whenever the effect (such as decreased symptoms of HH) is desired. A time-release formulation can also be utilized.

A therapeutically effective amount of a composition that includes a pharmacoperone can be administered as a single pulse dose, as a bolus dose, or as pulse doses administered over time. In pulse doses, a bolus administration of a composition that includes a pharmacoperone is provided, followed by a time-period wherein no pharmacoperone is administered to the subject, followed by a second bolus administration. In some examples, the time-period wherein no pharmacoperone is administered is at least 24 hours, at least 48 hours, at least 72 hours, at least 96 hours, at least one week, at least two weeks, at least one month, or at least 6 months. In specific, non-limiting examples, pulse doses of compositions that include a pharmacoperone are administered during the course of a day, during the course of a week, or during the course of a month.

The therapeutically effective amount of a composition including a pharmacoperone can depend on the molecule utilized, the subject being treated, the severity and type of the affliction, and the manner of administration, and should be decided according to the judgment of the practitioner and each subject's circumstances. Therapeutically effective amounts of compositions that include a pharmacoperone are those that restore function to a mutant protein by an amount that decreases one or more symptoms of the disease, an amount that increases expression of a wild-type protein on the cell surface (for example an increase of at least 20%), or both. In vitro assays can be employed to identify optimal dosage ranges. Effective doses can be extrapolated from dose-response curves derived from in vitro or animal model test systems. For example, a therapeutically effective amount of a pharmacoperone can vary from about 0.001 μg per kilogram (kg) body weight to about 20 mg per kg body weight, such as about 1 μg to about 5 mg per kg body weight, such as about 2 μg to about 0.5 mg per kg body weight, or about 5 μg to about 1 mg per kg body weight. The exact dose is readily determined by one of skill in the art based on the potency of the specific compound utilized, the age, weight, sex and physiological condition of the subject.

The compositions or pharmaceutical compositions can be administered by any route, including intravenous, intraperitoneal, subcutaneous, sublingual, transdermal, intramuscular, oral, topical, transmucosal, vaginal, nasal, rectal, by pulmonary inhalation, or combinations thereof. Compositions useful in the disclosure may conveniently be provided in the form of formulations suitable for parenteral (including intravenous, intramuscular and subcutaneous), nasal, topical, or oral administration. The term "parenteral" refers to non-oral modes of administration that include intravenous, intramuscular, intraperitoneal, intrasternal, subcutaneous and intraarticular injection and infusion.

In some examples, compositions that include a pharmacoperone are administered in combination with (such as before, during, or following) a therapeutically effective amount of one or more other therapeutic agents, in a single composition or solution for administration together. In other cases, it may be more advantageous to administer the additional agent separately from the pharmacoperone. Compositions that include a pharmacoperone can be administered simultaneously with the additional agent(s), or administered sequentially. In one example, the other therapeutic agent is a steroid (for example estrogens and androgens) or other agents that alleviate symptoms associated with hypogonadism. In one example, a composition that includes a pharmacoperone is formulated and administered with estrogen or androgen as a single dose.

Therapeutic compositions can be provided as parenteral compositions, such as for injection or infusion. Such compositions are formulated generally by mixing a pharmacoperone at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a pharmacoperone can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

A form of repository or "depot" slow release preparation can be used so that therapeutically effective amounts of the preparation are delivered into the bloodstream over many hours or days following transdermal injection or delivery. Such long acting formulations can be administered by implantation (for example subcutaneously or intramuscularly) or by intramuscular injection. The compounds can be formulated with suitable polymeric or hydrophobic materials (for example as an emulsion in an acceptable oil) or ion exchange resins, or as sparingly soluble derivatives, for example, as a sparingly soluble salt.

Pharmacoperones can be utilized as free bases, as acid addition salts or as metal salts. The salts ideally are pharmaceutically acceptable, and include metal salts, for example alkali and alkaline earth metal salts, such as potassium or sodium salts. Numerous pharmaceutically acceptable acid addition salts are available. Such products are readily prepared by procedures well known to those skilled in the art.

Pharmaceutical compositions that include a pharmacoperone as an active ingredient can be formulated with an appropriate solid or liquid carrier, depending upon the particular mode of administration chosen. The product can be shaped into the desired formulation. In one example, the carrier is a parenteral carrier, such as a solution that is isotonic with the blood of the recipient. Examples of such carrier vehicles include water, saline, Ringer's solution, glycerol and dextrose solution. Non-aqueous vehicles such as fixed oils and ethyl oleate are also useful herein, as well as liposomes. Other carriers include, but are not limited to: fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate. Additional pharmaceutically acceptable carriers and their formulation are described in standard formulation treatises, such as *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

If desired, the disclosed pharmaceutical compositions can also contain minor amounts of non-toxic auxiliary substances, such as wetting or emulsifying agents, preservatives, and pH buffering agents and the like, for example sodium acetate or sorbitan monolaurate. Excipients that can be included in the disclosed compositions include flow conditioners and lubricants, for example silicic acid, talc, stearic acid or salts thereof, such as magnesium or calcium stearate, and/or polyethylene glycol, or derivatives thereof.

Compositions including a pharmacoperone can be administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral, otic, or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Sustained-release compositions include liposomes containing a pharmacoperone (see generally, Langer, Science 249:1527-1533, 1990; Treat et al., in *Liposomes in the Therapy of Infectious Disease and Cancer*, Lopez-Berestein and Fidler (eds.), Liss, New York, pp. 317-327 and 353-65, 1989). Liposomes containing a pharmacoperone thereof can be prepared by known methods: DE 3,218,121; Epstein et al., *Proc. Natl. Acad. Sci. U.S.A.* 82:3688-92, 1985; Hwang et al., *Proc. Natl. Acad. Sci. U.S.A.* 77:4030-4034, 1980; EP 52,322; EP 36,676; EP 88,046; EP 143,949; EP 142,641; Japanese Patent Application No. 83-118008; U.S. Pat. No. 4,485,045, U.S. Pat. No. 4,544,545; and EP 102,324.

Preparations for administration can be suitably formulated to give controlled release of a pharmacoperone. For example, the pharmaceutical compositions can be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See U.S. Pat. No. 5,700,486.

Compositions that include a pharmacoperone can be delivered by way of a pump (see Langer, supra; Sefton, *CRC Crit. Ref Biomed Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (Science 249: 1527-33, 1990).

In one example, the pump is implanted (for example see U.S. Pat. Nos. 6,436,091; 5,939,380; and 5,993,414). Implantable drug infusion devices are used to provide patients with a constant and long-term dosage or infusion of a drug or any other therapeutic agent. Such device can be categorized as either active or passive.

Active drug or programmable infusion devices feature a pump or a metering system to deliver the agent into the patient's system. An example of such an active infusion device currently available is the Medtronic SynchroMed™ programmable pump. Passive infusion devices, in contrast, do not feature a pump, but rather rely upon a pressurized drug reservoir to deliver the agent of interest. An example of such a device includes the Medtronic IsoMed™.

For oral administration, the pharmaceutical compositions can take the form of, for example, powders, pills, tablets, or capsules, prepared by conventional means with pharmaceutically acceptable excipients such as binding agents (such as pregelatinized maize starch, polyvinylpyrrolidone or hydroxypropyl methylcellulose); fillers (such as lactose, microcrystalline cellulose or calcium hydrogen phosphate); lubricants (such as magnesium stearate, talc or silica); disintegrants (such as potato starch or sodium starch glycolate); or wetting agents (such as sodium lauryl sulphate). The tablets can be coated by methods well known in the art.

For administration by inhalation, the compounds for use according to the present disclosure can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of for example gelatin for use in an inhaler or insufflator can be formulated containing a powder mix of the compound and a suitable powder base such as lactose or starch.

For inhalation, the composition of the present disclosure can also be administered as an aerosol or as a dispersion in a carrier. In one specific, non-limiting example, a pharmacoperone (alone or in combination with other therapeutic agents or pharmaceutically acceptable carriers), is administered as an aerosol from a conventional valve, such as, but not limited to, a metered dose valve, through an aerosol adapter also known as an actuator. A suitable fluid carrier can be also included in the formulation, such as, but not limited to, air, a hydrocarbon, such as n-butane, propane, isopentane, amongst others, or a propellant, such as, but not limited to a fluorocarbon. Optionally, a stabilizer is also included, or porous particles for deep lung delivery are included (for example, see U.S. Pat. No. 6,447,743).

In the disclosed methods of treating disorders that result from expression of mis-folded mutant protein or from decreased expression of a wild-type protein at the cell surface, the method includes administering to a subject (such as a subject having hypogonadism) a therapeutically effective amount of a pharmacoperone identified using the methods disclosed herein. Pharmacoperones can be administered in a single or divided dose. Suitable single or divided doses include, but are not limited to about 0.01, 0.1, 0.5, 1, 3, 5, 10, 15, 30, or 50 µg pharmacoperone/kg of subject/day.

The disclosure also provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The disclosure provides compositions that include pharmacoperones, for example a composition that includes at least 50%, for example at least 90%, of a pharmacoperone in the composition. Such compositions are useful as therapeutic agents when constituted as pharmaceutical compositions with the appropriate carriers or diluents.

In view of the many possible embodiments to which the principles of this disclosure may be applied, it should be recognized that the illustrated embodiments are only particular examples of the disclosure and should not be taken as a limitation on the scope of the disclosure. Rather, the scope of the disclosure is in accord with the following claims. I therefore claim all that comes within the scope and spirit of these claims.

I claim:

1. An in vitro assay for identifying a pharmacoperone agent that restores function to a mutant gonadotropin-releasing hormone receptor (GnRHR) protein, comprising:
exposing a cell expressing the mutant GnRHR protein to a test agent capable of penetrating a cell membrane; and
measuring inositol phosphate (IP) production by the cell, wherein an increase in IP production by the cell expressing the mutant GnRHR protein compared to production of IP by a cell expressing the mutant GnRHR protein not exposed to the test agent indicates that the test agent is a pharmacoperone agent that restores function to the mutant GnRHR, or measuring GnRHR ligand binding and internalization by the cell expressing the mutant GnRHR protein, wherein an increase in GnRHR ligand binding and internalization by the cell expressing the mutant GnRHR protein as compared to GnRHR ligand binding and internalization by the cell expressing the mutant GnRHR protein not exposed to the test agent indicates that the test agent is a pharmacoperone agent that restores function to the mutant GnRHR, wherein the mutant GnRHR protein, prior to exposure to the test agent, does not increase IP production nor increase GnRHR ligand binding and internalization.

2. The assay of claim 1, wherein the mutation affects GnRHR protein folding.

3. The assay of claim 1, wherein the mutation affects aggregation of the GnRHR protein.

4. The assay of claim 2, wherein the test agent is a non-antagonist of the GnRHR.

5. The assay of claim 2, wherein the test agent binds outside a ligand binding site of the GnRHR.

6. The assay of claim 1, wherein the test agent acts as an agonist of the GnRHR protein.

7. The assay of claim 1, wherein the test agent binds to the GnRHR protein with a dissociation constant (Kd) of less than 1 μM.

8. The assay of claim 1, wherein the test agent is a peptidomimetic of a molecule that binds to the GnRHR protein.

9. The assay of claim 2, wherein the mutation also affects routing of the receptor to the cell membrane surface.

10. The assay of claim 2, wherein the test agent does not interfere with GnRHR ligand binding to the GnRHR receptor.

11. The assay of claim 1, wherein the mutation results in hypogonadotropic hypogonadism (HH).

12. The assay of claim 1, wherein the mutation is an $N^{10}K$ mutation, a $T^{32}I$ mutation, an $E^{90}K$ mutation, a $Q^{106}R$ mutation, an $A^{129}D$ mutation, an $R^{139}H$ mutation, an $A^{171}T$ mutation, a $C^{200}Y$ mutation, an $R^{262}Q$ mutation, an $L^{266}R$ mutation, a $C^{279}Y$ mutation, a $Y^{284}C$ mutation, or combinations thereof, wherein the numbering refers to the amino acid sequence shown in SEQ ID NO: 1.

13. The assay of claim 12, wherein the combination thereof is a $Q^{106}R/L^{266}R$ mutation, $A^{171}T/Q^{106}R$ mutation, $L^{314}X_{(stop)}/Q^{106}R$ mutation, $T^{32}I/C^{200}Y$ mutation, $R^{262}Q/A^{129}D$ mutation, $R^{262}Q/Q^{106}R$ mutation, $N^{10}Q/Q^{106}R$, or $R^{262}Q/Y^{284}C$ mutation, wherein the numbering refers to the amino acid sequence shown in SEQ ID NO: 1.

14. The assay of claim 12, wherein the mutant human GnRHR comprises an E90K mutation, wherein the numbering refers to the amino acid sequence shown in SEQ ID NO: 1.

15. The assay of claim 1, wherein the test agent is an indole, macrolide or quinolone.

16. The assay of claim 10, further comprising determining if the test agent competes with a GnRHR ligand, wherein the presence of competition for a GnRHR ligand binding site indicates that the test agent binds to the GnRHR ligand binding site, and wherein the absence of detectable competition for the GnRHR ligand binding site indicates that the test agent does not bind to the GnRHR ligand binding site.

17. The assay of claim 1, wherein the assay further comprises determining whether the test agent can dissociate from the protein.

18. The assay of claim 1, wherein the test agent is capable of dissociating from the protein with a $K_{off}$ of at least 0.05 $min^{-1}$.

19. The assay of claim 1, wherein the test agent is present in a vehicle that facilitates transport of the test agent through the cell surface membrane and into the cell.

20. The assay of claim 1, wherein an increase in IP production by the cell exposed to the test agent of at least 25%, compared to production of IP by the cell not exposed to the test agent indicates that the test agent is a pharmacoperone agent that restores function to the mutant GnRHR.

21. The assay of claim 1, wherein an increase in IP production by the cell exposed to the test agent of at least 200% compared to production of IP by the cell not exposed to the test agent indicates that the test agent is a pharmacoperone agent that restores function to the mutant GnRHR.

22. The assay of claim 1, wherein IP production is measured by a method comprising;
washing the cell exposed to the test agent to remove the test agent;
incubating the cell with [$^3H$]inositol;
contacting the cell with a GnRHR agonist;
measuring radioactivity incorporated into total IPs.

23. The assay of claim 22, wherein the GnRHR agonist is buserelin (D-tert-butyl-Ser $^6$, des-Gly$^{10}$, Pro$^9$, ethylamide-GnRH), leuprolide (D-Leu$^6$, Pro$^9$, des-Gly$^{10}$-ethylamide-GnRH), or GnRH.

24. The assay of claim 1, wherein the assay comprises:
exposing a cell expressing the mutant GnRHR protein to a test agent; and measuring inositol phosphate (IP) production by the cell, wherein an increase in IP production by the cell expressing the mutant GnRHR protein compared to production of IP by a cell expressing the mutant GnRHR protein not exposed to the test agent indicates that the test agent is a pharmacoperone agent that restores function to the mutant GnRHR.

25. The assay of claim 1, wherein the assay comprises:

exposing a cell expressing the mutant GnRHR protein to a test agent; and measuring GnRHR ligand binding and internalization by the cell expressing the mutant GnRHR protein, wherein an increase in GnRHR ligand binding and internalization by the cell expressing the mutant GnRHR protein as compared to GnRHR ligand binding and internalization by the cell expressing the mutant GnRHR protein not exposed to the test agent indicates that the test agent is a pharmacoperone agent that restores function to the mutant GnRHR.

* * * * *

UNITED STATES PATENT AND TRADEMARK OFFICE
CERTIFICATE OF CORRECTION

PATENT NO. : 7,842,470 B2
APPLICATION NO. : 11/050662
DATED : November 30, 2010
INVENTOR(S) : P. Michael Conn Page 1 of 1

It is certified that error appears in the above-identified patent and that said Letters Patent is hereby corrected as shown below:

Column 29, line 22, "alpharmacoperone" should read --a pharmacoperone--

Column 35, lines 65 and 66, "(such ash $Q^{106}R+S^{217}R^{262}Q$ and $R^{262}/A^{129}D$ pairs and the unreported $L^{314}X_{(stop)}/R^{262}Q$ combination)" should read --(such as the $Q^{106}R+S^{217}R/R^{262}Q$ and $R^{262}/A^{129}D$ pairs and the unreported $L^{314}X_{(stop)}/R^{262}Q$ combination)--

Column 39, line 37, "effect in vivo" should read --effect. In vivo--

Column 40, line 2, "(3.59%+0.20% SEM)" should read --(3.59 % ± 0.20% SEM)--

Column 44, lines 44 and 45, "$S^{168}R,S^{217}R,Q^{106}R/S^{217}R,Q^{106}R/S^{217}R,Q^{106}R/S^{217}R/R^{262}Q$," should read --$S^{168}R, S^{217}R, Q^{106}R/S^{217}R, Q^{106}R/S^{217}R/R^{262}Q$--

Signed and Sealed this
Seventh Day of June, 2011

David J. Kappos
*Director of the United States Patent and Trademark Office*